(12) United States Patent
Remacle et al.

(10) Patent No.: US 7,202,026 B2
(45) Date of Patent: *Apr. 10, 2007

(54) IDENTIFICATION OF A LARGE NUMBER OF BIOLOGICAL (MICRO)ORGANISMS GROUPS AT DIFFERENT LEVELS BY THEIR DETECTION ON A SAME ARRAY

(75) Inventors: José Remacle, Malonne (BE); Sandrine Hamels, Loverval (BE); Nathalie Zammatteo, Jambes (BE); Laurence Lockman, Bastogne (BE); Sophie Dufour, Mons (BE); Isabelle Alexandre, Lesve (BE); Francoise De Longueville, Jambes (BE)

(73) Assignee: Eppendorf Array Technologies SA (EAT), Namur (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/056,229

(22) Filed: Jan. 23, 2002

(65) Prior Publication Data

US 2003/0198943 A1    Oct. 23, 2003

Related U.S. Application Data

(63) Continuation-in-part of application No. 09/817,014, filed on Mar. 23, 2001.

(30) Foreign Application Priority Data

| Mar. 24, 2000 | (EP) | 00870055 |
| Sep. 15, 2000 | (EP) | 00870204 |

(51) Int. Cl.
    *C12Q 1/68*    (2006.01)
(52) U.S. Cl. ....................................................... 435/6
(58) Field of Classification Search ............... 435/4, 435/6, 91.1, 91.2, 7.2, 7.32, 7.33; 536/23.1, 536/23.5, 23.6, 23.7, 24.3, 24.33, 25.32, 536/24.32
See application file for complete search history.

(56) References Cited

U.S. PATENT DOCUMENTS

| 5,143,854 | A |   | 9/1992  | Pirrung et al. |
| 5,312,527 | A |   | 5/1994  | Mikkelsen et al. |
| 5,445,934 | A |   | 8/1995  | Fodor et al. |
| 5,451,512 | A | * | 9/1995  | Apple et al. ............... 435/91.2 |
| 5,510,270 | A |   | 4/1996  | Fodor et al. |
| 5,552,270 | A |   | 9/1996  | Khrapko et al. |
| 5,587,307 | A |   | 12/1996 | Alborn, Jr. et al. |
| 5,683,872 | A |   | 11/1997 | Rudert et al. |
| 5,723,591 | A | * | 3/1998  | Livak et al. ............... 536/22.1 |
| 5,736,257 | A |   | 4/1998  | Conrad et al. |
| 5,770,721 | A | * | 6/1998  | Ershov et al. ............. 536/25.3 |
| 5,800,992 | A |   | 9/1998  | Fodor et al. |
| 5,807,522 | A | * | 9/1998  | Brown et al. ................. 422/50 |
| 5,821,060 | A |   | 10/1998 | Arlinghaus et al. |
| 6,207,648 | B1 | * | 3/2001  | Waxman et al. ............... 514/44 |
| 6,228,575 | B1 | * | 5/2001  | Gingeras et al. ................ 435/5 |
| 6,255,059 | B1 | * | 7/2001  | Klein et al. ................. 435/7.31 |
| 6,306,643 | B1 |   | 10/2001 | Gentalen et al. |
| 6,331,441 | B1 | * | 12/2001 | Balch et al. ................. 436/518 |
| 6,488,932 | B1 | * | 12/2002 | Boon et al. ............... 424/185.1 |
| 6,541,617 | B1 | * | 4/2003  | Bamdad et al. ............. 536/23.1 |
| 2002/0102578 | A1 | * | 8/2002 | Dickinson et al. ............. 435/6 |
| 2005/0106126 | A1 | * | 5/2005 | Whitlock ................... 424/93.4 |
| 2006/0003308 | A1 | * | 1/2006 | Kulisch ......................... 435/2 |

FOREIGN PATENT DOCUMENTS

| EP | 0511559       |   | 11/1992 |
| EP | 0476014       |   | 8/1994  |
| EP | 0535242       |   | 9/1997  |
| GB | 2318791       |   | 6/1998  |
| WO | WO 98/11253   |   | 3/1988  |
| WO | WO 89/11548   |   | 11/1989 |
| WO | 94/05695      |   | 3/1994  |
| WO | WO 94/05695   | * | 3/1994  |
| WO | WO9710364     |   | 3/1997  |
| WO | WO9727317     |   | 7/1997  |
| WO | WO9727329     |   | 7/1997  |
| WO | WO 98/28444   |   | 7/1998  |
| WO | WO 99/16780   | * | 4/1999  |
| WO | WO 99/35499   |   | 7/1999  |
| WO | WO 00/72018   |   | 11/2000 |

OTHER PUBLICATIONS

Musser (Clin Microbiol Rev. (1995) 8(4): 496-514).*
Rose et al. (Nuc. Acid Res. (1998) 26(7): 1628-1635).*
Heredity (1996) 77(6): 608-618, abstract only.*
Guschin et al. Oligonucleotide microchips as genosensors for determinative and environmental studies in microbiology. Appl Environ Microbiol. Jun. 1997;63(6):2397-402.*
Yershov et al. DNA analysis and diagnostics on oligonucleotide microchips. Proc Natl Acad Sci U S A. May 14, 1996;93(10):4913-8.*
Martineau et al. Correlation between the resistance genotype determined by multiplex PCR assays and the antibiotic susceptibility patterns of Staphylococcus aureus and Staphylococcus epidermidis. Antimicrob Agents Chemother. Feb. 2000;44(2):231-8.*
Musser JM. Antimicrobial agent resistance in mycobacteria: molecular genetic insights. Clin Microbiol Rev. Oct. 1995;8(4):496-514. Review.*
Rose et al. Consensus-degenerate hybrid oligonucleotide primers for amplification of distantly related sequences. Nucleic Acids Res. Apr. 1, 1998;26(7):1628-35.*

(Continued)

Primary Examiner—Jeffrey Fredman
Assistant Examiner—Samuel Woolwine
(74) Attorney, Agent, or Firm—Knobbe, Martens, Olson & Bear, LLP

(57) ABSTRACT

The present invention is related to an identification and/or quantification method of a large number of biological organisms groups at different levels (family, genus, species) or part of those (possibly present in a biological sample) by a detection of their nucleotide sequence.

57 Claims, 4 Drawing Sheets

OTHER PUBLICATIONS

Apostolidis et al. Genetic differentiation and phylogenetic relationships among Greek *Salmo trutta*(brown trout) populations as revealed by RFLP analysis of PCR amplified mitochondrial DNA segments. Heredity. Dec. 1996;77 (Pt 6):608-18, abstract only.*

Anthony, et al., Rapid diagnosis of bacteremia by universal amplification of 23S ribosomal DNA followed by hybridization to an oligonucleotide array *Journal of Clinical Microbiology*, 38:781-788, 2000.

Fodor, et al. Multiplexed biochemical assays with biological chips *Nature* 364 555-556, 1993.

Guo, et al. Direct fluorescence analysis of genetic polymorphisms by hybridization with oligonucleotide arrays on glass supports *Nucleic Acids Research* 22 5456-5465, 1994.

Maskos, Uwe and Southern, Edwin M., (1992) Oligonucleotide hybridisations on glass supports a novel linker for oligonucleotide synthesis and hybridisation properties of oligonucleotides synthesised *in situ Nucleic Acids Research.* 20(7) 1679-1684.

Van Ness, et al, A versatile solid support system for oligodeoxynucleotide probe-based hybridization assays *Nucleic Acids Research*, 19 3345-3350, 1991.

Wetmur, et al. Kinetics of renaturation of DNA *J. Mol. Biol.*, 31 349-370, 1968.

Zammatteo, et al (1997) Comparison between microwell and bead supports for the detection of human cytomegalovirus amplicons by sandwich hybridization *Analytical Biochemistry* 253:180-189.

International Search Report EP 00870055.

Remacle, et al. U.S. Appl. No. 09/817,014, filed Mar. 23, 2001, entitled "Identification of Biological (Micro)Organisms by Detector of Their Homologous Nucleotide Sequences on Arrays."

Wu, Dan Y. and R. B. Wallace (1989) *The Ligation Amplification Reaction (LAR)—Amplification of Specific DNA Sequences Using Sequential Rounds of Template-Dependent Ligation.* Genomic 4, pp. 560-569.

Schena, M., et al. (1996) *Parallel Human Genome Analysis: Microarray-based Expression Monitoring of 1000 Genes.* Proc. Natl. Acad. Sci. USA 93, pp. 10614-10619.

International Preliminary Examination Report from co-pending PCT/BE01/00053 dated Mar. 17, 2003, which claims priority to the same European applications as the above-identified application.

Apostolidis, et al., "Genetic differentiation and phylogenetic relationships among Greek *Salmo trutta* L. (brown trout) populations as revealed by RFLP analysis of PCR amplified mitochondrial DNA segments," Heredity, (1996) 77(6): 608-618, abstract only.

Musser, "Antimicrobial Agent Resistance in Mycobacteria: Molecular Genetic Insights," Clinical Microbiol Rev, (1995) 8(4):496-514.

Rose, et al., "Consensus-degenerate hybrid oligonucleotide primers for amplification of distantly related sequences," Nuc. Acid Res. (1998) 26(7): 1628-1635.

Shchepinov, M.S. et al. (1997) "Steric factors influencing hybridization of nucleic acids to oligonucleotide arrays" *Nucleic Acids Research* 25:1155-1161.

Office Action from priority U.S. Appl. No. 09/817,014, dated Nov. 27, 2002.

Office Action from priority U.S. Appl. No. 09/817,014, dated Sep. 11, 2003.

Office Action from priority U.S. Appl. No. 09/817,014, dated Sep. 27, 2004.

Office Action from priority U.S. Appl. No. 09/817,014, dated Mar. 18, 2005.

* cited by examiner

IDENTIFICATION OF A LARGE NUMBER OF BIOLOGICAL (MICRO)ORGANISMS GROUPS AT DIFFERENT LEVELS BY THEIR DETECTION ON A SAME ARRAY

CROSS-REFERENCE TO RELATED APPLICATIONS

This is a continuation-in-part of U.S. patent application Ser. No. 09/817,014 filed Mar. 23, 2001, which claims priority to European Application Serial Number 00870055.1 filed on Mar. 24, 2000, and European Application Serial Number 00870204.5 filed on Sep. 15, 2000, the disclosures of which are incorporated herein by reference in their entireties.

BACKGROUND OF THE INVENTION

1. Field of the Invention

The present invention relates to the diagnosis and analytical assays and is related to a method and kit comprising reagents and means for the identification, detection and/or quantification of a large number of (micro)organisms of different groups (classes, family, genus, species, individual among other ones) by their identification or the identification of a component thereof on a same array.

The invention is especially suited for the simultaneous identification and/or quantification of groups and sub-groups of (micro)organisms or related genes present in the same biological sample.

The present invention also provides a two step method for detecting first for the presence of any of the search (micro) organisms followed by its identification.

2. Description of the Related Art

Identification of an organism or microorganisms can be performed based on the presence in their genetic material of specific sequences. Identification of a specific organism can be performed easily by amplification of a given sequence of the organism using specific primers and detecting or identifying the amplified sequence.

However, in many applications especially in diagnostic, possible organisms present in biological samples are numerous and belong to different families, genus, species, subspecies or even individuals. Amplifications of each of the possible organisms is difficult and expensive. A simple method is thus required for such multi-parametric, multi-levels analysis.

Amplification of a given sequence is performed by several methods such as the polymerase chain reaction (PCR) (U.S. Pat. Nos. 4,683,195 and 4,683,202), ligase chain reaction (LCR) (Wu and Wallace, 1989, Genomics 4: 560–569) or the Cycling Probe Reaction (CPR) (U.S. Pat. No. 5,011,769) which are the most common. One particular way to detect for the presence of a given sequence and thus of a particular organism is to follow the appearance of amplicons during the amplicon cycles. The method is called the real time PCR. A fluorescent signal appears when the amplifications are formed and the amplification is considered as positive when reaching a threshold.

Detecting the amplicons can also be performed after the amplification by methods based on the specific recognition of amplicons to complementary sequences. The first supports used for such hybridization were the nitrocellulose or nylon membranes. However, the methods were miniaturized and new supports such as conducting surfaces, silica, and glass were proposed together with the miniaturization of the detection process. Microarrays or DNA Chips are used for multiple analysis of DNA or RNA sequences either after an amplification step or after a retro-transcription into a cDNA. The target sequences to be detected are labeled during the amplification or copying step and are then detected and possibly quantified on arrays. The presence of a specific target sequence on the arrays is indicative of the presence of a given gene or DNA sequence in the sample and thus of a given organism which may then be identified. The problem of detection becomes difficult when several sequences are homologous to each other, but have to be specifically discriminated upon the same array. This technical problem is the condition to use arrays for many diagnostic purpose since organisms or micro-organisms of interest are often very similar to others on a taxonomic basis and present almost identical DNA sequences.

The Company Affymetrix Inc. has developed a method for direct synthesis of oligonucleotides upon a solid support, at specific locations by using masks at each step of the processing. Said method comprises the addition of a nucleotides on growing synthesized oligonucleotides in order to obtain the desired sequences at the desired locations. This method is derived from the photolithographic technology and is coupled with the use of photoprotective groups, which are released before a new nucleotide is added (U.S. Pat. No. 5,510,270). However, only small oligonucleotides are present on the surface, and said method finds applications mainly for sequencing or identifying a pattern of positive spots corresponding to each specific oligonucleotide bound on the array. The characterization of a target sequence is obtained by cutting this polynucleotide into a small oligo-nucleotides and comparison of the hybridization pattern with a reference sequence. Said technique was applied to the identification of Mycobacterium tuberculosis rpoB gene (WO 97/29212), wherein the capture nucleotide sequence comprises less than 30 nucleotides and from the analysis of two different sequences that may differ by a single nucleotide (the identification of SNPs or genotyping). Small capture oligonucleotide sequences (having a length comprised between 10 and 20 nucleotides) are preferred since the discrimination between two oligonucleotides differing in one base is higher, when their length is smaller.

The method is complicated by the fact that it cannot directly detect amplicons resulting from genetic amplification (PCR). A double amplification is performed with primer(s) bearing a T3 or T7 sequences and then a retrotranscription with a RNA polymerase. These RNA are cut into pieces of about 40 bases before being detected on an array (example 1 of WO 97/29212). Each sequence requires the presence of 10 capture nucleotide sequences and 10 control nucleotide sequences to be identified on the array. The reason for this complex procedure is that long DNA or RNA fragments hybridize very slowly on small oligonucleotide capture nucleotide sequences present on the surface. Said methods are therefore not suited for the detection of homologous sequences, since the homology varies along the sequences and so part of the pieces will hybridize on the same capture nucleotide sequences. Therefore, a software for the interpretation of the results is incorporated in the method for allowing interpretation of the obtained data. The main reason not to perform a single hybridization of the amplicons on the array is that the amplicons will rehybridize in solution much faster than hybridize on the small capture nucleotide sequences of the array.

One consequence of such constraints is that polynucleotides are analyzed on oligonucleotides based arrays, only after being cut into oligonucleotides. For gene expression array which is based on the detection of cDNA copy of the mRNA, the problem still exist but is less acute since the cDNA is single stranded. The fragments are also cut into smaller species and the method requires the use of several capture oligonucleotide sequences in order to obtain a pattern of signals which attest the presence of a given gene. Said cutting also decreases the number of labeled nucleotides, and thus reduces the obtained signal. In the case of cDNA analysis, the use of long capture polynucleotide sequences gives a much better sensitivity to the detection. In many gene expression applications, the use of long capture nucleotide sequences is not a problem, when cDNAs to be detected originate from genes having different sequences, since the difference in the sequence is sufficient in order to avoid cross reactions between them even on a sequence longer than 100 bases so that polynucleotides can be used as capture nucleotide sequences. Long capture nucleotide sequences give the required sensitivity but they will hybridize to other homologous sequences.

The detection of Single Nucleotide Polymorphism in the DNA is just one particular aspect of the detection of homologous sequences. The use of arrays has been proposed to discriminate two sequences differing by one nucleotide at a particular location of the sequence. Since DNA or RNA sequences are in low copy numbers, their sequences are first amplified so that double stranded sequences are analyzed on the array. Several methods have been proposed to detect such a base change in one location. The document WO 97/31256 proposes the use of two oligonucleotide sequences: the first one with a part specific and a part addressable, the second one with a part specific and a part labeled. After ligation in solution, the product is immobilized on an array with capture nucleotide sequences with a least a part complementary of the addressable part. The detection of SNP is the basis for polymorphism determination of individual organism, but also for its genotyping, since the genome of individuals differ from each other in the same species or subspecies by said SNPs. The presence of particular SNP affect the activities of enzymes like the P450 and make them more or less active in the metabolism of a drug.

The capture oligonucleotide present on the array can also be used as primers for extension once the target nucleotide hybridized. The document WO 96/31622 proposes to identify a nucleotide at a given location upon a sequence by elongation of a capture nucleotide sequence with detectable modified nucleotides in order to detect the given spots, where the target has been bound with the last nucleotide of the capture nucleotide sequence being complementary of a target sequence at this particular position. The document WO 98/28438 proposes to complete several cycles of hybridization-elongation steps to label a spot in order to compensate for a low hybridization yield of the target sequence. This method allows identification of a nucleotide at a given location of a sequence by labeling of a spot of the elongated capture nucleotide sequence.

Prior to elongation, the capture nucleotide sequences present on the array can be digested by a nuclease in order to differentiate between matched and the unmatched heteroduplexes (U.S. Pat. No. 5,753,439). Use of nuclease for identification of sequences has also been proposed (EP 0721016). A second labeled nucleotide sequence complementary of the targets has also been proposed to be added to the hybridized targets and being ligate to the capture nucleotide sequence if the last nucleotide of the targets is complementary to the targets a this position (WO 96/31622).

The document EP-0785280 proposes a detection of polymorphism based on the hybridization of the target nucleotides on blocks containing several oligonucleotide sequences differing by one base each and obtain a ratio of intensity for determining which sequences are the perfect hybridization matches.

Using membranes or nylon supports are proposed to increase the sensitivity of the detection of polynucleotides on solid support by incorporation of a spacer between the support and the capture nucleotide sequences. Van Ness et al. (Nucleic Acids Research, vol. 19, p. 3345, 1991) describe a poly(ethyleneimine) arm for the binding of DNA on nylon membranes. The document EP-0511559 describes a hexaethylene glycol derivative as spacer for the binding of small oligonucleotides upon a membrane. When membranes like nylon are used as support, there is no control of the site of binding between the solid support and the oligonucleotides and it was observed that a poly dT tail increased the fixation yield and so the resulting hybridization (WO 89/11548).

Guo et al. (Nucleic Acids Research 22, 5456, 1994) teach the use of poly dT of 15 bases as spacer for the binding of oligonucleotides on glass with increased sensitivity of hybridization.

The publication of Anthony et al. (Journal of clinical microbiology, vol. 38:2, p. 7817–8820) describes the use of a membrane array for the detection of 23 S ribosomal DNA of various bacterial species after PCR amplification. Targets to detect are rDNA amplified from bacteria by consensus PCR and the detection is obtained on nylon array containing capture nucleotide sequences for said bacteria and having the capture nucleotide sequences having between 20 and 30 bases which are covalently linked to the nylon, and there is no control of the portion of the sequence which is available for hybridization. rDNA are multi-copies DNA which are used in order to compensate for the low detection yield of the method. Also, because of the use of small capture nucleotide sequences they can only detect individual bacterial species by their specific sequence and not the family or genus.

However these patents neither described nor suggested that it is was possible to use a component of a (micro) organism, especially a genetic sequence, to identify said (micro)organism together with the identification of the group to which these (micro)organisms belong. Also there is neither an indication nor a suggestion in the state of the art that polynucleotides can be used as capture sequences in microarrays in order to differentiate a binding between homologous polynucleotides sequences and to permit identification of one target sequence among other species, genus or families of (micro)organisms sequences.

Also there is no indication nor suggestion that homologous sequences differing by one nucleotide at one location of the sequence (such as observed in polymorphism analysis) could be detected by hybridization of the amplified sequences on corresponding capture nucleotide sequences.

Prior to the invention, it was unknown that it is possible to identify in a two step process, i.e. an amplification followed by a direct hybridization of the amplicons on an array, organisms belonging to the same group, to two groups or more together with the specific identification of the groups as such. Also it was unknown that it was possible to identify organisms belonging to a group and sub-group together with the specific identification of these group and sub-group. Also that such identification could be obtained by using polynucleotide as capture sequences for all detections.

Also it was unknown that polynucleotides could be used for the identification of homologous polynucleotide sequences differing by one nucleotide present in a particular location of the sequence.

Also it was unknown that homologous polynucleotide sequences could be discriminated and detected on an array directly after amplification with a very high sensitivity.

SUMMARY OF THE INVENTION

The present invention is premised in part on the discovery that arrays can be used to obtain a discrimination between a homologous (biological) component (such as a genetic sequence) of different (micro)organisms belonging to several groups together with the identification of these groups as such.

The present invention is especially useful in using arrays to discriminate between homologous genetic sequences (amino acid sequences and nucleotide sequences) belonging to several groups of organisms together with the identification of these groups as such.

The invention provides a method and a device which are based upon a simplified technology requiring the use of a single or limited number of primer pair(s) in an amplification step to detect the presence of the specific target or group of target sequence(s) and followed by the identification (detection and/or quantification) of said specific target or groups of target genetic sequence(s) by recording in a single spot identification upon said micro-array and in the same experimental protocol, said signal being either specific of the organism or the group or sub-group of organisms.

The present invention further provides means for an identification of organisms differing by single base difference of a given nucleotide sequence followed by hybridization of their amplified polynucleotide sequences upon arrays.

DEFINITIONS

Figure 1:
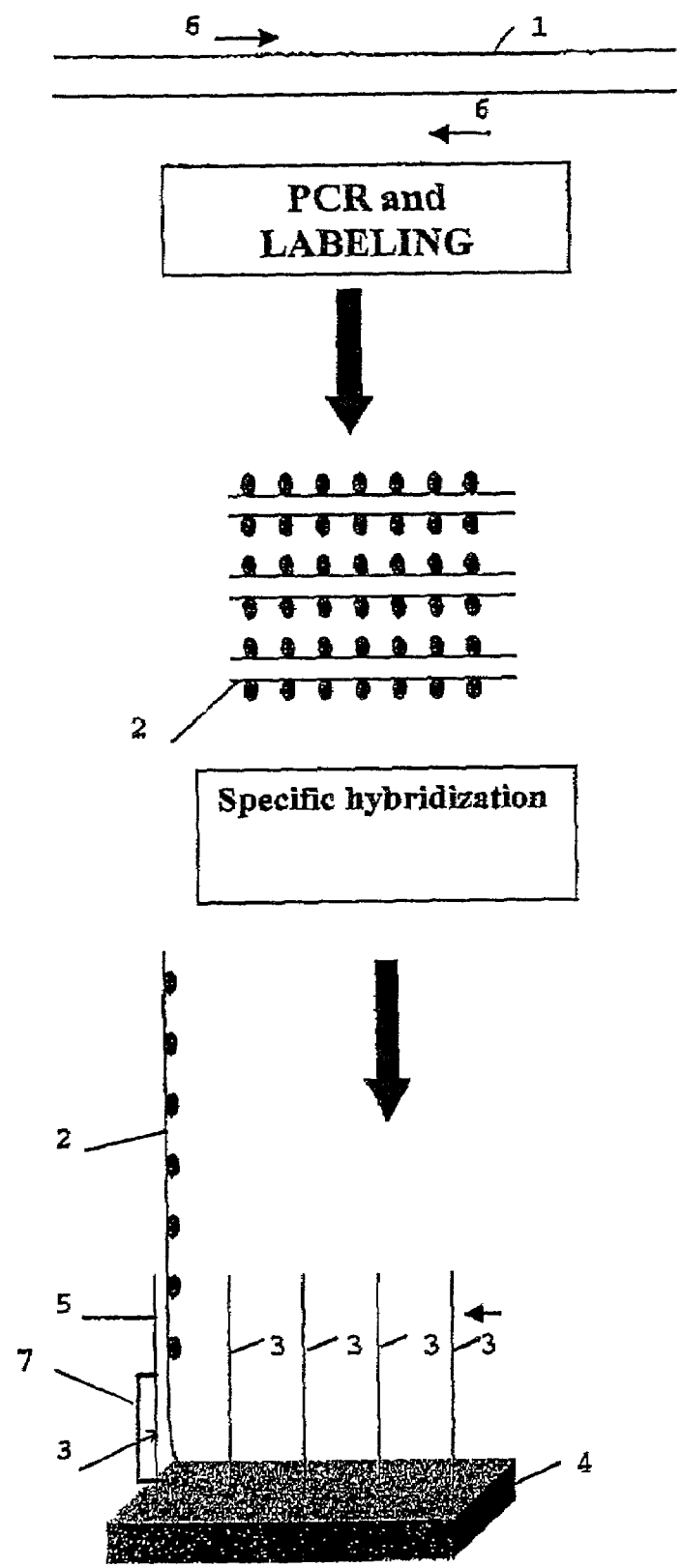
FIG. 1 is a schematic presentation of the step used in the method of the invention for the identification of 5 *Staphylococcus* species on biochips after PCR amplification with consensus primers.
Figure 2:
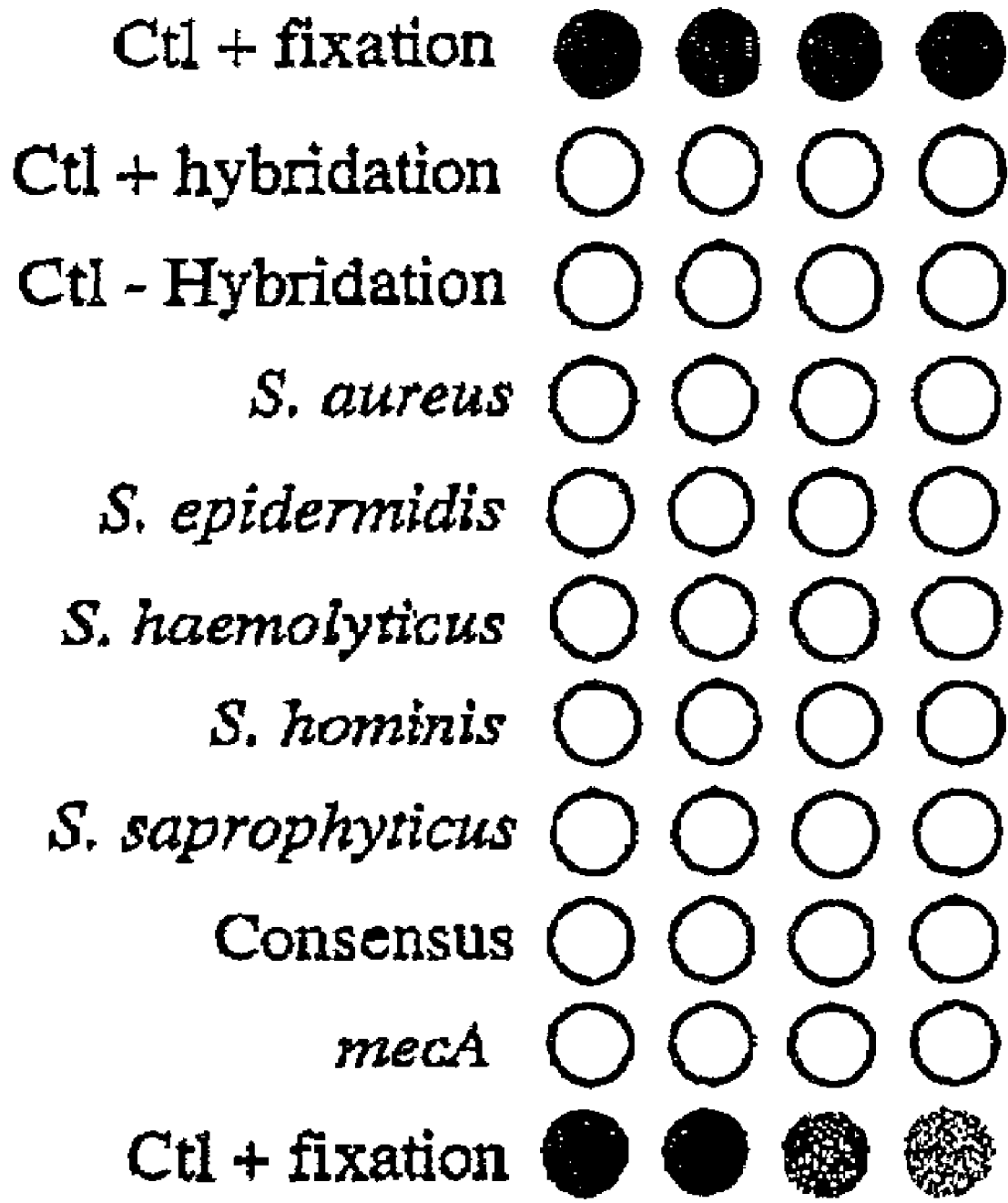
FIG. 2 represents the design of an array which allows the determination of the 5 most common *Staphylococcus* species, of the presence of any *Staphylococcus* strain and of the MecA gene.
Figure 3:
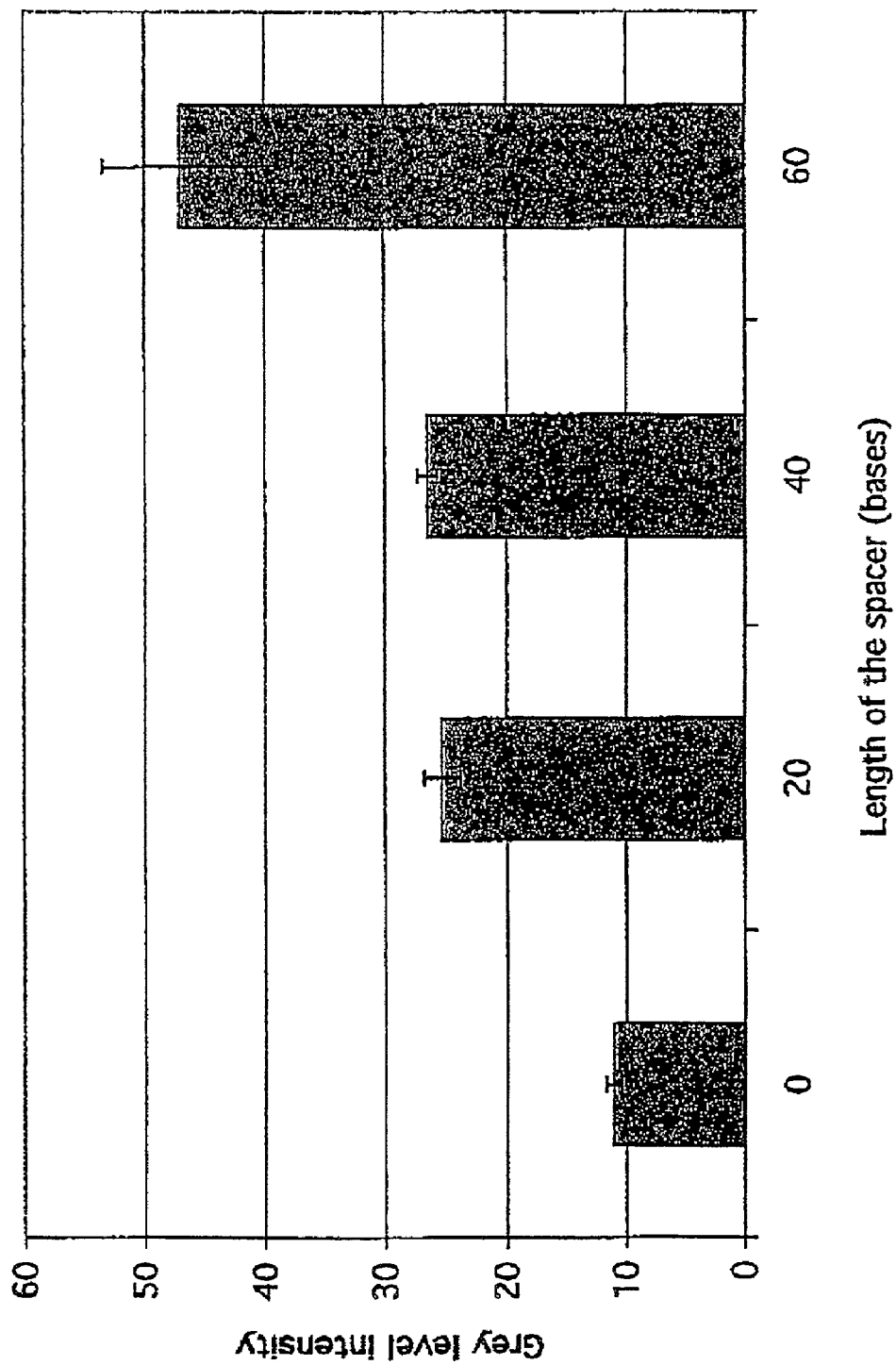
FIG. 3 presents the effect of the length of the specific sequence of a capture nucleotide sequence on the discrimination between sequences with different level of homology.
Figure 4:
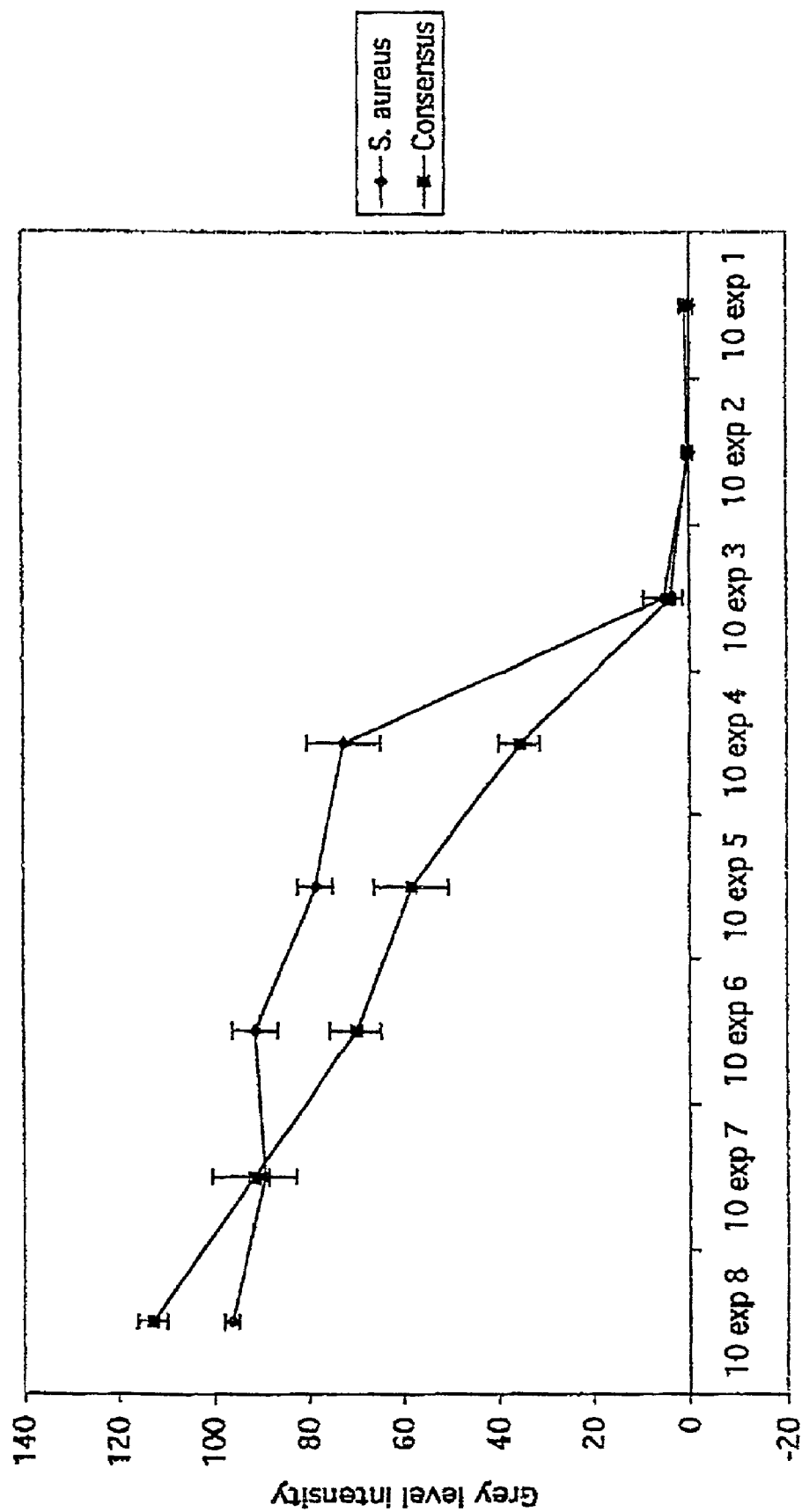
FIG. 4 shows the sensitivity obtained for the detection of FemA sequences from *S. aureus* on array bearing the small specific capture nucleotide sequence for a *S. aureus* and a consensus sequence.

The terms "nucleic acid, oligonucleotide, array, nucleotide sequence, target nucleic acid, bind substantially, hybridizing specifically to, background, quantifying" are the ones described in the international patent application WO 97/27317 incorporated herein by reference. The term polynucleotide refers to nucleotide or nucleotide like sequences of more than 100 bases long.

The terms "nucleotide triphosphate, nucleotide, primer sequence" are those described in the document WO 00/72018 and WO 01/31055 incorporated herein by references.

The terms "homologous genetic sequences" mean amino acid or nucleotide sequences having a percentage of amino acids or nucleotides identical at corresponding positions which is higher than in purely random alignments. They are considered as homologous when they show a minimum of homology (or sequence identity) defined as the percentage of identical nucleotides or amino acids found at each position compared to a total of nucleotides or amino acids, after the sequences have been optimally aligned taking into account additions or deletions (like gaps) in one of the two sequences to be compared. Genes coding for a given protein but present in genetically different sources like different organisms are usually homologous. Also in a given organism, genes coding for proteins or enzymes of the same family (Interleukins, cytochrome b, p. 450). The degree of homology (or sequence identity) can vary a lot as homologous sequences may be homologous only in one part, a few parts or portions or all along their sequences. The parts or portions of the sequences that are identical in both sequences are said conserved. Protein domains which present a conserved three dimensional structure are usually coded by homologous sequences and even often by a unique exon. The sequences showing a high degree of invariance in their sequences are said to be highly conserved and they present a high degree of homology.

The terms "group, sub-group and sub-sub-group" refer first to the classification of biological organisms in taxas kingdom, branches, classes, orders, families, genus, species, sub-species, varieties or individuals. These constitute different levels of biological taxonomical organization. Groups also refer to organisms which have some aspects in common, but some genetic difference like for example the GMO plants, transgenic or chimeric animals. For the purpose of this invention, the common aspects have to be reflected into common or homology DNA or RNA sequences and the dissimilarities or differences in DNA sequences. Genes sequences can also be classified in groups and sub-group independently of their organism origins and are as such part of the invention. They will then refer to groups or sub-groups of genes which belong to a given family such as the cytochrome P450 genes, the protein kinases, the G receptor coupled proteins and others. These genes are homologous to each other as defined here above.

Classification of genes (nucleotide sequences) are used as the basis of molecules paleontology for establishing the classification of organisms into species, genus, family, orders, classes branches, kingdom and taxus.

DETAILED DESCRIPTION OF THE PREFERRED EMBODIMENT

The present invention is related to an identification and/or quantification method of a biological (micro)organism or a (biological) component thereof, said (micro)organism or its component being possibly present in a sample, preferably a biological sample, among at least two, preferably at least four, other related (micro)organisms or components; said method comprising the step of:

possibly extracting original components from the (micro)organisms;

possibly labeling said (micro)organism or its components being target, putting into contact the (micro)organism or its components being targets with capture molecules bound to an insoluble support, preferably a non-porous solid support, discriminating the binding of said targets, specific of a (micro)organism or its component by detecting, quantifying and/or recording a signal resulting from the specific binding between said targets and their corresponding specific capture molecules; wherein said capture molecules are bound to an insoluble solid support at a specific location according to an array, said array having a density of at least 4 different bound capture molecules/cm$^2$ of solid support surface and wherein the binding between the targets and their corresponding capture molecules forms said signal at the expected location, the detection of a single signal allowing a discrimination of a target being specific of said (micro)organism or its components from other related (micro)organisms or other related components.

Advantageously, said method further comprises the step of identifying and/or quantifying the presence of several groups, subgroups or sub-subgroups of components or (micro)organisms, comprising said components being related to each other until possible individual genetic sequences (nucleotide and/or amino acid sequences) wherein the binding of targets and corresponding specific capture molecules forms a signal at an expected location allowing the identification of a target specific of a group, sub-group or sub-subgroup of components or (micro)organisms comprising said components.

Therefore, the biological component according to the invention could be a nucleotide sequence specific of a (micro)organism or an amino acid sequence (peptide) specific of a (micro)organism. Examples of said molecules are homologous nucleotide sequences or peptides presenting a high homology such as receptors, HLA molecules, cytochrome P450, etc.

Furthermore, the inventors have discovered that it is possible to drastically simplify the identification or quantification of one or several (micro)organisms among many other ones present in such biological sample, said identification and/or quantification being obtained by combining a single amplification using common primer pairs and an identification of the possible (micro)organisms by detecting, quantifying and/or possibly recording upon an array the presence of a single signal resulting only between a capture nucleotide sequence and its corresponding target nucleotide sequence and thereafter correlating the presence of said detected target nucleotide sequence to the identification of a nucleotide sequence specific of said (micro)organism(s).

This means that the method and device according to the invention will allow the easy identification/detection of a specific sequence among other homologous sequences and possibly its quantification (characterization of the number of copies or presence of said organisms in a biological sample) of a target nucleotide sequence, said target sequence having a nucleotide sequence specific of said (micro)organisms.

Such identification may be obtained directly, after washing of possible contaminants (unbound sequences), by detecting and possibly recording a single spot signal at one specific location, wherein said capture nucleotide sequence was previously bound and said identification is not a result of an analysis of a specific pattern upon the microarray as proposed in the system of the state of the art. Therefore, said method and device do not necessarily need a detailed analysis of said pattern by an image processing and a software analysis.

This invention was made possible by discovering that target sequences can be discriminated from other homologous ones upon an array with high sensitivity by using bound capture nucleotide sequences composed of at least two parts, one being a spacer bound by a single and advantageously predetermined (defined) link to the support (preferably a non porous support) and the other part being a specific nucleotide sequence able to hybridize with the nucleotide target sequence.

Furthermore, said detection is greatly increased, if high concentrations of capture nucleotide sequences are bound to the surface of the solid support.

The present invention is related to the identification of a target nucleotide sequence obtained from a biological (micro)organism or a portion thereof, especially a gene possibly present in a biological sample from at least 4 other homologous (micro)organisms or a portion thereof, said other (micro)organisms could be present in the same biological sample and have homologous nucleotide sequences with the target.

Said identification is obtained firstly by a genetic amplification of said nucleotide sequences (target and homologous sequences) by common primer pairs followed (after washing) by a discrimination between the possible different target amplified nucleotide sequences. Said discrimination is advantageously obtained by hybridization upon the surface of an array containing capture nucleotide sequences at a given location, specific for a target nucleotide sequence specific for each (micro)organism to be possibly present in the biological sample and by the identification of said specific target nucleotide sequence through the identification and possibly the recording of a signal resulting from the specific binding of this target nucleotide sequence upon its corresponding capture nucleotide sequence at the expected location (single location signal being specific).

According to the invention, the preferred method for genetic amplification is the PCR using two anti-parallel consensus primers which can recognize all said target homologous nucleotide sequences but other genetic amplification methods may be used.

Therefore, said (micro)organisms could be present in any biological material or sample including genetic material obtained (virus, fungi, bacteria, plant or animal cell, including the human body). The biological sample can be also any culture medium wherein microorganisms, xenobiotics or pollutants are present, as well as such extract obtained from a plant or an animal (including a human) organ, tissue, cell or biological fluid (blood, serum, urine, sputum, etc).

The method according to the invention can be performed by using a specific identification (diagnostic and/or quantification) kit or device comprising at least an insoluble solid support upon which are bound single stranded capture nucleotide sequences (preferably bound to the surface of the solid support by a direct covalent link or by the intermediate of a spacer) according to an array with a density of at least 4, preferably at least 10, 16, 20, 50, 100, 1000, 4000, 10 000 or more, different single stranded capture nucleotide sequences/cm$^2$ insoluble solid support surface, said single stranded capture nucleotide sequences having advantageously a length comprised between about 30 and about 600 bases (including the spacer) and containing a sequence of about 3 to about 60 bases, said sequence being specific for the target (which means that said bases of said sequence are able to form a binding with their complementary bases upon the sequence of the target by complementary hybridization). Preferably, said hybridization is obtained under stringent conditions (under conditions well-known to the person skilled in the art).

In the method and kit or device according to the invention, the capture nucleotide sequence is a sequence having between 16 and 600 bases, preferably between 30 and 300 bases, more preferably between 40 and 150 bases and the spacer is a chemical chain of at least 6.8 nm long (of at least 4 carbon chains), a nucleotide sequence of more than 15 bases or is nucleotide derivative such as PMA.

The method, kit and device according to the invention are particularly suitable for the identification of a target, being preferably biological (micro)organisms or a part of it, possibly present in a biological sample where at least 4, 12, 15 or even more homologous sequences are present. Because of the high homology, said nucleotide sequence can be amplified by common primer(s) so that the identification of the target nucleotide sequence is obtained specifically by the discrimination following its binding with the corresponding capture nucleotide sequence, previously bound at a given location upon the microarray. The sensitivity can be also greater increased if capture nucleotide sequences are spotted to the solid support surface by a robot at high density according to an array. A preferred embodiment of the invention is to use an amount of capture nucleotide sequences spotted on the array resulting in the binding of between about 0.01 to about 5 pmoles of sequence equivalent/$cm^2$ of solid support surface.

The kit or device according to the invention may also incorporate various media or devices for performing the method according to the invention. Said kit (or device) can also be included in an automatic apparatus such as a high throughput screening apparatus for the detection and/or the quantification of multiple nucleotide sequences present in a biological sample to be analyzed. Said kit or apparatus can be adapted for performing all the steps or only several specific steps of the method according to the invention.

In the method, the kit (device) or apparatus according to the invention, the length of the bound capture nucleotide sequences is preferably comprised between about 30 and about 600 bases, preferably between about 40 and about 400 bases and more preferably between about 40 and about 150 bases. Longer nucleotide sequences can be used if they do not lower the binding yield of the target nucleotide sequences usually by adopting hairpin based secondary structure or by interaction with each other.

In a preferred embodiment, the specific part of the capture nucleotide sequence is bound onto a nucleotide sequence of between 20 and 600 bases.

In another preferred embodiment, all capture molecules are polynucleotides of more than 100 base long.

In another embodiment, the capture nucleotide sequence is linked to a polymer molecule bound to the solid support. The polymer is preferably a chain of at least 10 atoms, selected from the group consisting of poly-ethyleneglycol, polyaminoacids, polyacrylamide, poly-aminosaccharides, polyglucides, polyamides, polyacrylate, polycarbonate, polyepoxides or poly-ester (possibly branched polymers).

If the homology between the sequences to be detected is low (between 30 and 60%), parts of the sequence which are specific in each sequence can be used for the design of specific capture nucleotide sequences binding each of the different target sequences. However, it is more difficult to find part of the sequence sufficiently conserved as to design "consensus" sequences which will amplify or copy all desired sequences. If one pair of consensus primers is not enough to amplify all the homologous sequences, then a mixture of two or more primers pairs is added in order to obtain the desired amplifications. The minimum homologous sequences amplified by the same consensus primer is two, nut there is no limitation to said number.

If the sequences show high degree of homology, higher than 60% and even higher than 90%, then the finding of common sequence for consensus primer is easily obtained, but the choice for specific capture nucleotide sequences become more difficult.

In another preferred embodiment of the invention, the capture nucleotide sequences are chemically synthesized oligonucleotides sequences shorter than 100 bases (easily performed on programmed automatic synthesizer). Such sequences can bear a functionalized group for covalent attachment upon the support, at high concentrations.

Longer capture nucleotide sequences are preferably synthesized by (PCR) amplification (of a sequence incorporated into a plasmid containing the specific part of the capture nucleotide sequence and the non specific part (spacer)).

In a further embodiment of the invention, the specific sequence of the capture nucleotide sequence is separated from the surface of the solid support by at least about 6.8 nm long, equivalent to the distance of at least 20 base pair long nucleotides in double helix form.

In the method, kit (device) or apparatus according to the invention, the portion(s) (or part(ies)) of the capture nucleotide sequences complementary to the target is comprised between about 3 and about 60 bases, preferably between about 15 and about 40 bases and more preferably between about 20 and about 30 bases. These bases are preferably assigned as a continuous sequence located at or near the extremity of the capture nucleotide sequence. This sequence is considered as the specific sequence for the detection. In a preferred form of the invention, the sequence located between the specific capture nucleotide sequence and the support is a non specific sequence.

In another embodiment of the invention, a specific nucleotide sequence comprising between about 3 and about 60 bases, preferably between about 15 and about 40 bases and more preferably between about 20 and about 30 bases is located on a capture nucleotide sequence comprising a sequence between about 30 and about 600 bases.

The method, kit (device) or apparatus according to the invention are suitable for the detection and/or the quantification of a target which is made of DNA or RNA, including sequences which are partially or totally homologous upon their total length.

The method according to the invention can be performed even when a target present between an homology (or sequence identity) greater than 30%, greater than 60% and even greater than 80% and other molecules.

In the method, kit (device) or apparatus according to the invention, the capture nucleotide sequences are advantageously covalently bound (or fixed) upon the insoluble solid support, preferably by one of their extremities as described hereafter.

The method according to the invention gives significant results which allows identification (detection and quantification) with amplicons in solutions at concentration of lower than about 10 nM, of lower than about 1 nM, preferably of lower than about 0.1 nM and more preferably of lower than about 0.01 nM (=1 fmole/100 µl).

Another important aspect of this invention is to use very concentrate capture nucleotide sequences on the surface. If too low, the yield of the binding is quickly lower and is undetectable. Concentrations of capture nucleotide sequences between about 600 and about 3,000 nM in the spotting solutions are preferred. However, concentrations as low as about 100 nM still give positive results in favorable cases (when the yield of covalent fixation is high or when the target to be detected is single stranded and present in high concentrations). Such low spotting concentrations would give density of capture nucleotide sequence as low as 20 fmoles per cm$^2$. On the other side, higher density was only limited in the assays by the concentrations of the capture solutions, but concentrations still higher than 3,000 nM give good results.

The use of these very high concentrations and long nucleotide sequences are two unexpected characteristic features of the invention. The theory of DNA hybridization proposed that the rate of hybridization between two DNA complementary sequences in solution is proportional to the square root of the DNA length, the smaller one being the limited factor (Wetmur, J. G. and Davidson, N. 1968, J. Mol. Biol. 3, 584). In order to obtain the required specificity, the specific sequences of the capture nucleotide sequences had to be small compared to the target. Moreover, the targets were obtained after PCR amplification and were double stranded so that they reassociate in solution much faster than to hybridize on small sequences fixed on a solid support where diffusion is low thus reducing even more the rate of reaction. It was unexpected to observe a so large increase in the yield of hybridization with the same short specific sequence.

The amount of a target which "binds" on the spots is small compared to the amount of capture nucleotide sequences present. So there is a large excess of capture nucleotide sequence and there was no increase of binding if more capture nucleotide sequences were present.

One may perform the detection on the full length sequence obtained after amplification or copy and when labeling is performed by incorporation of labeled nucleotides, more markers are present on the hybridized target making the assay sensitive.

The method, kit and apparatus according to the invention may comprise the use of other bound capture nucleotide sequences, which may have the same characteristics as the previous ones and may be used to identifying a target from another group of homologous sequences (preferably amplified by common primer(s)).

In the microbiological field, one may use consensus primer(s) specific for each family, or genus, of microorganisms and then identify some or all the species of these various family in an array by using capture nucleotide sequences of the invention. Detection of other sequences can be advantageously performed on the same array (i.e. by allowing an hybridization with a standard nucleotide sequence used for the quantification, with consensus capture nucleotide sequences for the same or different micro-organisms strains, with a sequence allowing a detection of a possible antibiotic resistance gene by micro-organisms or for positive or negative control of hybridization). Said other capture nucleotide sequences have (possibly) a specific sequence longer than 10 to 60 bases and a total length as high as 600 bases and are also bound upon the insoluble solid support (preferably in the array made with the other bound capture nucleotide sequences related to the invention). A long capture nucleotide sequence may also be present on the array as consensus capture nucleotide sequence for hybridization with all sequences of the microorganisms from the same family or genus, thus giving the information on the presence or not of a microorganism of such family, genus in the biological sample.

The same array can also bear capture nucleotide sequences specific for a bacterial group and as specific application to Gram-positive or Gram-negative strains or even all the bacteria.

Another application is the detection of homologous genes from a consensus protein of the same species, such as various cytochromes P450 by specific capture nucleotide sequences with or without the presence of a consensus capture nucleotide sequence for all the cytochromes P450 possibly present in a biological sample. Such detection is performed at the gene level by retrotranscription into cDNA.

The solid support according to the invention can be or can be made with materials selected from the group consisting of glasses, electronic devices, silicon supports, plastic supports, silica, metal or a mixture thereof in format such as slides, compact discs, gel layers, microbeads. Advantageously, said solid support is a single glass slide which may comprise additional means (barcodes, markers, etc.) or media for improving the method according to the invention.

The amplification step used in the method according to the invention is advantageously obtained by well known amplification protocols, preferably selected from the group consisting of PCR, RT-PCR, LCR, CPT, NASBA, ICR or Avalanche DNA techniques.

Advantageously, the target nucleotide sequence to be identified is labeled previously to its hybridization with the single stranded capture nucleotide sequences. Said labeling (with known techniques from the person skilled in the art) is preferably also obtained upon the amplified sequence previously to the denaturation (if the method includes an amplification step).

Advantageously, the length of the target nucleotide sequence is selected as being of a limited length preferably between 50 and 2000 bases, preferably between 100 and 400 bases and more preferably between 100 and 200 bases. This preferred requirement depends on the possibility to find consensus primers to amplify the required sequences possibly present in the sample. Too long target nucleotide sequence may reallocate faster and adopt secondary structures which can inhibit the fixation on the capture nucleotide sequences.

The amplified target nucleotide sequence can be cut before the hybridization, and the use of one capture sequence for each target sequence to make the interpretation of the results easy.

The detection of homologous expressed genes is obtained by first retrotranscription of the mRNA by a consensus primer, the preferred one being the poly dT. In one embodiment, the retrotranscribed cDNA is then amplified by consensus primers as described in this invention.

According to a further aspect of the present invention, the method, kit (device) or apparatus according to the invention is advantageously used for the identification of different *Staphylococcus* species or variant, preferably the *S. aureus*, the *S. epidermidis*, the *S. saprophyticus*, the *S. hominis* or the *S. haemolyticus* for homologous organs present together or separately in the biological sample, said identification being obtained by detecting the genetic variants of the FemA gene in said different species, preferably by using a common locations in the FemA genetic sequence (examples 4, 5, 6, 7). In another aspect of the invention, 16 *Staphylococcus* species could be detected after amplification by the same primers and identification on the array (example 7).

Preferably, the primer(s) and the specific portions of said FemA sequence used for obtaining amplified products are the ones described hereafter in example 2. These primers have been selected as consensus primers for the amplification of the FemA genes of all of the 16 *Staphylococcus* tested and they probably will amplify the FemA from all other possible *Staphylococcus* species.

A further aspect of the invention is the detection of *Mycobacteria* species, the *M. tuberculosis* and other species, preferably the *M. avium, M. gastrii, M gordonae, M. intra-*

*cellulare, M. leprae, M. kansasi, M. malmoense, M. marinum, M. scrofulaceum, M. simiae, M. szulgai, M. xenopi, M. ulcerans* (example 8).

In a further application of the invention, one array can specifically detect amplified sequences from several bacterial species belonging to the same genus (examples 7 and 8) or from several genus like *Staphylococcus, Streptococcus, Enterococcus, Haemophilus* (see table 1) or different bacterial species and genus belonging to the Gram-positive bacteria and/or to the Gram-negative bacteria (examples 16 and 22).

Preferably, the primer(s) and the specific portions of gyrase (sub-unit A) sequences are used for obtaining amplified products. These primers have been selected as consensus primers for the amplification of the gyrase genes of all of the bacteria tested and they probably will amplify the gyrase from many other possible bacteria species and genus and families.

The invention is particularly suitable for detection of bacteria belonging to at least two of the following genus families: *Staphylococcus, Enterococcus, Streptococcus, Haemolyticus, Pseudomonas, Campylobacter, Enterobacter, Neisseria, Proteus, Salmonella, Simonsiella, Riemerella, Escherichia, Neisseria, Meningococcus, Moraxella, Kingella, Chromobacterium, Branhamella.*

The array allows to read the MAGE number by observation of the lines positive for signal bearing the specific capture nucleotide sequences.

The same application was developed for the G Protein Coupled Receptors (GPCR). These receptors bind all sort of ligands and are responsible for the signal transduction to the cytoplasm and very often to the nucleus by modulating the activity of the transcriptional factors. Consensus primers are formed for the various subtypes of GPCR for dopamine and for serotonin and histamine. The same is possible for the histamine and other ligands.

The detection of the various HLA types is also one of the applications of the invention. HLA are homologous sequences which differ from one individual to the other. The determination of the HLA type is especially useful in tissue transplantation in order to determine the degree of compatibility between the donor and the recipient. It is also a useful parameter for immunization. Given the large number of subtypes and the close relation between the homologous sequences it was not always possible to perfectly discriminate one sequence among all the other ones and for some of them there was one or two cross-reactions. In this case, a second capture nucleotide sequence complementary to another location of the amplified sequence was added on the array, in order to make the identification absolute.

Genetic sequences code for proteins so that homologous DNA sequences correspond to homologous amino acid sequences of the encoded proteins while variation in the DNA sequences correspond to variation in amino acid sequence. One embodiment of this invention is to use antibodies for specific capture of proteins from a sample in order to identify the protein and so the organism from which it originates. By choosing appropriate antibodies, the organisms or the group to which it belongs is determined. The HLA typing is given as example of the use of specific antibodies for discriminating the various HLA-A proteins on an array (example 23).

Discrimination of the Cytochrome P450 forms is one particular application of the invention (example 14).

The detection of polymorphism sequences (which can be considered as homologous even if differing by only one base) can be made also by the method according to the invention. This is especially useful for the Cytochrome P450 since the presence of certain isoforms modifies the metabolism of some drugs. The invention was found particularly useful for discriminating between the isoforms of Cyto P450 2D6 and 2C19. More generally the invention is particularly well adapted for the discrimination of sequences differing by one base mutation or deletion called Single Nucleotide Polymorphism (SNP). The originality of the invention is to perform the hybridization step directly on the amplified sequences without the necessity to copy into RNA and to cut them into pieces.

Furthermore, one array can specifically detect amplified sequences from several animal species and genus belonging to several families like Galinacea, Leporidae, Suidae and Bovidae (table 2).

One array can specifically detect amplified sequences from several fishes species, such as *G. morhua, G. macrocephalus, P. flesus, M. merluccius, O. mykiss, P. platessa, P. virens, S. salar, S. pilchardus, A. thazard, T. alalunga, T. obesus, R. hippoglossoides, S. trutta, S. sarda, T. thynnus, S. scombrus* belonging to several genera such as *Auxis, Sarda, Scomber, Thunnus, Oncorhynch, Salmo, Merluccius, Pleuronectes, Platichtlys, Reinhardtius, Pollachius, Gadus, Sardina,* from several families such as Scombridae, Salmonidae, Merluccidae, Pleuronectidae, Gadidae and Clupeidae. (Table 3) Other homologous sequences allow the determination of plant species and genus such as Potato, tomato, oryza, zea, soja, wheat, barley, bean, carrot belonging to several families (example 19).

According to a further aspect of the present invention, the method, kit (device) or apparatus according to the invention is advantageously used for the identification of the origin of meat (table 2).

Preferably, the primer(s) and the specific portions of cytochrome b sequences are used for obtaining amplified products are the ones described hereafter in example 3. These primers have been selected as consensus primers for the amplification of the cytochrome B genes of all of animals tested and they probably will amplify the cytochrome B from many other animals species, genus and families.

According to a further aspect of the present invention, the method, kit (device) or apparatus according to the invention is advantageously used for the identification of the origin of fishes (table 3).

Preferably, the primer(s) and the specific portions of said cytochrome b sequences used for obtaining amplified products are the ones described hereafter in example 18. These primers have been selected as consensus primers for the amplification of the cytochrome B genes of all of fishes tested and they probably will amplify the cytochrome B from many other fishes species, genus and families.

According to a further aspect of the present invention, the method, kit (device) or apparatus according to the invention is advantageously used for the identification of the origin of plants.

Preferably, the primer(s) and the specific portions of said sucrose synthase sequences used for obtaining amplified products are the ones described hereafter in the examples. These primers have been selected as consensus primers for the amplification of the sucrose synthase genes of all of plants tested and they probably will amplify the sucrose synthase from many other plants species, genus and families.

According to a further aspect of the present invention, the method, kit (device) or apparatus according to the invention is advantageously used for the identification of the Genetically Modified Organism (GMO). The GMO are produced by insertion into the genome of an organism of one or several external genes together with other regulating or construction sequences.

Preferably, the primer(s) and the specific portions of said sucrose synthase sequences used for obtaining amplified products are the ones described hereafter in the examples. These primers have been selected as consensus primers.

Homologous DNA or RNA sequences lead to the expression in cells or tissues of proteins which are also homologous to each other. Therefore, a target component to be detected may be protein which is related to other homologous ones which could be present in the same biological sample. Related proteins means proteins which have some part(s) of their sequence or conformation in common, while said proteins present other part(s) which are specific or the (micro)organisms or a part of said (micro)organisms from which they originate.

Part or portion of the amino acid sequences are identical between proteins from the same group while other portions are specific of the target to be identified and possibly quantified. Said amino acid sequences present linear or conformational epitopes which can be recognized by specific (monoclonal) antibodies. The discrimination between said specific related targets is possible by specific antibodies or reconstructed antibodies like proteins bearing hypervariable portions of these antibodies. An identification of said common homologous sequences is also possible by using antibodies directed against the common sequence. Therefore, a discrimination between groups, subgroups, sub-subgroups and individual proteins can be made in a single experiment.

Preferably, antibodies are bound to the solid support as array and are used for the specific capture of the target's components to be identified. For HLA identification, proteins are classified in class I, II and III antigens. The class I is divided into the HLA-A, B, C, E, F and G. Each of them being subdivided into HLA types and subtypes as given in the databank IMGT/HLA. There are more than 476 different alleles of the class I HLA antigens. The heavy chains of the HLA complex of type I possess regions as the α1 and α2 domains which are very polymorphic while other parts as the α3 is more conserved (Auffray and Strominger, 1986, Advanced Hum. Genet. 15, 197). The class II is divided into the HLA-DR, HLA-DP and HLA-DQ. There are more than 430 alleles of the HLA class II. Each type is subdivided into subtypes and sub-subtypes which can be discriminated according to the present invention (example 23).

In one of the aspects of the invention, typing of Cytochrome P450 proteins is performed using the antibodies directed against cytochrome P450 1A1, 1A2, 2A6, 2C11, 3A4, 4A. These antibodies are available from ABR (Golden, Colo., U.S.A.).

According to a further aspect of the present invention, the method, kit (device) or apparatus according to the invention is advantageously used for the identification of the organisms or part of it as provided in the examples cited here above and also the ones presented in the examples 1 to 23.

Another aspect of the present invention is related to any part of biochips or microarray comprising said above described sequences (especially the specific capture nucleotide sequence described in the examples) as well as a general screening method for the identification of a target sequence specific of said microorganisms of family type discriminated from homologous sequences upon any type of microarrays or biochips by any method.

After hybridization on the array, the target sequences can be detected by current techniques. Without labeling, preferred methods are the identification of the target by mass spectrometry now adapted to the arrays (U.S. Pat. No. 5,821,060) or by intercalating agents followed by fluorescent detection(WO 97/27329).

The labeled associated detections are numerous. A review of the different labeling molecules is given in WO 97/27317. They are obtained using either already labeled primer or by incorporation of labeled nucleotides during the copy or amplification step. A labeling can also be obtained by ligating a detectable moiety onto the RNA or DNA to be tested (a labeled oligonucleotide, which is ligated, at the end of the sequence by a ligase). Fragments of RNA or DNA can also incorporate labeled nucleotides at their 5'—OH or 3'—OH ends using a kinase, a transferase or a similar enzyme.

The most frequently used labels are fluorochromes like Cy3, Cy5 and Cy7 suitable for analyzing an array by using commercially available array scanners (General Scanning, Genetic Microsystem, . . . ). Radioactive labeling, cold labeling or indirect labeling with small molecules recognized thereafter by specific ligands (streptavidin or antibodies) are common methods. The resulting signal of target fixation on the array is either fluorescent, colorimetric, diffusion, electroluminescent, bio- or chemiluminescent, magnetic, electric like impedometric or voltametric (U.S. Pat. No. 5,312,527). A preferred method is based upon the use of the gold labeling of the bound target in order to obtain a precipitate or silver staining which is then easily detected and quantified by a scanner.

Quantification has to take into account not only the hybridization yield and detection scale on the array (which is identical for target and reference sequences) but also the extraction, the amplification (or copying) and the labeling steps.

The method according to the invention may also comprise means for obtaining a quantification of target nucleotide sequences by using a standard nucleotide sequence (external or internal standard) added at known concentration. A capture nucleotide sequence is also present on the array so as to fix the standard in the same conditions as said target (possibly after amplification or copying); the method comprising the step of quantification of a signal resulting from the formation of a double stranded nucleotide sequence formed by complementary base pairing between the capture nucleotide sequences and the standard and the step of a correlation analysis of signal resulting from the formation of said double stranded nucleotide sequence with the signal resulting from the double stranded nucleotide sequence formed by complementary base pairing between capture nucleotide sequence(s) and the target in order to quantify the presence of the original nucleotide sequence to be detected and/or quantified in the biological sample.

Advantageously the standard is added in the initial biological sample or after the extraction step and is amplified or copied with the same primers and/or has a length and a GC content identical or differing from no more than 20% to the target. More preferably, the standard can be designed as a competitive internal standard having the characteristics of the internal standard found in the document WO 98/11253. Said internal standard has a part of its sequence common to the target and a specific part which is different. It also has at or near its two ends sequences which are complementary of the two primers used for amplification or copy of the target and similar GC content (WO 98/11253). In the preferred embodiment of this invention, the common part of the standard and the target, means a nucleotide sequence which is homologous to all target amplified by the same primers (i.e. which belong to the same family or organisms to be quantified).

Preferably, the hybridization yield of the standard through this specific sequence is identical or differ no more than 20% from the hybridization yield of the target sequence and quantification is obtained as described in WO 98/11253.

Said standard nucleotide sequence, external and/or internal standard, is also advantageously included in the kit (device) or apparatus according to the invention, possibly with all the media and means necessary for performing the different steps according to the invention (hybridization and culture media, polymerase and other enzymes, standard sequence(s), labeling molecule(s), etc.).

Advantageously, the solid support of the biochips also contain spots with various concentrations (i.e. 4) of labeled capture nucleotide sequences. These labeled capture nucleotide sequences are spotted from known concentrations solutions and their signals allow the conversion of the results of hybridization into absolute amounts. They also allow to test for the reproducibility of the detection.

The solid support of the biochips can be inserted in a support connected to another chamber and automatic machine through the control of liquid solution based upon the use of microfluidic technology. By being inserted into such a microlaboratory system, it can be incubated, heated, washed and labeled by automates, even for preliminary steps (like extraction of DNA, genetic amplification steps) or the identification and discrimination steps (labeling and detection). All these steps can be performed upon the same solid support.

The present invention is also related to a method to identify homologous sequences (and the groups to which they belong and eventually the organisms and their groups) possibly present in a biological sample by assay of their genetic material in a array-type format. The method is well adapted for determination of organisms belonging to several groups being themselves members of a super-group. The method is for example well adapted for a biological determination and/or classification of animals, plants, fungi or micro-organisms.

The method involves the use of multiple capture nucleotide sequences present as arrays, the capture of the corresponding target sequences and their analysis and possibly their quantification. The method also allows the identification of these organisms and their groups by characterization of the positive area of the arrays bearing the required capture nucleotide sequences. One particular specification of the invention being that a positive hybridization resulting in one spot on the array, gives the necessary information for the identification of the sequence or the organism or the group or sub-group from which it belongs by the person skilled in the art.

It also provides a method for sequential analysis of the presence of any researched organisms during the genetic amplification followed by the detection of amplicons on the array and identification of the corresponding organisms or groups thereafter.

Furthermore, the inventors have discovered that is possible to obtain by the method of the invention a very quick and easy identification of such multiple sequences belonging to several groups or sub-groups or sub-sub-groups of sequences being homologous to each others, until possible individual sequences, by combining a single nucleotide amplification, preferably by PCR, using common primer pair(s) together with an identification of the organisms at different level(s) by detecting and possibly recording upon an array having at least 5 different bound single stranded capture nucleotide sequences/cm$^2$ of solid support surface, the presence of a single signal resulting from the binding between a capture sequence and its (or their) corresponding target sequence(s) and thereafter correlating the presence of said detected target sequences to the identification of a specific genetic sequence among the other ones. The method is especially well adapted for the identification of organism species, genus and family through the analysis of a given part of their genome or gene expressed, these sequences being homologous to each other in the different organisms.

A single signal means a signal which by itself is sufficient to identify one or more target nucleotide sequence(s) to which it is designed and therefore to give (if necessary) an unambiguous response for the presence or not of the organisms or groups of organism present in the sample or the organisms or group of organisms from which said sample has been obtained.

The method and device according to the invention allows easy identification/detection of a specific nucleotide sequences among other possible amplified nucleotide sequences and possibly their quantification (characterization of the number of copies or presence of said organisms in a biological sample) of target sequences, said target nucleotide sequences having a nucleotide sequence specific of said organisms or groups of organisms.

The array may contain capture nucleotide sequences from several organism genus and from several of these genus species. The capture nucleotide sequences may detect the genus, the species and also the family(ies) to which these genus belong. The capture nucleotide sequences may also detect the sub-species and even the individual organisms of one or several species. Individual organisms of a given species are considered as having very homologous sequences differing mainly by single bases within some of their DNA sequences or genes. Homology is important for getting consensus primers and a single base change is sufficient to obtain a discrimination between two target amplicons. If not completed, the discrimination can be confirmed by the use of second capture nucleotide sequences present upon the array and able to bind a same amplicon at different sequence location.

Said identification is obtained firstly by a genetic amplification of said nucleotide sequences (target sequences) by common primer pair followed (after washing) by a discrimination between the possible different targets amplified according to the above described method.

The amplified sequences may belong to the same gene, may be part of the same DNA locus and are homologous to each others.

The method according to the invention further comprises the step of correlating the signal of detection (possibly recorded) to the presence of:
specific organism(s) groups
specific organism(s) sub-groups until the possible individuals,
genetic characteristics of a sequence from a organism,
polymorphism of said sequence,
genotyping of organisms based on differences in DNA or RNA sequences
diagnostic predisposition or evolution (monitoring) of genetic diseases, including cancer of a patient (including the human) from which the biological sample has been obtained.

The method also applies to the identification and possibly characterization of nucleotide sequences as such independently of the organism. Genes or DNA sequences can be classified in groups and sub-groups and sub-sub-groups according to their sequence homology. Bioinformatic programs exist for sequence alignment and comparison (such as Clustal, Intelligenetics, Mountain View, Calif., or GAP, BESTFIT, FASTA and TFASTA in the Wisconsin Genetics Software Package, Genetics computer Group Madison, Wis., U.S.A. or Boxshade). A classification can be made according to the percentage of homology and alignment of the sequences. An interest in detection and identification of the sequences from a given family in a given organism, tissue or cell is for example the possibility to detect the effect of any given molecules, biological or pathological conditions (by proteomics, functional genomics, etc.) upon both the overall and the specific genes of one or several families.

The inventors also find that sensitivity of the assay was increased by using high density of capture nucleotide sequences fixed on the support, being preferably higher than about 100 fmoles/cm$^2$ of solid support surface.

The capture nucleotide sequences specific for the determination of a group of organisms are designed in a way as to be able to specifically capture the different sequences belonging to the various groups. These capture nucleotide sequences are called consensus for this group of organisms. The consensus capture nucleotide sequences may contain specific sequences which are longer than the specific capture nucleotide sequences of the different members of the group. These capture nucleotide sequences are consensus sequences, (i.e. the sequences containing at each of its location the base which is the most present in the different sequences of the members of the group when aligned). In another embodiment the consensus capture nucleotide sequence has the length of the amplified sequences.

The inventors have found unexpected results in that the same identification of several organisms of several groups can be performed at the organisms as well as at the level in the same experimental conditions. Identification of the groups required long capture nucleotide sequences while the specific identification of the organism require small, but specific capture sequences. The inventors found that using the characteristic of the invention, mainly by binding of the specific part of the sequences onto a spacer, it was possible to obtain both results in the same experimental conditions; The invention allows also to use the same stringency conditions, meanly determined by the salt concentration and the temperature and the rate of reaction.

According to the invention, organisms are identified as such by their specific polymorphism. Single base substitution in a particular location of genome is the characteristic of an individual organism among others of the same species. The method for identification of the polymorphism is part of the invention with direct hybridization of the amplified sequences on the capture nucleotide sequences of the array and detection of the fixed target sequence.

The detection of the target sequence being bound on capture nucleotide sequences is obtained through the labeling of the capture nucleotide sequence on which the target sequence is bound. A step of capture nucleotide sequences labeling is added after the hybridization step. The extension of the capture nucleotide sequence free end, preferably the 3' end) is performed using detectable nucleotide, preferably a biotin or fluorescent nucleotide, and a polymerization agent, preferably a DNA polymerase and the necessary reagent for making the extension. The target sequence hybridized on the capture nucleotide sequence serves as matrix for the extension; the hybridized target sequences are then removed from the capture nucleotide sequence, rehybridized and extension of the capture nucleotide sequence performed.

The invention allows identification of the presence of a polymorphism by using an array having at least five different bounded single stranded capture polynucleotide sequence/ cm$^2$ of solid support surface, the determination of a single signal resulting from the binding between the capture sequence and the target sequence, extending at least one polynucleotide primer of the hybrid beyond the 3' terminal nucleotide thereof in the 3' 5' direction using the polynucleotide sequence as a template, said extension is effected in the presence of polymerization agent and nucleotide precursor wherein at least one nucleotide incorporated into the extended primer molecule is a detectably-modified nucleotide; denaturing the duplex to free the target sequence from the polynucleotide capture nucleotide sequence, carry out step one or more times and detecting the presence of a signal associated with the detectable modified nucleotide in the extended capture nucleotide sequence at the reaction zone to effect said determination.

The process is repeated as needed to obtain a signal detectable on the array. A preferred signal is obtained in colorimetry using the silver precipitation as proposed and detection of the array on calorimetric detector (WO 00/72018). The arrays may be present in the surface of multiwells and multiwells plate detectors used for the reading of the results.

In another embodiment, a second labeled nucleotide sequence complementary to the target sequence and adjacent to the capture nucleotide sequence is added on the hybridized amplicons and a ligation performed. If the last base of the capture nucleotide sequence is complementary to the target sequence, then ligation will occur and the spot is labeled. If not ligation will not occur even if the target amplicon is hybridized on the capture nucleotide sequence.

In a particular embodiment the array bear in separated area several identical capture nucleotide sequences differing only by one nucleotide located at the same place in the capture nucleotide sequence, the last free end is the interrogation base. The array is then able to identify the presence of any of the 4 bases present at a given location of the sequence. Such array is especially useful when detecting polymorphism in homozygote or heterozygote organism or when the polymorphism is not known.

In the method, kit (device) or apparatus according to the invention, the portion(s) (or part(ies)) of the capture nucleotide sequences complementary to the target sequence is composed of at least two families. The first one comprised between about 5 and about 60 bases, preferably between about 15 and about 40 bases and more preferably between about 20 and about 30 bases. In the second capture family, the binding parts of the capture nucleotide sequence sequences are comprised between about 10 and 1000 bases and preferably between 100 and 600 bases. These bases are preferably assigned as a continuous sequence located at or near the extremity of the capture nucleotide sequence. This sequence is considered as the specific sequence for the detection. In a preferred form of the invention, the sequence located between the specific capture nucleotide sequence and the support surface is a non-specific sequence.

In another preferred embodiment of the invention, the first family of capture nucleotide sequences detect the members of a group while the second family of capture nucleotide sequences detect the group as such.

However, both families of capture nucleotide sequences can be polynucleotides.

All the capture sequences present on the array necessary for capturing the target sequences are polynucleotides and are able to detect both the members of a group and the groups or sub-groups themselves.

The consensus primers can be chosen in order to amplify different sequences and groups of sequences.

The same pair of primers amplifies several groups of sequences being different for the different groups of homologous sequences, each one being associated with one or several group of organism.

The pair of consensus primers may be associated with group identification and/or for species identification on the array.

A second or third (or even more) primers are added for the amplification step in order to possibly amplify other sequences, related or not to one particular group and useful to be detected in the sample. Virus susceptible to be present in a clinical sample together with bacteria is one of the examples where such extension of the invention is particularly useful like the combination of virus detection of example 17 with bacteria detection of examples 7, 8 or 16.

Two pairs of (possibly consensus) primers may be used for the amplification, (one for amplification of sequences of the gram-positive and the other one for the gram-negative bacteria, the amplified sequences are specific of each of the gram-positive or the gram-negative bacteria and detected thereafter on the array as specific bacteria species or/and genus and/or family).

Each of the two primers pair amplifies various sequences specific of one or several families which are then detected as specific species or/and genus, families on the array.

The same array can also bear capture nucleotides sequences specific for bacterial families or genus.

In one preferred embodiment of the invention, the detection of the presence of any member of the groups are first detected during the PCR using method like the real time PCR and the amplicons are thereafter used for identification on the array.

Real time PCR is performed in specific machines which along the PCR cycle detect the appearance of fluorescence in the solution. Increase in fluorescence is due to the insertion of fluorochromes such as in the double stranded amplicons produced during the PCR cycles.

Specific fluorescent labeled nucleotide sequences are added to the PCR solution for specific identification of the amplicons. These nucleotide sequences are complementary to the amplified target sequences and their fluorescence emission is limited by the presence at the right position of a scavenger. (Once digested by the polymerase during the copying of the amplicons, the fluorochrome is released in solution where it is detected. Said method is called Fluorescence Resonance Emission Transfert (FRET). The sequence is chosen so as to bind to a consensus region of the detected amplicons or several nucleotide sequences are chosen in consensus regions specific of the groups of sequences or organisms to be detected. (These nucleotide sequences are preferably labeled with different fluorochromes so as to identify the group during the amplification step).

The fluorescent signal of the amplification solution is registered and if crossing a threshold, the solution is processed for hybridization on capture nucleotide sequences of the array. In a preferred embodiment a solid support bearing the array is added in the amplification chamber and in the hybridization processes. In another preferred embodiment the hybridization is performed on the surface of the same chamber as the PCR. Chambers, preferably closed chambers, can be of any size, format and material as compatible with arrays as already mentioned here above. The chambers may be in polymers such as polycarbonate, polypropylene, or glass such as capillaries. Polyacrylate based surfaces are particularly useful since they are transparent to light and allow covalent binding of capture probes necessary for the arrays. The free end, of the capture nucleotide sequence can be either a 5' or 3'—OH or phosphate group modified in order to avoid elongation. Preferably, the specific sequence portion of the capture nucleotide sequence has a melting temperature smaller than the primers used for the amplification in order to avoid hybridization during the PCR cycles. Also the hybridization may be performed at a given temperature using the heating and control system of the amplification cycler. A control process provides on the amplification cycler to continue or not the detection on the array after the amplification steps.

The real time PCR may be performed with the primers amplifying the gram-positive or/and the gram-negative PCR and thereafter the families or/and the genes or/and the species identified on the array.

One embodiment of the invention is to combine in one process the real time PCR together with the hybridization on capture probes for identification of the target molecules or organisms. In a preferred embodiment the process is performed in the same chamber and with the same machine device.

The present invention also covers the machine and apparatus necessary for performing the various steps of the process mainly for diagnostic and/or quantification of a (micro)organism or component possibly present in a sample among at least two, preferably at least 4 other related (micro)organisms which comprises:

capture molecules being bound to an insoluble solid support at specific locations according to an array, said capture molecules being able to discriminate between related (micro)organisms or components, said array having a density of at least 4 discrete regions per $cm^2$ solid support surface a detection and/or quantification device of a signal formed at the location of the binding between said target compound with said capture molecule possibly reading device of information recorded upon said solid support a computer program to recognize the discrete regions bearing the target molecules and their locations correlating the presence of the signal at these locations with the detection and/or quantification of the said (micro)organism or component in a particular embodiment, this apparatus also performs the genetic amplification of the nucleotide sequences by PCR performed previously or in real time together with the identification of a (micro)organism or its components.

Detection of other sequences can be advantageously performed on the same array (i.e. by allowing an hybridization with a standard nucleotide sequence used for the quantification, with consensus capture nucleotide sequences for the same or different micro-organisms strains, with a sequence allowing a detection of a possible antibiotic resistance gene by micro-organisms or for positive or negative control of hybridization). Said other capture nucleotide sequences have (possibly) a specific sequence longer than 10 to 60 bases and a total length as high as 600 bases and are also bound upon the insoluble solid support (preferably in the array made with the other bound capture nucleotide sequences related to the invention).

These characteristics described in details for a specific detection and analysis of nucleotide sequences can be adapted by the person skilled in the art for other components of (micro)organisms such as receptors, antibodies, enzymes, etc.

The present invention will be described in details in the following non-limiting examples in reference to the enclosed figures and tables.

Brief Description of the Tables

Table 1 presents identification of 3 gram-positive and 1 gram-negative bacteria at the genus level (horizontally) and at the species level (vertically). These bacteria are detected with the method of the invention on biochips after PCR amplification with consensus primers. The PCR was realized on the gyrase (sub-unit A) sequences.

The identification of meat animals at the family level (horizontally) and at the genus and species levels (vertically) (3 levels of classification), detected with the method of the invention on biochips after PCR amplification with consensus primers. The PCR was realized on Cytochrome B gene sequences.

Table 3 presents the identification of fishes at the family level (horizontally) and at the genus and species levels (vertically) (3 levels of classification), detected with the method of the invention on biochips after PCR amplification with consensus primers. The PCR was realized on CytochromB gene sequences.

EXAMPLES

Example 1

Detection of Homologous FemA Sequences on Array Bearing Long Specific Capture Nucleotide Sequences Production of the Capture Nucleotide Sequences and of the Targets The FemA genes corresponding to the different *Staphylococci* species were amplified separately by PCR using the following primers:

```
S. aureus 1:        5' CTTTTGCTGATCGTGATGACAAA 3'   (SEQ ID NO: 1)

S. aureus 2:        5' TTTATTTAAAATATCACGCTCTTCG 3' (SEQ ID NO: 2)

S. epidermidis 1:   5' TCGCGGTCCAGTAATAGATTATA 3'   (SEQ ID NO: 3)

S. epidermidis 2:   5' TGCATTTCCAGTTATTTCTCCC 3'    (SEQ ID NO: 4)

S. haemolyticus 1:  5' ATTGATCATGGTATTGATAGATAC 3'  (SEQ ID NO: 5)

S. haemolyticus 2:  5' TTTAATCTTTTTGAGTGTCTTATAC 3' (SEQ ID NO: 6)

S. saprophyticus 1: 5' TAAAATGAAACAACTCGGTTATAAG 3' (SEQ ID NO: 7)

S. saprophyticus 2: 5' AAACTATCCATACCATTAAGTACG 3'  (SEQ ID NO: 8)

S. hominis 1:       5' CGACCAGATAACAAAAAAGCACAA 3'  (SEQ ID NO: 9)

S. hominis 2:       5' GTAATTCGTTACCATGTTCTAA 3'    (SEQ ID NO: 10)
```

The PCR was performed in a final volume of 50 µl containing: 1.5 mM $MgCl_2$, 10 mM Tris pH 8.4, 50 mM KCl, 0.8 µM of each primer, 50 µM of each dNTP, 50 µM of biotin-16-dUTP), 1.5 U of Taq DNA polymerase Biotools, 7.5% DMSO, 5 ng of plasmid containing FemA gene. Samples were first denatured at 94° C. for 3 min. Then 40 cycles of amplification were performed consisting of 30 sec at 94° C., 30 sec at 60° C. and 30 sec at 72° C. and a final extension step of 10 min at 72° C. Water controls were used as negative controls of the amplification. The sizes of the amplicons obtained using these primers were 108 bp for *S. saprophyticus*, 139 bp for *S. aureus*, 118 bp for *S. hominis*, 101 bp for *S. epidermidis* and 128 bp for *S. haemolyticus*. The sequences of the capture nucleotide sequences were the same as the corresponding amplicons but they were single strands.

The biochips also contained positive controls which were CMV amplicons hybridized on their corresponding capture nucleotide sequence and negative controls which were capture nucleotide sequences for a HIV-I sequence on which the CMV could not bind.

Capture Nucleotide Sequence Immobilization

The protocol described by Schena et al (Proc. Natl Acad. Sci. USA 93, 10614 (1996)) was followed for the grafting of aminated DNA to aldehyde derivatized glass. The aminated capture nucleotide sequences were spotted from solutions at concentrations ranging from 150 to 3000 nM. The capture nucleotide sequences were printed onto the silylated microscopic slides with a home made robotic device (250 µm pins from Genetix (UK) and silylated (aldehyde) microscope slides from Cell associates (Houston, USA)). The spots have 400 µm in diameter and the volume dispensed is about 0.5 nl. Slides were dried at room temperature and stored at 4° C. until used.

Hybridization

At 65 µl of hybridization solution (AAT, Namur, Belgium) were added 5 µl of amplicons and the solution was loaded on the array framed by an hybridization chamber. For positive controls we added 2 nM biotinylated CMV amplicons of 437 bp to the solution; their corresponding capture nucleotide sequences were spotted on the array. The chamber was closed with a coverslip and slides were denatured at 95° C. for 5 min. The hybridization was carried out at 600 for 2 h. Samples were washed 4 times with a washing buffer.

Colorimetric Detection

The glass samples were incubated 45 min at room temperature with 800 µl of streptavidin labeled with colloidal gold 1000× diluted in blocking buffer (Maleic buffer 100 mM pH 7.5, NaCl 150 mM, Gloria milk powder 0.1%). After 5 washes with washing buffer, the presence of gold served for catalysis of silver reduction using a staining revelation solution (AAT, Namur, Belgium). The slides were incubated 3 times 10 min with 800 µl of revelation mixture, then rinsed with water, dried and analyzed using a microarray reader. Each slides were then quantified by a specific quantification software.

Fluorescence Detection

The glass samples were incubated 45 min at room temperature with 800 µl of Cyanin 3 or Cyanin 5 labeled streptavidin. After washing, the slides were dried before being stored at room temperature. The detection was performed in the array-scanner GSM 418 (Genetic Microsystem, Woburn, Mass., U.S.A.) Each slide was then quantified by a specific quantification software.

The results give a cross-reaction between the species. For example, epidermidis amplicons hybridized on its capture nucleotide sequence give a value of 152, but give a value of 144, 9, 13 and 20 respectively for the *S. saprophyticus, S. aureus, S. haemolyticus* and *S. hominis* capture nucleotide sequences.

Example 2

Detection of Homologous FemA Sequences on Array Bearing Small Specific Capture Nucleotide Sequences Protocols for capture nucleotide sequences immobilization and silver staining detection were described in example 1 but the capture nucleotide sequences specific of the 5 *Staphylococcus* species were spotted at concentrations of 600 nM and are the following:

| Name Capture nucleotide sequence | Sequence (5'->3') | |
|---|---|---|
| ATaur02 | ATTTAAAATATCACGCTCTTCGTTTAG | (SEQ ID NO: 11) |
| ATepi02 | ATTAAGCACATTTCTTTCATTATTTAG | (SEQ ID NO: 12) |
| AThae02 | ATTTAAAGTTTCACGTTCATTTTGTAA | (SEQ ID NO: 13) |
| AThom02 | ATTTAATGTCTGACGTTCTGCATGAAG | (SEQ ID NO: 14) |
| ATsap02 | ACTTAATACTTCGCGTTCAGCCTTTAA | (SEQ ID NO: 15) |

In this case, the targets are fragments of the FemA gene sequence corresponding to the different *Staphylococci* species which were amplified by a PCR using the following consensus primers:

```
APstap03:
5' CCCACTCGCTTATATAGAATTTGA 3'    (SEQ ID NO: 16)

APstap04:
5' CCACTAGCGTACATCAATTTTGA 3'     (SEQ ID NO: 17)

APstap05:
5' GGTTTAATAAAGTCACCAACATATT 3'   (SEQ ID NO: 18)
```

This PCR was performed in a final volume of 100 µl containing: 3 mM MgCl$_2$, 1 mM Tris pH 8, 1 µM of each primer, 200 µM of dATP, dCTP and dGTP, 150 µM of dTTP, 50 µM of biotin-16-dUTP, 2.5 U of Taq DNA polymerase (Boehringer Mannheim, Allemagne), 1 U of Uracil-DNA-glycosylase heat labile (Boehringer Mannheim, Allemagne), 1 ng of plasmid containing FemA gene. Samples were first denatured at 94° C. for 5 min. Then 40 cycles of amplification were performed consisting of 1 min at 94° C., 1 min at 50° C. and 1 min at 72° C. and a final extension step of 10 min at 72° C. Water controls were used as negative controls of the amplification. The sizes of the amplicons obtained using these primers were 489 bp for all species.

The hybridization solution was prepared as in example 1 and loaded on the slides. Slides were denatured at 98° C. for 5 min. Hybridization are carried out at 50° C. for 2 h. Samples are then washed 4 times with a washing buffer. The values were very low and almost undetectable.

Example 3

Effect of the Spacer Length on the Sensitivity of Detection of Homologous FemA Sequences on Array Bearing Long Capture Nucleotide Sequences with a Small Specific Sequence The experiment was conducted as described in example 2 with the same amplicons but the capture nucleotide sequences used are the following:

| Name Capture nucleotide sequence | Sequence (5'->3') | |
|---|---|---|
| Ataur02 | ATTTAAAATATCACGCTCTTCGTTTAG | (SEQ ID NO: 11) |
| ATepi02 | ATTAAGCACATTTCTTTCATTATTTAG | (SEQ ID NO: 12) |
| ATepi03 | GAATTCAAAGTTGCTGAGAAATTAAGCACATTTCTTTCATTATTTAG | (SEQ ID NO: 19) |

-continued

| Name Capture nucleotide sequence | Sequence (5'->3') | |
|---|---|---|
| ATepi04 | <u>GAATTCAAAGTTGCTGAGAATAGTTCAATGGAAGGAAGC</u>GATTAAGCACATTTCTTTCATTATTTAG | (SEQ ID NO: 20) |
| ATepi05 | <u>GAATTCAAAGTTGCTGAGAATAGTTCAATGGAAGGAAGCGTCTTCTTAAAATCTAAAGAA</u>ATTAAGCACATTTCTTTCATTATTTAG | (SEQ ID NO: 21) |

[a]The spacer sequences are underlined

The target amplicons were 489 bp long while the capture nucleotide sequences were 47, 67 or 87 bases single stranded DNA with a specific sequence of 27 bases.

Example 4

Specificity of the Detection of FemA Sequences from Different Bacterial Species on the Same Array Bearing Long Capture Nucleotide Sequences with a Small Specific Sequence The experiment was conducted as described in example 2 but the capture nucleotide sequences were spotted at concentrations of 3000 nM and are the following:

A consensus sequence is present on the biochips which detects all the tested *Staphylococcus* species. All target sequences were amplified by PCR with the same pair of primers.

The size of the amplicons obtained using these primers were 587 bp for all species. The consensus sequence capture nucleotide sequence was a 489 base long single stranded DNA complementary to the amplicons of *S. hominis* as amplified in example 2. The detection was made in fluorescence. Homology between the consensus capture nucleotide sequence and the sequences of the FemA from the 15 S. species were between 66 and 85%. All the sequences hybridized on this consensus capture nucleotide sequence.

| Name Capture nucleotide sequence | Sequence (5'->3') | |
|---|---|---|
| Ataur27 | <u>GAATTCAAAGTTGCTGAGAATAGTTCAATGGAAGGAAGCG</u>ATTTAAAATATCACGCTCTTCGTTTAG | (SEQ ID NO: 22) |
| Atepi27 | <u>GAATTCAAAGTTGCTGAGAATAGTTCAATGGAAGGAAGCG</u>ATTAAGCACATTTCTTTCATTATTTAG | (SEQ ID NO: 23) |
| Athae27 | <u>GAATTCAAAGTTGCTGAGAATAGTTCAATGGAAGGAAGCG</u>ATTTAAAGTTTCACGTTCATTTTGTAA | (SEQ ID NO: 24) |
| Athom27 | <u>GAATTCAAAGTTGCTGAGAATAGTTCAATGGAAGGAAGCG</u>ATTTAATGTCTGACGTTCTGCATGAAG | (SEQ ID NO: 25) |
| Atsap27 | <u>GAATTCAAAGTTGCTGAGAATAGTTCAATGGAAGGAAGCG</u>ACTTAATACTTCGCGTTCAGCCTTTAA | (SEQ ID NO: 26) |

[a]The spacer sequences are underlined. The specific sequences were of 27 bases

The targets are fragments of the FemA gene sequence corresponding to the different *Staphylococci* species which were amplified by PCR using the following consensus primers:

```
APcons3-1:
5' TAAYAAARTCACCAACATAYTC 3'   (SEQ ID NO: 27)

APcons3-2:
5' TYMGNTCATTTATGGAAGATAC 3'   (SEQ ID NO: 28)
```

Example 5

Effect of the Length of the Specific Sequence of the Capture Nucleotide Sequence on the Discrimination Between Homologous Sequences The experiment was conducted as described in example 4 but at a temperature of 43° C. and the capture nucleotide sequences used are presented in the table here joined. The numbers after the names indicate the length of the specific sequences.

The FemA amplicons of *S. anaerobius* (a subspecies of *S. aureus*) were hybridized on an array bearing capture nucleotide sequences of 67 single stranded bases with either 15, 27 and 40 bases specific for the *S. aureus, anaerobius* and *epidermidis* at their extremities. The difference between the capture nucleotide sequences of *anaerobius* and *aureus* was only one base in the 15 base capture nucleotide sequence and 2 in the 27 and the 40 bases.

The amplicons of the FemA from the three *Staphylococcus* species were hybridized on the array.

| Name Capture nucleotide sequence | Sequence (5'->3') | |
|---|---|---|
| Ataur15 | GAATTCAAAGTTGCTGAGAATAGTTCAATGGAAGGAAGCGTCTTCT TAAAATGCTCTTCGTTTAGTT | (SEQ ID NO: 29) |
| Ataur27 | GAATTCAAAGTTGCTGAGAATAGTTCAATGGAAGGAAGCGATTTAA AATATCGCTCTTCGTTTAG | (SEQ ID NO: 22) |
| Ataur40 | GAATTCAAAGTTGCTGAGAATAGTTCAAATCTTTATTTAAAATATCA CGCTCTTCGTTTAGTTCTTT | (SEQ ID NO: 30) |
| Atana15 | GAATTCAAAGTTGCTGAGAATAGTTCAATGGAAGGAAGCGTCTTCT TAAAATGCTCTTCATTTAGTT | (SEQ ID NO: 31) |
| Atana27 | GAATTCAAAGTTGCTGAGAATAGTTCAATGGAAGGAAGCGGTTTAA AATAGTCACGCTCTTCATTTAG | (SEQ ID NO: 32) |
| Atana40 | GAATTCAAAGTTGCTGAGAATAGTTCAAATCTTTGTTTAAAATATCA CGCTCTTCATTTAGTTCTTT | (SEQ ID NO: 33) |
| Atepi15 | GAATTCAAAGTTGCTGAGAATAGTTCAATGGAAGGAAGCGTCTTCT TAAAATTTTCATTATTTAGTT | (SEQ ID NO: 34) |
| Atepi27 | GAATTCAAAGTTGCTGAGAATAGTTCAATGGAAGGAAGCGATTAAG CACATTTCTTTCATTATTTAG | (SEQ ID NO: 23) |
| Atepi40 | GAATTCAAAGTTGCTGAGAATAGTTCAAATCTTTATTAAGCACATTT CTTTCATTATTTAGTTCCTC | (SEQ ID NO: 35) |

Example 6

Sensitivity of the Detection of FemA Sequences of *Staphylococcus aureus* on Arrays Bearing Specific Sequence as Proposed by this Invention and the Consensus Sequence The experiment was conducted as described in example 4 with the capture nucleotide sequences spotted at concentrations of 3000 nM. The bacterial FemA sequences were serially diluted before the PCR and being incubated with the arrays.

Example 7

Detection of 16 Homologous FemA Sequences on Array

The consensus primers and the amplicons were the same as described in the example 4 but the capture probes were chosen for the identification of 15 *Staphylococcus* species. The experiment is conducted as in example 4. The capture nucleotide sequences contain a spacer fixed on the support by its 5' end and of the following sequence 5' GAAT-TCAAAGTTGCTGAGAATAGTTCAATG-GAAGGAAGCG 3' (SEQ ID NO: 36) followed by the following specific sequences for the various femA from the different *Staphylococcus*.

*S. aureus:*
ATTTAAAATATCACGCTCTTCGTTTAG    (SEQ ID NO: 37)

*S. epidermidis:*
ATTAAGCACATTTCTTTCATTATTTAG    (SEQ ID NO: 38)

-continued

*S. haemolyticus:*
ATTTAAAGTTTCACGTTCATTTTGTAA    (SEQ ID NO: 39)

*S. hominis:*
ATTTAATGTCTGACGTTCTGCATGAAG    (SEQ ID NO: 40)

*S. saprophyticus:*
ACTTAATACTTCGCGTTCAGCCTTTAA    (SEQ ID NO: 41)

*S. capitis:*
ATTAAGAACATCTCTTTCATTATTAAG    (SEQ ID NO: 42)

*S. caseolyticus:*
ATAAAGACATTCGAGACGAAGGCT       (SEQ ID NO: 43)

*S. cohnii:*
ACTTAACACTTCACGCTCTGACTTGAG    (SEQ ID NO: 44)

*S. gallinarum:*
ACTTAAAACTTCACGTTCAGCAGTAAG    (SEQ ID NO: 45)

*S. intermedius:*
GTGGAAATCTTGCTCTTCAGATTTCAG    (SEQ ID NO: 46)

*S. lugdunensis:*
TTCTAAAGTTTGTCGTTCATTCGTTAG    (SEQ ID NO: 47)

*S. schleiferi:*
TTTAAAGTCTTGCGCTTCAGTGTTGAG    (SEQ ID NO: 48)

*S. sciuri:*
GTTGTATTGTTCATGTTCTTTTTCTAA    (SEQ ID NO: 49)

-continued

```
S. simulans:
TTCTAAATTCTTTTGTTCAGCGTTCAA        (SEQ ID NO: 50)

S. warneri:
AGTTAAGGTTTCTTTTTCATTATTGAG        (SEQ ID NO: 51)

S. xylosus:
GCTTAACACCTCACGTTGAGCTTGCAA        (SEQ ID NO: 52)
```

Example 8

Detection of 13 Homologous p34 Sequences and Identification of 13 *Mycobacteria* species The P34 genes present in all *Mycobacteria* were all amplified with the following consensus primers:

Sense
MycU4 5' CATGCAGTGAATTAGAACGT 3' (SEQ ID NO: 53) located at the position 496–515 of the gene, Tm=56° C.

Antisense
APmcon02 5' GTASGTCATRRSTYCTCC 3' (SEQ ID NO: 54) located at the position 733–750 of the gene, Tm=52–58° C.
   S=C or G
   R=A or G
   Y=T or C The size of amplified products ranges from 123 to 258 bp.

The following capture nucleotide sequences were chosen for the specific capture of the *Mycobacteria* sequences:

Each of the sequences above comprises a spacer at its 5' end. Spacer sequence: 5' GAATTCAAAGTTGCT-GAGAATAGTTCAATGGAAGGAAGCGTCTTC 3' (SEQ ID NO: 74). Capture nucleotide sequences were aminated at their 5' end.

Example 9

Detection of MAGE Genes

MAGE genes were all amplified with the following consensus primers:

Sense
DPSCONS2 5' GGGCTCCAGCAGCCAAGAAGAGGA 3' (SEQ ID NO: 75), located at the 398–421 position of the gene
Tm=78° C.

Other amplicons were added as sense primer in order to increase the efficiency of the PCR for some MAGEs:
DPSMAGE1 5' GGGTTCCAGCAGCCGTGAAGAGGA 3' (SEQ ID NO: 76)
Tm=78° C.
DPSMAG8 5' GGGTTCCAGCAGCAATGAAGAGGA 3' (SEQ ID NO: 77)
Tm=74° C.
DPSMAG12 5' GGGCTCCAGCAACGAAGAACAGGA 3' (SEQ ID NO: 78)
Tm=76° C.

Antisense
DPASCONB4 5' CGGTACTCCAGGTAGTTTTCCTGC 3' (SEQ ID NO: 79), located at the position 913–936 of the gene, Tm=74° C.

```
Capture nucleotide sequences
M. avium:              5' CGGTCGTCTCCGAAGCCCGCG 3'        (21 nt) (SEQ ID NO: 55)

M. gastrii 1:          5' GATCGGCAGCGGTGCCGGGG 3'         (20 nt) (SEQ ID NO: 56)

M. gastrii 3:          5' GTATCGCGGGCGGCAAGGT 3'          (19 nt) (SEQ ID NO: 57)

M. gastrii 5:          5' TCTGCCGATCGGCAGCGGTGCCGG 3'     (24 nt) (SEQ ID NO: 58)

M. gastrii 7:          5' GCCGGGGCCGGTATTCGCGGGCGG 3'     (24 nt) (SEQ ID NO: 59)

M. gordonae:           5' GACGGGCACTAGTTGTCAGAGG 3'       (22 nt) (SEQ ID NO: 60)

M. intracellulare 1:   5' GGGCCGCCGGGGGCCTCGCCG 3'        (21 nt) (SEQ ID NO: 61)

M. intracellulare 3:   5' GCCTCGCCGCCCAAGACAGTG 3'        (21 nt) (SEQ ID NO: 62)

M. leprae:             5' GATTTCGGCGTCCATCGGTGGT 3'       (22 nt) (SEQ ID NO: 63)

M. kansasi 1:          5' GATCGTCGGCAGTGGTGACGG 3'        (21 nt) (SEQ ID NO: 64)

M. kansasi 3:          5' TCGTCGGCAGTGGTGAC 3'            (17 nt) (SEQ ID NO: 65)

M. kansasi 5:          5' ATCCGCCGATCGTCGGCAGTGGTGACG 3'  (27 nt) (SEQ ID NO: 66)

M. malmoense:          5' GACCCACAACACTGGTCGGCG 3'        (21 nt) (SEQ ID NO: 67)

M. marinum:            5' CGGAGGTGATGGCGCTGGTCG 3'        (21 nt) (SEQ ID NO: 68)

M. scrofulaceum:       5' CGGCGGCACGGATCGGCGTC            (20 nt) (SEQ ID NO: 69)

M. simiac:             5' ATCGCTCCTGGTCGCGCCTA 3'         (20 nt) (SEQ ID NO: 70)

M. szulgai:            5' CCCGGCGCGACCAGCAGAACG 3'        (21 nt) (SEQ ID NO: 71)

M. tuberculosis:       5' GCCGTCCAGTCGTTAATGTCGC 3'       (22 nt) (SEQ ID NO: 72)

M. xenopi:             5' CGGTAGAAGCTGCGATGACACG 3'       (22 nt) (SEQ ID NO: 73)
```

The size of the amplified products are around 530 bp.
The following capture nucleotide sequences of 27 nucleotides were chosen for the specific capture of the MAGE sequences:

```
Capture nucleotide sequences
Mage 1 DTAS01
5' ACAAGGACTCCAGGATACAAGAGGTGC 3'    (SEQ ID NO: 80)

Mage 2 DTAS02
5' ACTCGGACTCCAGGTCGGGAAACATTC 3'    (SEQ ID NO: 81)

Mage 3 DTS0306
5' AAGACAGTATCTTGGGGGATCCCAAGA 3'    (SEQ ID NO: 82)

Mage 4 DTAS04
5' TCGGAACAAGGACTCTGCGTCAGGCGA 3'    (SEQ ID NO: 83)

Mage 5 DTAS05
5' GCTCGGAACACAGACTCTGGGTCAGGG 3'    (SEQ ID NO: 84)

Mage 6 DTS06
5' CAAGACAGGCTTCCTGATAATCATCCT 3'    (SEQ ID NO: 85)

Mage 7 DTAS07
5' AGGACGCCAGGTGAGCGGGGTGTGTCT 3'    (SEQ ID NO: 86)

Mage 8 DTAS08
5' GGGACTCCAGGTGAGCTGGGTCCGGGG 3'    (SEQ ID NO: 87)

Mage 9 DTAS09
5' TGAACTCCAGCTGAGCTGGGTCGACCG 3'    (SEQ ID NO: 88)

Mage 10 DTAS10
5' TGGGTAAAGACTCACTGTCTGGCAGGA 3'    (SEQ ID NO: 89)

Mage 11 DTAS11
5' GAAAAGGACTCAGGGTCTATCAGGTCA 3'    (SEQ ID NO: 90)

Mage 12 DTAS12
5' GTGCTACTTGGAAGCTCGTCTCCAGGT 3'    (SEQ ID NO: 91)
```

Each of the sequences above comprises a spacer aminated at its 5' end in order to be covalently linked to the glass. Spacer sequence 5' GAATTCAAAGTTGCTGAGAATAGTTCAATGGAAGGAAGCG 3' (SEQ ID NO: 36)

They were spotted on aldehyde bearing glasses and used for the detection of the MAGEs amplified by the consensus primers given here above. The results showed a non equivocal identification of the MAGEs present in the tumors compared to identification using 12 specific PCR, one for each MAGE sequences.

Example 10

Identification of G-protein Dopamine Receptors Subtypes in Rat

Dopamine Receptor coupled to the G-protein were all amplified with the following consensus primers:

Sense
CONSENSUS2-3-4
    5' TGCAGACMACCACCAACTACTT 3' (SEQ ID NO: 92) located at the position 221–242 of the gene, Tm=66° C.
    M=A or C
CONSENSUS1-5
    5' TGMGGKCCAAGATGACCAACWT 3' (SEQ ID NO: 93) (22 nt) located at the position 221–240 of the gene, Tm=66° C.
    M=A or C
    K=G or T
    W=A or T Antisense
    5' TCATGRCRCASAGGTTCAGGAT 3' (SEQ ID NO: 94) located at the position 395–416 of the gene, Tm=64–68° C.
    R=A or G
    S=C or G The size of the amplified product is 196 bp.
The following capture nucleotide sequences of 27 nucleotides were chosen for the specific capture of the dopamine receptor sequences:

```
Capture nucleotide sequences
DRD1
5' CTGGCTTTTGGCCTTTGGGTCCCTTTT 3'    (SEQ ID NO: 95)

DRD2
5' TGATTGGAAATTCAGCAGGATTCACTG 3'    (SEQ ID NO: 96)

DRD3
5' GAGTCTGGAATTTCAGCCGCATTTGCT 3'    (SEQ ID NO: 97)

DRD4
5' CGTCTGGCTGCTGAGCCCCCGCCTCTG 3'    (SEQ ID NO: 98)

DRD5
5' CTGGGTACTGGCCCTTTGGGACATTCT 3'    (SEQ ID NO: 99)
```

Each of the sequences above comprised an aminated spacer at its 5' end. Spacer sequence 5' GAATTCAAAGTTGCTGAGAATAGTTCAATGGAAGGAAGCG (SEQ ID NO: 36).

Example 11

Identification of G-protein Histamine Receptors Subtypes in Rat

Histamine Receptor coupled to the G-protein were all amplified with the following primers:

Sense
H1sense
    5' CTCCGTCCAGCAACCCCT 3' (SEQ ID NO: 100) (18 nt) located at the Position 381–398 of the gene, Tm=60° C.
H2sense
    5' CTGTGCTGGTCACCCCAGT 3' (SEQ ID NO: 101) (19 nt) located at the Position 380–398 of the gene, Tm=62° C.
H3sense
    5' ACTCATCAGCTATGACCGATT 3' (SEQ ID NO: 102) (21 nt) located at the Position
    378–398 of the gene, Tm=60° C.

Antisense
H1antisense
    5' ACCTTCCTTGGTATCGTCTG 3' (SEQ ID NO: 103) (20 nt) located at the Position 722–741 of the gene, Tm=60° C.
H2antisense
    5' GAAACCAGCAGATGATGAACG 3' (SEQ ID NO: 104) (21 nt) located at the Position 722–742 of the gene, Tm=62° C.
H3antisense
    5' GCATCTGGTGGGGGTTCTG 3' (SEQ ID NO: 105) (19 nt) located at the Position 722–740 of the gene, Tm=62° C.

Size of the amplified product ranged from 359 to 364 bp.
The following capture nucleotide sequences were chosen for the specific capture of the histamine receptor sequences:

Capture Nucleotide Sequences

```
                                    (SEQ ID NO: 106)
H1   5' CCCCAGGATGGTAGCGGA 3'            (18 nt)

(SEQ ID NO: 107)
H2   5' AGGATAGGGTGATAGAAATAAC 3'        (22 nt)

(SEQ ID NO: 108)
H3   5' TCTCGTGTCCCCCTGCTG 3'            (18 nt)
```

Each of the sequences above comprised a spacer at its 5' end.

Spacer sequence 5' GAATTCAAAGTTGCTGAGAATAGTTCAATGGAAGGAAGCG 3' (SEQ ID NO: 36). Capture nucleotide sequences were aminated at their 5' end.

Example 12

Identification of G-protein Serotonin Receptors Subtypes in Rat

Serotonin Receptor coupled to the G-protein were all amplified with the following primers:
Sense
Consensus for the subtypes 1A, 1B, 1C, 1D, 1E, 2A, 2B, 2C, 4, 6, 7
5' ATCHTGCACCTSTGBGBCAT 3' (SEQ ID NO: 109)
Tm=58–64° C. (20 nt)
  H=C or A or T
  S=C or G
  B=C or T or G
  1A ATCCTGCACCTGTGCGCCAT (0 mismatch) position 370–389 (SEQ ID NO: 110)
  1B ATCATGCATCTCTGTGTCAT (1 mismatch) position 397–416 (SEQ ID NO: 111)
  1C ATCATGCACCTCTGCGCCAT (0 mismatch) position 427–446 (SEQ ID NO: 112)
  1D ATCCTGCATCTCTGTGTCAT (1 mismatch) position 367–386 (SEQ ID NO: 113)
  1E ATCTTGCACCTGTCGGCTAT (2 mismatches) position 331–350 (SEQ ID NO: 114)
  2A ATCATGCACCTCTGCGCCAT (0 mismatch) position 487–506 (SEQ ID NO: 115)
  2B ATCATGCATCTCTGTGCCAT (1 mismatch) position 424–443 (SEQ ID NO: 116)
  2C ATCATGCACCTCTGCGCCAT (0 mismatch) position 24–43 (SEQ ID NO: 117)
  4 ATTTTTCACCTCTGCTGCAT (3 mismatches) (SEQ ID NO: 118)
  6 ATCCTCAACCTCTGCTTCAT (3 mismatches) (SEQ ID NO: 119)
  7 ATCATGACCCTGTGCGTGAT (3 mismatches) (SEQ ID NO: 120)
Consensus 4, 6
5' ATCYTYCACCTCTGCYKCAT 3' (SEQ ID NO: 121)
Tm=52–64° C. (20 nt)
  K=G or T
  Y=T or C
  4 ATTTTTCACCTCTGCTGCAT (SEQ ID NO: 122) (1 mismatch) position 322–341
  6 ATCCTCAACCTCTGCCTCAT (SEQ ID NO: 123) (1 mismatch) position 340–359
Consensus 5A, 5B
5' ATCTGGAAYGTGRCAGCCAT3' (SEQ ID NO: 124)
Tm=58–62° C. (20 nt)
  Y=T or C
  R=A or G
  5A ATCTGGAATGTGACAGCAAT (SEQ ID NO: 125) (1 mismatch) position 385–404
  5B ATCTGGAACGTGGCGGCCAT (SEQ ID NO: 126) (1 mismatch) position 424–443

Specific 7
  5' ATCATGACCCTGTGCGTGAT 3' (SEQ ID NO: 127)
  Tm=56° C. (18 nt) position 517–536
Specific 3B
  5' CTTCCGGAACGATTAGAAA3' (SEQ ID NO: 128)
  Tm=54° C. (19 nt) position 404–422

Antisense
Consensus for the subtypes 1A, 1B, 1C, 1D, 1E, 2A, 2B, 2C, 4, 7 Tm=48–58° C.
5' TTGGHNGCYTTCYGBTC 3' (SEQ ID NO: 129)
  Y=T or C
  H=A or T or C
  N=A or C or G or T
  B=C or T or G
  1A TTCACCGTCTTCCTTTC (4 mismatches) (SEQ ID NO: 130)
  1B TTGGTGGCTTTGCGCTC (1 mismatch) position 913–929 (SEQ ID NO: 131)
  1C TTGGAAGCTTTCTTTTC (1 mismatch) position 922–938 (SEQ ID NO: 132)
  1D TTAGTGGCTTTCCTTTC (2 mismatches) position 877–893 (SEQ ID NO: 133)
  1E GTGGCTGCTTTGCGTTC (2 mismatches) position 862–878 (SEQ ID NO: 134)
  2A TTGCACGCCTTTTGCTC (2 mismatches) position 952–968 (SEQ ID NO: 135)
  2B TTTGAGGCTCTCTGTTC (2 mismatches) position 952–968 (SEQ ID NO: 136)
  2C TTGGAAGCTTTCTTTTC (1 mismatch) position 424–440 (SEQ ID NO: 137)
  4 TTGGCTGCTTTCCGGTC (2 mismatches) (SEQ ID NO: 138)
  7 GTGGCTGCTTTCTGTTC (1 mismatch) position 973–989 (SEQ ID NO: 139)
Specific 1A
  5' TTCACCGTCTTCCTTTC 3' (SEQ ID NO: 140)
  Tm=50° C. (17 nt) position 1018–1034
Specific 4
  5' TCTTGGCTGCTTTGGTC 3' (SEQ ID NO: 141)
  Tm=52° C. (17 nt) position 762–778
Specific 6
  5' ATAAAGAGCGGGTAGATG 3' (SEQ ID NO: 142)
  Tm=52° C. (18 nt) position 945–963
Consensus 5A, 5B
  5' CCTTCTGCTCCCTCCA 3' (SEQ ID NO: 143)
  Tm=52° C. (16 nt)
  5A CCTTCTGTTCCCTCCA (1 mismatch) position 823–840 (SEQ ID NO: 144)
  5B CCTTCTGCTCCCGCCA (1 mismatch) position 862–879 (SEQ ID NO: 145)
Specific 3B
  5' ACCGGGGACTCTGTGT 3' (SEQ ID NO: 146)
  Tm=52° C. (16 nt) position 1072–1089

The following capture nucleotide sequences were chosen for the specific capture of the serotonin receptor subtypes sequences:

Capture Nucleotide Sequences
  HTR1C 5' CTATGCTCAATAGGATTACGT 3' (21 nt) (SEQ ID NO: 147)
  HTR2A 5' GTGGTGAATGGGGTTCTGG 3' (19 nt) (SEQ ID NO: 148)
  HTR2B 5' TGGCCTGAATTGGCTTTTGA 3' (21 nt) (SEQ ID NO: 149)
  HTR2C/1C 5' TTATTCACGAACACTTTGCTTT 3' (22 nt) (SEQ ID NO: 150)

HTR1B 5' AATAGTCCACCGCATCAGTG 3' (20 nt) (SEQ ID NO: 151)
HTR1D 5' GTACTCCAGGGCATCGGTG 3' (19 nt) (SEQ ID NO: 152)
HTR1A 5' CATAGTCTATAGGGTCGGTG 3' (20 nt) (SEQ ID NO: 153)
HTR1E 5' ATACTCGACTGCGTCTGTGA 3' (20 nt) (SEQ ID NO: 154)
HTR7 5' GTACGTGAGGGGTCTCGTG 3' (19 nt) (SEQ ID NO: 155)
HTR5A 5' GGCGCGTTATTGACCAGTA 3' (19 nt) (SEQ ID NO: 156)
HTR5B 5' GGCGCGTGATAGTCCAGT 3' (18 nt) (SEQ ID NO: 157)
HTR3B 5' GATATCAAAGGGGAAAGCGTA 3' (21 nt) (SEQ ID NO: 158)
HTR4 5' AAACCAAAGGTTGACAGCAG 3' (20 nt) (SEQ ID NO: 159)
HTR6 5' GTAGCGCAGCGGCGAGAG 3' (18 nt) (SEQ ID NO: 160)

Each of the sequences above comprises a spacer at its 5' end

Spacer sequence 5' GAATTCAAAGTTGCTGAGAATAGTTCAATGGAAGGAAGCG 3' (SEQ ID NO: 36). Capture nucleotide sequences were aminated at their 5' end.

Example 13

Identification of the HLA-A Subtypes

The HLA-A subtypes were amplified with the following consensus primers:

Sense
  IPSCONA 5' GACAGCGACGCCGCGAGCCA 3' (SEQ ID NO: 161) located at the position 181–200 of the gene, Tm=70° C.

Antisense
  IPASCONA 5 CGTGTCCTGGGTCTGGTCCTCC 3' (SEQ ID NO: 162) located at the position 735–754 of the gene, Tm=74° C.

The size of the amplified product was 574 bp.

The following capture nucleotide sequences of 27 nucleotides were chosen for the specific capture of the HLA-A sequences:

```
Capture nucleotide sequences
HLA-A1   ITSA01    5' GGAGGGCCGGTGCGTGGACGGGCTCCG 3'  (SEQ ID NO: 163)
HLA-A2   ITASA02   5' TCTCCCCGTCCCAATACTCCGGACCCT 3'  (SEQ ID NO: 164)
HLA-A3   ITASA03A  5' CTGGGCCTTCACATTCCGTGTCTCCTG 3'  (SEQ ID NO: 165)
         ITSA03B   5' AGCGCAAGTGGGAGGCGGCCCATGAGG 3'  (SEQ ID NO: 166)
HLA-A11  ITSA11A   5' GCCCATGCGGCGGAGCAGCAGAGAGCC 3'  (SEQ ID NO: 167)
         ITSA11B   5' CCTGGAGGGCCGGTGCGTGGAGTGGCT 3'  (SEQ ID NO: 168)
HLA-A23  ITSA23A   5' GCCCGTGTGGCGGAGCAGTTGAGAGCC 3'  (SEQ ID NO: 169)
         ITASA23B  5' CCTTCACTTTCCCTGTCTCCTCGTCCC 3'  (SEQ ID NO: 170)
HLA-A24  ITSA24A   5' GCCCATGTGGCGGAGCAGCAGAGAGCC 3'  (SEQ ID NO: 171)
         ITASA24B  5' TAGCGGAGCGCGATCCGCAGGTTCTCT 3'  (SEQ ID NO: 172)
HLA-A25  ITASA25A  5' TAGCGGAGCGCGATCCGCAGGCTCTCT 3'  (SEQ ID NO: 173)
         ITASA25B  5' TCACATTCCGTGTGTTCCGGTCCCAAT 3'  (SEQ ID NO: 174)
HLA-A26  ITASA26   5' GGGTCCCCAGGTTCGCTCGGTCAGTCT 3'  (SEQ ID NO: 175)
HLA-A29  ITASA29   5' TCACATTCCGTGTCTGCAGGTCCCAAT 3'  (SEQ ID NO: 176)
HLA-A30  ITASA30   5' CGTAGGCGTGCTGTTCATACCCGCGGA 3'  (SEQ ID NO: 177)
HLA-A31  ITASA31   5' CCCAATACTCAGGCCTCTCCTGCTCTA 3'  (SEQ ID NO: 178)
HLA-A33  IT5A33    5' CGCACGGACCCCCCCAGGACGCATATG 3'  (SEQ ID NO: 179)
HLA-A68  ITSA68A   5' GGCGGCCCATGTGGCGGAGCAGTGGAG 3'  (SEQ ID NO: 180)
         ITASA68B  5' GTCGTAGGCGTCCTGCCGGTACCCGCG 3'  (SEQ ID NO: 181)
HLA-A69  ITASA69   5' ATCCTCTGGACGGTGTGAGAACCGGCC 3'  (SEQ ID NO: 182)
```

Each of the sequences above comprised an aminated spacer at its 5' end. Spacer sequence 5' GAATTCAAAGTTGCTGAGAATAGTTCAATGGAAGGAAGCG 3' (SEQ ID NO: 36)

Example 14

Identification of Cytochrome P450 3a Forms

The Cytochrome P450 forms were amplified with the following consensus primers:

Sense
Consensus
  5' GCCAGAGCCTGAGGA 3' (SEQ ID NO: 183) located at the position 1297–1311 of the 3a3 gene, Tm50° C.

Antisense
Consensus a3, a23, a1, a2
  5' TCAAAAGAAATTAACAGAGA 3' (SEQ ID NO: 184) located at the position 1839–1858 of the 3a3 gene, Tm=50° C.
Specific a9
  5' ACAATGAAGGTAACATAGG 3' (SEQ ID NO: 185) located at the position 2015–2033 of the 3a9 gene Tm=52° C.
Specific a18
  5' ACTGATGGAACTAACTGG 3' (SEQ ID NO: 186) located at the position 1830–1846 of the 3a18 gene Tm=52° C.

The length of the PCR product was around 560 bp.

The following capture nucleotide sequences were chosen for the specific capture of the cytochrome P-450 3a sequences:

Capture Nucleotide Sequence
  3a1 5' TGTTTTGATTCGGTACATCTTTG 3' (23 nt) (SEQ ID NO: 187)
  3a3 5' TTGATTTGGTACATCTTTGCT 3' (21 nt) (SEQ ID NO: 188)
  3A9 5' ACTCCTGGGGGTTTTGGGTG 3' 20 nt) (SEQ ID NO: 189)
  3A18 5' ATTACTGAGTATTCAGAAATTCAC 3' (24 nt) (SEQ ID NO: 190)
  3A2 5' GGTTAAAGATTTGGTACATTTATGG 3' (25 nt) (SEQ ID NO: 191)

Each of the sequences above comprised a spacer at its 5' end
Spacer sequence 5' GAATTCAAAGTTGCTGAGAAT-AGTTCAATGGAAGGAAGCG 3' (SEQ ID NO: 36). Capture nucleotide sequences were aminated at their 5' end.

Each of the sequences above comprises a spacer at its 5' end
Spacer sequence 5' GAATTCAAAGTTGCTGAGAAT-AGTTCAATGGAAGGAAGCG (SEQ ID NO: 36).

Example 15

Identification of GMO on Biochips

The following primers were chosen for the amplification step of the GMO.
Consensus primers to detect GMO on biochips:

These primers allowed the amplification of the following genes:
  1) CTP1, CTP2, CP4EPSPS, S CryIAb and hsp 70 Int. in Mon 809 (corn, Monsanto)
  2) hsp 70 Int. and S CryIAb in Mon 810 (corn, Monsanto)
  3) S CryIAb and S Pat in Bt 11 (corn, Novartis)
  4) CTP4 and EPSPS in GTS40-3-2 (soybean, Monsanto)

The capture nucleotide sequences were chosen in these sequences to allow discrimination. Each of the sequences above comprised a spacer at its 5' end
Spacer sequence 5' GAATTCAAAGTTGCTGAGAAT-AGTTCAATGGAAGGAAGCG (SEQ ID NO: 36).

The following sequences were chosen as specific capture probes of the GMO:
  OT1 pat (T25, Bt11) TGGTGGATGGCATGATGTTG-GTTTTTGGCA (SEQ ID NO: 203)
  OT2 CryIAb (Bt11) GCACGAAGCTCTGCAATCGCA-CAAACCCGT (SEQ ID NO: 204)
  OT3 P-PCK (Bt176) TGGGGGTAGCTGTAGTCG-GACTCGGACTGG (SEQ ID NO: 205)
  OT4 CP4EPSPS/Tnos AGCCCCTAGCTAGGGGGTG-GCCAGGAAGTA (SEQ ID NO: 206)

Example 16

Detection of Gyrase (Sub-unit A) Sequences on Array Bearing Genus and Species Specific Capture Nucleotide Sequences Example of Bacterial Detection Amplification of the Sequences The amplified target sequences are fragments of the gyrase gene (sub-unit A) sequences corresponding to the different genus and species (table 1) which were amplified by a PCR using the following consensus primers:

```
Pgyr1: 5' GANGTNATSGGTAAATAYCA 3'   (SEQ ID NO: 207)
Pgyr2: 5' CGNRYYTCVGTRTAACG 3'      (SEQ ID NO: 208)
```

The PCR was performed in a final volume of 100 μl containing: 3 mM MgCl$_2$, 1 mM Tris pH 8, 1 μM of each primer, 200 μM of dATP, dCTP and dGTP, 150 μM of dTTP, 50 μM of biotin-16-dUTP, 2.5 U of Taq DNA polymerase

| Forward | | Reverse | |
|---|---|---|---|
| OPP3551 (P-35S) 5'CGTCTTCAAAGCAAGTGGATTG3' | (SEQ ID NO: 192) | OPT352 (T-35S) 5'GAAACCCTAATTCCCTTATCAGGG3' | (SEQ ID NO: 193) |
| OPTE91 (T-E9) 5'TCATGGATTTGTAGTTGAGTATGAA3' | (SEQ ID NO: 194) | OPTnos2 (T-nos) 5'ATCTTAAGAAACTTTATTGCCAAATGT3' | (SEQ ID NO: 195) |
| OPEPS3 (EPSPS) 5'GCTGTAGTTGTTGGCTGTGGT3' | (SEQ ID NO: 196) | OPTE92 (T-E9) 5'CTGATGCATTGAACTTGACGA3' | (SEQ ID NO: 197) |
| OPLB1 (octopine Left Border) 5'ATCAGCAATGAGTATGATGGTCAAT3' | (SEQ ID NO: 198) | OPEPS4 (EPSPS) 5'GCGACATCAGGCATCTTGTT3' | (SEQ ID NO: 199) |
| OPLB3 (nopaline Left Border) 5'ACAAATTGACGCTTAGACAACT3' | (SEQ ID NO: 200) | OPRB2 (octopine Right Border) 5'TGCCAGTCAGCATCATCACAC3' | (SEQ ID NO: 201) |
| | | OPRB4 (nopaline Right Border) 5'TAAGGGAGTCACGTTATGACC3' | (SEQ ID NO: 202) |

(Boehringer Mannheim, Allemagne), 1 U of Uracil-DNA-glycosylase heat labile (Boehringer Mannheim, Allemagne), 1 ng of plasmid containing gyrase gene. Samples were first denatured at 94° C. for 5 min. Then 40 cycles of amplification were performed consisting of 30 sec at 94° C., 45 sec at 48° C. and 30 sec at 72° C. and a final extension step of 10 min at 72° C. Water controls were used as negative controls of the amplification. The sizes of the amplicons obtained using these primers were 166 bp for all genera Production of the Capture Nucleotide Sequences and of the Targets The capture nucleotide sequences contain a spacer fixed on the support by its 5' end and of the following sequence 5' ATAAAAAAGTGGGTCTTA-GAAATAAATTTCGAAGTGCAATAATTATTATTCAC AACATTTCGATTTTTGCAACTACT-TCAGTTCACTCCA3') (SEQ ID NO: 209), followed by the following specific sequences for the various Gyrase from the different bacteria:

volume dispensed is about 0.5 nl. Slides are dried at room temperature and stored at 4° C. until used.

Hybridization

At 65 µl of hybridization solution (AAT, Namur, Belgium) were added 5 µl of amplicons and the solution was loaded on the array framed by an hybridization chamber. For positive controls 2 nM biotinylated CMV amplicons of 437 bp were added to the solution; their corresponding capture nucleotide sequences were spotted on the array. The chamber was closed with a coverslip and slides were denatured at 95° C. for 5 min. The hybridization was carried out at 65° for 30 min. Samples were then washed 4 times with a washing buffer.

Colorimetric Detection

The glass samples were incubated 45 min at room temperature with 800 µl of streptavidin labelled with colloidal gold 1000× diluted in blocking buffer (Maleic buffer 100 mM pH 7.5, NaCl 150 mM, Gloria milk powder 0.1%).

| Name Capture nucleotide sequence | Sequence (5'->3') | |
|---|---|---|
| A. Genus level | | |
| T Staphy genus | GACTCWTCAATTTATGAWGCHATGGTAHGAAYGG | (SEQ ID NO: 210) |
| T Entero genus | GACAGTGCGATYTAYGARTCAATGGTRCGG | (SEQ ID NO: 211) |
| T Strepto genus | TGGTTCGTATGGCTCAATGGTGGAGYTAY | (SEQ ID NO: 212) |
| B. Species level | | |
| T S. aureus | CTCAAGATTTCAGTTATCGTTATCCGCT | (SEQ ID NO: 213) |
| T S. epidermidis | CCCAAGACTTTAGTTATCGTTATCCACT | (SEQ ID NO: 214) |
| T S. hominis | CACAAACCTTTAGCTATCGTTATCCTC | (SEQ ID NO: 215) |
| T Entero.faecium | ACAGCCATTCAGCTACCGTTATATGCT | (SEQ ID NO: 216) |
| T Entero.faecalis | AACCTTTTAGTTATCGGGCTATGTTAGTT | (SEQ ID NO: 217) |
| T S. pneumoniae | GATGGAGATAGTGCTGCCGCTCAAC | (SEQ ID NO: 218) |
| T S. epyogenes | CTTGTTGATGGGCATGGCAATTTTGG | (SEQ ID NO: 219) |
| T H. influenzae | TTCTCACTTCGCTATATGTTGGTTGATG | (SEQ ID NO: 220) |

The capture nucleotide sequences were first synthesized chemically and later on produced by PCR amplification after cloning of the sequences into the plasmid pGEM-T Easy Vector System(Promega, Madison, USA). The capture nucleotide sequences were then produced by amplification of the plasmids using a common 5' aminated primer 5' GAATTCAAAGTTGCTGAGAATAGTTCA (SEQ ID NO: 221) and a second primer of 27 bases complementary of each capture nucleotide sequence.

The aminated capture polynucleotide sequences (longer than 100 bases) were spotted from solutions at concentrations ranging from 150 to 3000 nM. The capture nucleotide sequences were printed onto the aldehyde microscopic slides with a home made robotic device (250 µm pins from Genetix (UK). The solutions of spotting were from AAT (Namur, Belgium). The spots have 400 µm in diameter and the After 5 washes with washing buffer, the presence of gold served for catalysis of silver reduction using a staining solution (Silver Blue Solution, AAT, Namur, Belgium). The slides were incubated 10 min with 800 µl of revelation mixture, then rinsed with water, dried and analyzed using a microarray reader (Worstation, AAT, Namur, Belgium). The spots of the arrays were then quantified by a specific quantification software.

Example 17

Detection of Virus Species and Subtypes

The virus to be detected were the adenovirus, the herpes virus 1, 5 and 4. The consensus primers for the virus amplification were A(G)C(A,T)G(C,T)GCCGCCGTGT(A)

T(A,C)C(T)G(A,C) (SEQ ID NO: 222) and GT(G,C)G(T,A)GTTGTTTTTG(A)T(C)G(C)G(T) (SEQ ID NO: 223).

The amplicons of the virus are respectively of 315, 331, 779, and 820 bases long for the 4 virus corresponding to the sequences No. 420-734, 7924-8254, 1562-2340, 120761-130580.

The conditions for the PCR amplification were as described in example 1 but with an annealing temperature of 45° C. After amplification, the amplicons were hybridized on an array bearing the capture nucleotide sequences for each virus species and subtypes. The capture nucleotide sequences were composed of a spacer fixed by its 5' end to the slides and have the sequence as in example 16 and a specific part located on the 3' end of the capture nucleotide sequence.

Specific sequences of the capture nucleotide sequences:
Adenovirus: 5'-AACTCTTCTCGCTGGCACTCAA-GAGTG-3' (SEQ ID NO: 224)
Herpes virus 1: 5'-GTGGAAGTCCTGATACCCATC-CTACAC-3' (SEQ ID NO: 225)
Herpes virus 5: 5'-AAAAGCGTGTGATCTGACCGAG-GCGAA-3' (SEQ ID NO: 226)
Herpes virus 4: 5'-AGGTCCTTGAGGAAGAAGTGT-TCCAGG-3' (SEQ ID NO: 227)
Tm=82° C.

The hybridization, the colorimetry labelling and the quantification were performed as in example 1.

Example 18

Detection of Cytochrome b Sequences on Array Bearing Species Specific Capture Nucleotide Sequences Example of Meat Origin The amplified target sequences are fragments of the cytochrome b gene sequences corresponding to the different species were amplified by a PCR using the following consensus primers

```
Meat1 5' TCCTCCCATGAGGAGAAATAT 3' (SEQ ID NO: 228)

Meat2 5' AGCGAAGAATCGGGTAAGGGT 3' (SEQ ID NO: 229)
```

The PCR were performed as in example 1. The sizes of the amplicons obtained using these primers were between 130 and 147 bp for all genus. After amplification, the amplicons were hybridized on an array bearing the capture nucleotide sequences for each species. The capture nucleotide sequences were composed of a spacer fixed by its 5' end to the slides and having the same sequence as in example 1 and a specific part located on the 3' end of the capture nucleotide sequence.
Spacer 5' ATAAAAAAGTGGGTCTTA-GAAATAAATTTCGAAGTGCAATAATTAT-TATTCAC AACATTTCGATTTTTGCAACTACT-TCAGTTCACTCCA3' (SEQ ID NO: 209)
Specific sequences of the capture nucleotide sequences
Chicken CCTTAACGACTCTTATCCAAACACTAT-GCCACCGGGGAG (SEQ ID NO: 230)
Duck CCCTAACGACTCTTATCCAAACACTACT-GCCATCGGGGAG (SEQ ID NO: 231)
Ostrich CCTTAACGAACTCTAAG (SEQ ID NO: 232)
Pig AAAGAGGAGTAGAATCACGATTAAG (SEQ ID NO: 233)
Quail CCATGTCGACTCTTATCCAAACACTACT-GCCATCGTGGAG (SEQ ID NO: 234)
Rabbit CCCTAACGACTATCCTCCAATCACTAAT-GCCAACGAGGGG (SEQ ID NO: 235)
Turkey CCCTAACGACTCTTATCCAAACACTACT-GCCATCGGGAG (SEQ ID NO: 236)
Wildpig CCCTATCGACTATCTTCTAAACAC-TACTGGCATCGAGGAG (SEQ ID NO: 237)
Cow CCTAACGACTATTCTCCAACCACTACT-GACAACGAGGAG (SEQ ID NO: 238)
The consensus capture nucleotide sequence for all these animal detection is
ATTCTGAGGGGCACCGTCATCACAAAC-CTATTTCAGCAATCCCC TACATGGCAAAC-CCTAGTAGAATGAGCCTGAGGGG-GATTTTCAGTGACAACC (SEQ ID NO: 239)
To identify the cow species, another couple of consensus primer was design
Cow1 AAGACATAATATGTATATAGTAC (SEQ ID NO: 240)
Cow2 GAAAAATTTAAATAAGTATCTAG (SEQ ID NO: 241)
Specific capture nucleotide sequences have been designed
BrownSwiss GCGGCATGATAATTA (SEQ ID NO: 242)
Jersey CGCTATTCAATGAAT (SEQ ID NO: 243)
Ayrshire GCTCACCATAACTGT (SEQ ID NO: 244)
Hereford ATCTGATGGTAAGGA (SEQ ID NO: 245)
Simmental ATAAGCCTGGACATT (SEQ ID NO: 246)
Piemontaise ATAAGCATGGACATT (SEQ ID NO: 247)
Canadienne TCACTCGGCATGATA (SEQ ID NO: 248)
RedAngus AATGGTAGGGGATAT (SEQ ID NO: 249)
Limousine ATGGACTCATGGCTA (SEQ ID NO: 250)
AberdeenAngus TATTCAATGAACTTT (SEQ ID NO: 251)
Butana GCATGGGGTATATAA (SEQ ID NO: 252)
Charolais ATAAGCGTGGACATTA (SEQ ID NO: 253)
Fresian CCTTAAATACCTACC (SEQ ID NO: 254)
Kenana TGCTATAGAAGTCAT (SEQ ID NO: 255)
N'Dama TGTTATAGAAGTCAT (SEQ ID NO: 256)
The hybridization, the colorimetry labelling and the quantification were performed as in example 1.

Example 19

Detection of Sucrose Synthase Sequences on Array Bearing Species Specific Capture Nucleotide Sequences Example of Plant Origin The amplified targets are fragments of the sucrose synthase gene sequences corresponding to the different species were amplified by a PCR using the following consensus primers:
PPss3 5' GGTTTGGAGARRGGNTGGGG 3' (SEQ ID NO: 257)
PPss4 5' TCCAADATGTAVACAACCTG 3' (SEQ ID NO: 258)
The PCR were performed as in example 1. The sizes of the amplicons obtained using these primers were 221 bp for all genus. After amplification, the amplicons were hybridized on an array bearing the capture nucleotide sequences for each species. The capture nucleotide sequences were composed of a spacer fixed by its 5' end to the slides and having the following sequence and a specific part located on the 3' end of the capture nucleotide sequence.
Spacer 5' ATAAAAAAGTGGGTCTTA-GAAATAAATTTCGAAGTGCAATAATTAT-TATTCAC AACATTTCGATTTTTGCAACTACT-TCAGTTCACTCCA3' (SEQ ID NO: 209)

Specific sequences of the capture nucleotide sequences:
TPss1 (potato) GAAGCATGCATACCATCTCTAGCA (SEQ ID NO: 259)
TPss3 (tomato) GGAGCATGCAGATCATCTCTAGAA (SEQ ID NO: 260)
TPss7 (oryza) GAAGCAAGTGGATGGTGTCAAGCA (SEQ ID NO: 261)
TPss8 (zea) AGAGGAGGTGGATAGTCTCCTGTG (SEQ ID NO: 262)
TPss9 (soja) AGAGAAGTTGAATTGACTCAAGGA (SEQ ID NO: 263)
TPss11 (wheat) AGAGAAGGTGGATAGTCTCGCTCG (SEQ ID NO: 264)
TPss12 (bareley) AGAGAAGGTGGATAGTCTCGCTCG (SEQ ID NO: 265)
TPss13 (bean) ATAGAAGCTGAATGGACTCGAGCA (SEQ ID NO: 266)
TPss14 (carrot) GAAGCATGTGAAACATCTCAGTAA (SEQ ID NO: 267)

The hybridization, the colorimetry labelling and the quantification were performed as in example 1.

Example 20

Detection of Cytochrome b Sequences on Array Bearing Species Specific Capture Nucleotide Sequences Example of Fishes Species, Genus and Families The amplified target sequences are fragments of the cytochrome b gene sequences corresponding to the different species were amplified by a PCR using the following consensus primers:
Fish1 5' ACTATTHCTAGCCATVCAYTA 3' (SEQ ID NO: 268)
Fish2 5' AGGTAGGAGCCATAAAGACCTCG 3' (SEQ ID NO: 269)

The PCR were performed as in example 1. The sizes of the amplicons obtained using these primers were 170 bp for all genus. After amplification, the amplicons were hybridized on an array bearing the capture nucleotide sequences for each species. The capture nucleotide sequences were composed of a spacer fixed by its 5' end to the slides and having the following sequence and a specific part located on the 3' of the capture nucleotide sequence.

Spacer (SEQ ID NO: 209)
5'ATAAAAAAGTGGGTCTTAGAAATAAATTTCGAAGTGCAATAA
TTATTATTCACAACATTTCGATTTTTGCAACTACTTCAGTTCACTCCA3'

Specific sequences of the capture nucleotide sequences for the species:
G. morhua AAGGCTTAATCAGTCGGCATCAAATGTA (SEQ ID NO: 270)
G. macrocephalus AAGGCTTACTCAGTTGGCATTAAATGTA (SEQ ID NO: 271)
P. flesus GAAGCCTACTCAGTTGGCATCAACTGCA (SEQ ID NO: 272)
M. merluccius AACGCCTAATCAGTAGGCATTAAATGCA (SEQ ID NO: 273)
O. mykiss AAAGCTTACTCAGTCGGCATTGATTGTA (SEQ ID NO: 274)
P. platessa GAAGCCTATTCAGTCGGCATCAACTGCA (SEQ ID NO: 275)
P. virens AAAGCTTAATTAGTCGGCATTAAATGTA (SEQ ID NO: 276)
S. salar CAATGCCTACTCAGTCGGTATCGATTGTA (SEQ ID NO: 277)
S. pilchardus GAAGCTTAGTCAGTAGGCATCAAATGCA (SEQ ID NO: 278)
A. thazard AAAGCCTATTCAGTTGGCTTCAAATGTA (SEQ ID NO: 279)
T. alalunga AAAGCCTACTCAGTAGGCTTCAAATGTA (SEQ ID NO: 280)
T. obesus AAAGCCTACTCAGTTGGCTTTAACTGTTA (SEQ ID NO: 281)
R. hippoglossoides GAAGCCTATTCAGTCGGCATCAACTGCA (SEQ ID NO: 282)
S. trutta AAAGCCTACTCAGTCGGCATCGATTGCA (SEQ ID NO: 283)
S. sarda AAAGCCTAATCAGTCGGCTTTAATTGCA (SEQ ID NO: 284)
T. thynnus AAGGCCTATTCAGTTGGCTTCAACTGTA (SEQ ID NO: 285)
S. scombrus AACGCCTACTCAGTAGGCTTCAAATGCA (SEQ ID NO: 286)

Specific sequences of the capture nucleotide sequences for the families:
Salmonidae
AAACATTCACGCTAACGGAGCATCTTTCTTCTTTATCTGT (SEQ ID NO: 287)
Pleuronectidae
AAGCATTCATGCCAACGGCGCATCATTCTTTTTCATTTGC (SEQ ID NO: 288)
Pleuronectidae
GAATATACATGCTAATGGTGCCTCTTTCTTTTTTATTTGT (SEQ ID NO: 289)
Scombridae
AAACCTCCACGCAAACGGAGCCTCTTTCTTTCTTTATCTGC (SEQ ID NO: 290)
Among this family, a consensus capture nucleotide sequence was designed to detect the *Thunnus* genus
ATTCCACATCGGCCG (SEQ ID NO: 291)
Consensus capture nucleotide sequences for these various fish families:
ATCCGAAACATCCACGCAACGGGCATCTTTCTTCTTTATCTGTATCTACTTACACAT (SEQ ID NO: 292)

The hybridization, the colorimetry labelling and the quantification were performed as in example 1.

Example 21

Detection of Cytochrome P450 Isoforms after Amplification with Consensus Primers and Hybridization of the Amplicons on Arrays The amplified targets are fragments of the cytochrome P450 gene sequences corresponding to the different families which were amplified by a PCR using the following consensus primers:
p450-1 5'TCCGCAACTTGGGCCTGGGCAAGA 3' (SEQ ID NO: 293)
p450-2 5' CCTTCTCCATCTCTGCCAGGAAG 3' (SEQ ID NO: 294)

The conditions for the PCR amplification are the same as in example 1. The sizes of the amplicons obtained using these primers were 970 bp. After amplification, the amplicons were hybridized on an array bearing the capture nucleotide sequences for each single point mutations.

The capture nucleotide sequences were composed of a spacer fixed by its 5' end to the slides and having the following sequence and a specific part located on the 3' end of the capture nucleotide sequence.

Spacer 5' GAATTCAAAGTTGCTGAGAATAGT-TCAATGGAAGGAAGCG 3' (SEQ ID NO: 36)

Specific sequences of the capture nucleotide sequences for the single point mutations from different families of cytochrome p450.

| Target Gene: Human CYP2D6 | | |
|---|---|---|
| Name | Sequence (5'-3') | |
| WT | GAAAGGGGCGTCCTGGG | (SEQ ID NO: 295) |
| *4 substitution T in C at position 13 of WT | GAAAGGGGCGTCtTGGG | (SEQ ID NO: 296) |
| WT | GCTAACTGAGCACAGGA | (SEQ ID NO: 297) |
| *3 Deletion of A at position 14 of WT | GCTAACTGAGCACGGA | (SEQ ID NO: 298) |
| WT | CTCGGTCACCCCCTGC | (SEQ ID NO: 299) |
| *6 Deletion of C at position 12 of WT | CTCGGTCACCCCTGC | (SEQ ID NO: 300) |

| Target Gene: Human CYP2C19 | | |
|---|---|---|
| Name | Sequence (5'-3') | |
| WT | AATTATTTCCCAGGAA | (SEQ ID NO: 301) |
| *2 substitution G in A | AATTATTTCCCaGGAA | (SEQ ID NO: 302) |
| WT | AGCACCCCCTGAATCC | (SEQ ID NO: 303) |
| *3 substitution G in A | AGCACCCCCTGaATCC | (SEQ ID NO: 304) |

The hybridization, the colorimetry labelling and the quantification were performed as in example 1.

Example 22

Evidence for Bacterial Presence During the PCR (Real Time PCR) and Identification on Microarrays Example of detection of the main bacteria responsible for meningitis by real-time PCR on cerebrospinal fluid was combined with genus and species sequence identification on DNA microarray The tuf is phylogenetically well conserved gene amongst bacteria, it encodes an elongation factor (TE). The biological sample for the detection of meningitis was cerebrospinal fluid. Indeed, this medium is normally sterile and if there is an infection, it would be contaminated by only one pathogen. Thus it limits the risk to amplify other genus with consensus primers.

For a real-time PCR consensus primers for the tuf gene, amplify all genus and species of interest and the consensus probe for the tuf gene was labelled with two fluorochromes (quencher and emettor) as internal control of the PCR.

Biochips bearing specific capture probes for bacteria genus and species currently found in meningitis infections were:

*Neisseria menengitidis* serogroupA
*Neisseria menengitidis* serogroupB
*Haemophylus influenzae*
*Escherichia coli*
*Streptococcus pneumoniae*
*Streptococcus agalactiae*
*Staphylococcus aureus*
*Staphylococcus epidermidis*
*Staphylococcus haemolyticus*
*Staphylococcus hominis*
*Staphylococcus saprophyticus*

For the Primers Consensus Sense were:
5' GAATTRGTTGAAATGGAA 3' 18 nt (SEQ ID NO: 305) (R=A or G)
position 443–460 Tm=46–48° C.
1 mismatch maximum For the Consensus Antisense were:
5' GTAGTACGGAARTAGAA 3' 17 nt (SEQ ID NO: 306) (R=A or G)
position 995–1011 Tm=46–48° C.
1 mismatch maximum For the Double labelled Probe (sense) were:
5' GGTGTTGAAATGTTCC 3' 16 nt (SEQ ID NO: 307)
position 776–792 Tm=46° C.
1 mismatch maximum
Size of the amplified product: 569 bp Genus Specific Capture Probes
1) *Meningococcus* 5' CGACCTGCTGTCCAGCT 3'(17 nt) (SEQ ID NO: 308)
Identical for serogroup A and B and a minimum of 5 mismatches against the other genus.
2) *Streptococcus* 5' CTTCAGGACGTATCGACC 3'(18 nt) (SEQ ID NO: 309)

Identical for *Streptococcus pneumoniae* and *Streptococcus agalactiae* and a minimum of 5 mismatches against the other genus.

3) *Staphylococcus* 5' TTATTAGACTACGCTGAAG 3'(19 nt) (SEQ ID NO: 310)

Identical for *Staphylococcus aureus, Staphylococcus epidermidis, Staphylococcus haemolyticus, Staphylococcus hominis, Staphylococcus saprophyticus* and a minimum of 6 mismatches against the other genus.

Species Specific Capture Probes

1) *Neisseria menengitidis* serogroup A
 5' TCTATTTCCGGTCGTGGT 3'(18 nt) (SEQ ID NO: 311)
2) *Neisseria menengitidis* serogroup B
 5' CCATTTCCGGCCGCGG 3'(16 nt) (SEQ ID NO: 312)
3) *Haemophylus influenzae*
 5' GAGTTAGCAAACCACTTAG 3'(19 nt) (SEQ ID NO: 313)
4) *Escherichia coli*
 5' AACTGGCTGGCTTCCTG 3'(17 nt) (SEQ ID NO: 314)
5) *Streptococcus pneumoniae*
 5' GTATCAAAGAAGAAACTCAAA 3'(21 nt) (SEQ ID NO: 315)
6) *Streptococcus agalactiae*
 5' GTATTAAAGAAGATATCCAAA 3'(21 nt) (SEQ ID NO: 316)
7) *Staphylococcus aureus*
 5' GGTTTACATGACACATCTAA 3'(20 nt) (SEQ ID NO: 317)
8) *Staphylococcus epidermidis*
 5' GTATGCACGAAACTTCTAAA 3'(20 nt) (SEQ ID NO: 318)
9) *Staphylococcus haemolyticus*
 5' GTATCCATGACACTTCTAAA 3'(20 nt) (SEQ ID NO: 319)
10) *Staphylococcus hominis*
 5' GGTATCAAAGAAACTTCTAAA 3'(21 nt) (SEQ ID NO: 320)
11) *Staphylococcus saprophyticus*
 5' ATGCAAGAAGAATCAAGCAA 3'(20 nt) (SEQ ID NO: 321)

Each of the sequences above comprised a spacer at its 5' end Spacer sequence 5' GAATTCAAAGTTGCTGAGAATAGTTCAATGGAAGGAAGCG 3' (SEQ ID NO: 36). Capture probes were aminated at their 5' end.

Example 23

HLA Identification

Glass surface was activated in order to bear aldehydes groups as proposed by EP-00870184.9. The slides were then incubated with a Protein A at 5 µg/ml in PBS solution for 60 min. The slides were washed in PBS and then incubated for 5 min. in NaBH$_4$ solution at 2.5 mg/ml. After washing they were incubated for 2 h with 10% milk powder and then washed again. Antibodies at concentration of 0.1 mg/ml were spotted on the glass slides with solid pins of 0.250 mm diameter and the spots were around 0.35 mm diameter final. The spotting solution contained buffer borate 0.05 M pH 8, glycerol 40% and NP40 0.02%. After 3 washes with 0.01 M phosphate pH 7.4, non-specific binding sites were blocked with PBS containing milk powder at 0.1% for 1 h at 20° C.

For the reaction of the targets, the slides were incubated for 1 h at 20° C. with the samples in the presence of PBS containing milk powder at 0.1%. After 4 washes of one minute with a 10 mM maleate buffer containing 15 mM NaCl (washing buffer) the slides were incubated for 45 min. at 20° C. with an antibody common for the various targets potentially present in the samples, then with a conjugate of anti-IgG/gold particles of 10 nm diameter (diluted 100 times) in 100 mM maleate buffer containing 150 mM NaCl.

The slides were washed 5 times in the same washing buffer as before and then incubated for 10 min. in the Silver Blue detection solution (AAT Namur) for obtaining the silver crystal precipitation. The slides were finally washed in water before being read in the Silver Blue Reader (AAT).

The HLA-A typing was obtained using antibodies specific of the types or subtypes. The antibodies against HLA-ABC common, HLA-B7, HLA-B27, were obtained from Cymbus Biotechnology, Ltd., Hampshire, UK. Other antibodies were from Pel-Freez especially the antibodies directed against the HLA-A2, A203 and A210 or HLA-B39, B3901, B3902, which allow typing and subtyping of the HLA. Lymphocytes were isolated from the blood according to the classical microlypophocytotoxicity assay (Pel-Freez, Brown Deer, Wis., U.S.A.). Lymphocytes at 10×106 cells/ml were incubated for 30 min. at 37° C. with the antibody array in RPMI 1640 media with Hepes buffer. The arrays are then washed 4 times in the same medium. The second antibodies for cells were directed against CD-2 and CD-19. Then the anti-IgG/nano-gold complexes were incubated followed by the Silver Blue (AAT, Namur, Belgium) for the detection.

TABLE 1

Horizontal identification of the genus

| | Staphylococcus | Enterococcus | Haemophylus |
|---|---|---|---|
| *) | aureus | faecalis | influenzae |
| | epidermidis | faecium | |
| | hominis | | |

*) Identification of the species

TABLE 2

| | Meat | | |
|---|---|---|---|
| Galinacea | Leporidae | Suidae | Bovidae |
| Chicken | Rabbit | Pig | Cow |
| Duck | | Wild pig | Brownswiss, Jersey, Hereford, Simmental, Piemontaise, Canadienne, RedAngus, Limousine, AberdeenAngus, Butana, Charolais, Fresian, Kenana, N'Dama |
| Ostrich | | | |
| Turkey | | | |
| Quail | | | |

TABLE 3

Fish families

| Classification Family | Scombridae | Salmonidae | Merlucciidae | Pleuronectidae | Gadidae | Clupeidae |
|---|---|---|---|---|---|---|
| Genera Species | Auxis A. thazard | Oncorhynchus O. mykiss | Merluccius M. merluccius | Pleuronectes P. platessus | Pollachius P. virens | Sardina S. pilchardus |
| Genera Species | Sarda S. sarda | Salmo S. salar S. trutta | | Platichthys P. flesus | Gadus G. morhua G. macrocephalus | |
| Genera Species | Scomber S. scombrus | | | Reinhardtius R. hippoglossoides | | |
| Genera Species | Thunnus T. albacares T. obesus T. alalunga T. thynnus | | | | | |

Animal Meat

| Classification Family | Galinacea | Leporidae | Suidae | Bovidae |
|---|---|---|---|---|
| Genera | Chicken | Rabbit | Pig | |
| Genera | Duck | | Wild pig | |
| Genera | Ostrich | | | |
| Genera | Turkey | | | |
| Genera | Quail | | | |
| Species | | | | Cow Brownswiss, Jersey, Hereford, Simmental, Piemontaise, Canadienne, RedAngus, Limousine, AberdeenAngus, Butana, Charolais, Fresian, Kenana, N'Dama |

What is claimed is:

1. A method for identifying and/or quantifying a biological organism in a sample by detecting a nucleotide sequence of said biological organism, wherein said nucleotide sequence presents a homology higher than 30% with at least 4 other homologous nucleotide sequences from other biological organisms, comprising:

amplifying or copying at least one of said homologous nucleotide sequences into full-length double-stranded target homologous nucleotide sequences having between 100 and 800 bases using primer pairs which are capable of amplifying or copying at least four of said target homologous nucleotide sequences from other organisms;

contacting said full-length double-stranded target homologous nucleotide sequences resulting from the amplifying step with single-stranded different capture nucleotide sequences, at least two of said single-stranded capture nucleotide sequences being specific for at least two of said target homologous nucleotide sequences, said single-stranded capture nucleotide sequences being covalently bound in an array to an insoluble solid support via a spacer comprising a nucleotide sequence greater than 40 bases, said array comprising at least four different bound single-stranded capture nucleotide sequences/cm² of solid support surface, and wherein each of said single-stranded capture nucleotide sequences comprises a nucleotide sequence of about 5 to about 60 bases wherein said nucleotide sequence of about 5 to about 60 bases is able to specifically bind to one of the full-length target homologous nucleotide sequences without binding to said at least four other homologous nucleotide sequences, wherein said array also contains consensus capture nucleotide sequences for a common detection of said full-length target homologous nucleotide sequences, said consensus capture nucleotide sequences having a length specific of the target comprising between about 10 and about 1000 bases, and detecting specific hybridization of the full-length target homologous nucleotide sequence to said single-stranded capture nucleotide sequences, wherein said single-stranded capture nucleotide sequence is bound to the insoluble solid support at a specific location upon the array, and wherein the binding between said full-length target homologous nucleotide sequence and its corresponding single-stranded capture nucleotide sequence forms a signal at the expected location, the detection of said signal allowing a discrimination of the target homologous nucleotide sequence being specific of said organism from other organisms from the same or other groups, sub-groups or sub-sub-groups of said organisms.

2. The method of claim 1, wherein said biological organism is present in the sample among at least 2 other organisms.

3. The method of claim 1, wherein said biological organism is present in the sample among at least 4 other organisms.

4. The method of claim 1, further comprising extracting the nucleotide sequence from said organism.

5. The method of claim 1, further comprising labeling said organism or its nucleotide sequence as targets.

6. The method of claim 1, wherein said organism is a microorganism.

7. The method of claim 1, further comprising identifying and/or quantifying the presence of several groups, sub-groups or sub-sub-groups of said organisms being related to each other, wherein the binding between full-length target homologous nucleotide sequences and corresponding consensus capture nucleotide sequences forms a signal at an expected location allowing the identification of a target nucleotide sequence specific of a group, sub-group or sub-sub-group of organisms.

8. The method of claim 7, wherein the array contains two categories of capture nucleotide sequences, a first category of capture nucleotide sequences being specific for individual full-length target nucleotide sequences or their sub-groups and a second category of capture nucleotide sequences being specific for all the nucleotide sequences of the group.

9. The method of claim 1, wherein said consensus capture nucleotide sequences has a sequence specific for the full-length target nucleotide sequences, said consensus capture nucleotide sequences comprising a sequence which is between about 100 and 600 bases in length.

10. The method of claim 1, wherein the amplified full-length target nucleotide sequence is a DNA nucleotide sequence amplified by PCR.

11. The method of claim 1, wherein all or most of the full-length target amplified sequences are obtained by PCR with the same primer pair.

12. The method of claim 1, wherein the presence of any full-length target amplified nucleotide sequence is firstly detected during the genetic amplification cycles and thereafter identified on the array.

13. The method of claim 1, wherein the step of detecting the presence of any amplified full-length target nucleotide sequences and the genetic amplification step are performed in a same chamber.

14. The method of claim 1, wherein the amplified full-length target nucleotide sequence is mRNA first reverse transcribed into cDNA and then amplified with the same primer pair which is capable of amplifying at least two of said homologous mRNA in said sample.

15. The method of claim 1, wherein the homologous nucleotide sequences are copied by using the same primer pair.

16. The method of claim 1, wherein said spacer greater than 40 and less than about 1000 bases.

17. The method of claim 1, wherein spacer greater than 40 and less than about 120 bases.

18. The method of claim 1, wherein the length of the specific sequence of the capture nucleotide sequence able to hybridize with the corresponding full-length target nucleotide sequences is comprised between about 20 and about 30 bases.

19. The method of claim 1, wherein the density of the capture nucleotide sequences bound to the solid support surface at a specific location is greater than 10 fmoles per $cm^2$ of solid support surface.

20. The method of claim 1, wherein the density of the capture nucleotide sequences bound to the solid support surface at a specific location is greater than 100 fmoles per $cm^2$ of solid support surface.

21. The method of claim 1, wherein the nucleotide sequence(s) to be detected present(s) a homology of greater than about 40% with other homologous nucleotide sequences.

22. The method of claim 1, wherein the nucleotide sequence(s) to be detected present(s) a homology of greater than about 60% with other homologous nucleotide sequences.

23. The method of claim 1, wherein the nucleotide sequence(s) to be detected present(s) a homology of greater than about 80% with other homologous nucleotide sequences.

24. The method of claim 1, wherein the full-length target nucleotide sequences are labelled by a marker and wherein the signal resulting from hybridization by complementary bases pairing between the full-length target nucleotide sequence and its corresponding capture nucleotide sequence is obtained from the detection of said marker.

25. The method of claim 1, wherein other primers are present in the amplification step for the amplification of an antibiotic resistance determining nucleotide sequence.

26. The method of claim 1, wherein the solid support comprises single-stranded capture nucleotide sequences specific for the identification of two or more *Staphylococcus* species, said solid support further comprises a consensus capture nucleotide sequence for a *Staphylococcus* genus identification.

27. The method of claim 1, wherein the nucleotide sequence to be identified and/or quantified in the sample differs from at least one of its homologous nucleotide sequences present in the sample by one or more base(s).

28. The method of claim 1, wherein the arrays contain two to four single-stranded capture nucleotide sequences differing from each other by one or more base(s).

29. The method of claim 1, wherein the quantification of the organism present in the biological sample is obtained by the quantification of the signal.

30. The method of claim 1, wherein the insoluble solid support is selected from the group consisting of glass, an electronic device, a silicon support, a plastic support, silica, metal and a mixture thereof, wherein said support is prepared in a format selected from the group consisting of slides, discs, gel layers and microbeads.

31. The method of claim 6, wherein the microorganism to be identified and/or quantified in the sample belongs to the *Staphylococci* species selected from the group consisting of *S. aureus, S. epidermidis, S. saprophyticus, S. hominis* and *S. haemolyticus*.

32. The method of claim 6, wherein the microorganism to be identified and/or quantified in the sample belong to the *Mycobacteria* genus.

33. The method of claim 1, wherein the nucleotide sequence to be identified and/or quantified in the sample is a sequence which belongs to the MAGE family.

34. The method of claim 1, wherein the nucleotide sequence to be identified and/or quantified in the sample is a sequence which belongs to the HLA-A family.

35. The method of claim 1, wherein the nucleotide sequence to be identified and/or quantified in the sample is a G protein-coupled receptor.

36. The method of claim 1, wherein the nucleotide sequence to be identified and/or quantified in the sample is a dopamine receptor.

37. The method of claim 1, wherein the nucleotide sequence to be identified and/or quantified in the sample is a choline receptor.

38. The method of claim 1, wherein the nucleotide sequence to be identified and/or quantified in the sample is a histamine receptor.

39. The method of claim 1, wherein the nucleotide sequence to be identified and/or quantified in the sample is a sequence which belongs the Cytochrome P450 isoforms family.

40. The method of claim 6, wherein the microorganism to be identified and/or quantified in the sample belongs to a Gram-positive or Gram-negative family bacteria.

41. The method of claim 7, wherein the group, sub-group or individual targets correspond to families, genus, species, subtypes or individual organisms.

42. The method of claim 7, wherein the families, genus, species, subtypes or individuals are bacteria.

43. The method of claim 42, wherein bacteria belongs to at least two of the genus families selected from the group consisting of *Staphylococcus, Enterococcus, Streptococcus, Haemolyticus, Pseudomonas, Campylobacter, Enterobacter, Neisseria, Proteus, Salmonella, Simonsiella, Riemerella, Escherichia, Neisseria, Meningococcus, Moraxella, Kingella, Chromobacterium* and *Branhamella*.

44. The method of claim 1, wherein the identification of the nucleotide sequences allows an identification of the polymorphism of an organism.

45. The method of claim 1, wherein the identification of the nucleotide sequences allows the genotyping of an organism.

46. The method of claim 1, wherein the identification of the nucleotide sequences allows the identification of a single nucleotide polymorphism.

47. The method of claim 1, wherein said single-stranded capture nucleotide sequences comprise a nucleotide sequence of between about 15 and about 40 bases, which is able to specifically bind to said target nucleotide sequence without binding to said at least four homologous nucleotide sequences from other organisms.

48. The method of claim 1, wherein other primers are present in the amplification step for the amplification of another nucleotide sequence.

49. The method of claim 1, wherein the nucleotide sequence to be identified and/or quantified is an RNA sequence submitted to a reverse transcription of its 3' or 5' end by using a consensus primer.

50. The method of claim 1, wherein the nucleotide sequences to be identified and/or quantified are from the FemA gene of *Staphylococci* species selected from the group consisting of *S. aureus, S. epidermidis, S. saprophyticus, S. hominis* and *S. haemolyticus*.

51. The method of claim 1, wherein the solid support also bears another capture consensus nucleotide sequence able to bind to said full-length target nucleotide sequence and to said at least four homologous nucleotide sequences.

52. The method of claim 1, wherein the nucleotide sequences to be identified and/or quantified are from the gene encoding sub-unit A of gyrase.

53. The method of claim 39, wherein the Cytochrome P450 isoforms family comprises a Cytochrome P450 2D6 and a 2C19 isoforms.

54. The method of claim 1, wherein the nucleotide sequences to be identified and/or quantified in the samples come from different animal species and genus belonging to families selected from the group consisting of: Galinaceae, Leporidae, Suidae and Bovidae.

55. The method of claim 1, wherein the nucleotide sequences to be detected and/or quantified in the samples belong to specific fishes species selected from the group consisting of *G. morhua, G. macrocephalus, P. flesus, M merluccius, O. mykiss, P. platessa, P. virens, S. salar, S. pilchardus, A. thazard, T. alalunga, T. obesus, R. hippoglossoides, S. trutta, S. sarda, T. thynnus, S. scombrus* belonging to genera selected from the group consisting of: *Auxis, Sarda, Scomber, Thunnus, Oncorhynch, Salmo, Merluccius, Pleuronectes, Platichtlys, Reinhardtius, Pollachius, Gadus, Sardina*, from several families selected from the group consisting of: Scombridae, Salmonidae, Merluccidae, Pleuronectidae, Gadidae and Clupeidae.

56. The method of claim 1, wherein the nucleotide sequences to be detected and/or quantified in the samples belong to different plant species and genus selected from the group consisting of Potato, tomato, oryza, zea, soja, wheat, barley, bean and carrot.

57. The method of claim 1, wherein the nucleotide sequences to be detected and/or quantified in the samples are genetically modified organisms.

* * * * *

```
                        SEQUENCE LISTING

<160> NUMBER OF SEQ ID NOS: 321

<210> SEQ ID NO 1
<211> LENGTH: 23
<212> TYPE: DNA
<213> ORGANISM: Artificial Sequence
<220> FEATURE:
<223> OTHER INFORMATION: primer for amplification of S. aureus

<400> SEQUENCE: 1
cttttgctga tcgtgatgac aaa                                              23

<210> SEQ ID NO 2
<211> LENGTH: 25
<212> TYPE: DNA
<213> ORGANISM: Artificial Sequence
<220> FEATURE:
<223> OTHER INFORMATION: primer for amplification of S. aureus

<400> SEQUENCE: 2
```
tttatttaaa atatcacgct cttcg        25

<210> SEQ ID NO 3
<211> LENGTH: 23
<212> TYPE: DNA
<213> ORGANISM: Artificial Sequence
<220> FEATURE:
<223> OTHER INFORMATION: primer for amplification of S. epidermidis

<400> SEQUENCE: 3
tcgcggtcca gtaatagatt ata        23

<210> SEQ ID NO 4
<211> LENGTH: 22
<212> TYPE: DNA
<213> ORGANISM: Artificial Sequence
<220> FEATURE:
<223> OTHER INFORMATION: primer for amplification of S. epidermidis

<400> SEQUENCE: 4
tgcatttcca gttatttctc cc        22

<210> SEQ ID NO 5
<211> LENGTH: 24
<212> TYPE: DNA
<213> ORGANISM: Artificial Sequence
<220> FEATURE:
<223> OTHER INFORMATION: primer for amplification of S. haemolyticus

<400> SEQUENCE: 5
attgatcatg gtattgatag atac        24

<210> SEQ ID NO 6
<211> LENGTH: 25
<212> TYPE: DNA
<213> ORGANISM: Artificial Sequence
<220> FEATURE:
<223> OTHER INFORMATION: primer for amplification of S. haemolyticus

<400> SEQUENCE: 6
tttaatcttt ttgagtgtct tatac        25

<210> SEQ ID NO 7
<211> LENGTH: 25
<212> TYPE: DNA
<213> ORGANISM: Artificial Sequence
<220> FEATURE:
<223> OTHER INFORMATION: primer for amplification of S. saprophyticus

<400> SEQUENCE: 7
taaaatgaaa caactcggtt ataag        25

<210> SEQ ID NO 8
<211> LENGTH: 24
<212> TYPE: DNA
<213> ORGANISM: Artificial Sequence
<220> FEATURE:
<223> OTHER INFORMATION: primer for amplification of S. saprophyticus

<400> SEQUENCE: 8
aaactatcca taccattaag tacg        24

<210> SEQ ID NO 9
<211> LENGTH: 24
<212> TYPE: DNA

```
<213> ORGANISM: Artificial Sequence
<220> FEATURE:
<223> OTHER INFORMATION: primer for amplification of S. hominis

<400> SEQUENCE: 9
cgaccagata acaaaaaagc acaa                                          24

<210> SEQ ID NO 10
<211> LENGTH: 22
<212> TYPE: DNA
<213> ORGANISM: Artificial Sequence
<220> FEATURE:
<223> OTHER INFORMATION: primer for amplification of S. hominis

<400> SEQUENCE: 10
gtaattcgtt accatgttct aa                                            22

<210> SEQ ID NO 11
<211> LENGTH: 27
<212> TYPE: DNA
<213> ORGANISM: Artificial Sequence
<220> FEATURE:
<223> OTHER INFORMATION: capture nucleotide ATaur02

<400> SEQUENCE: 11
atttaaaata tcacgctctt cgtttag                                       27

<210> SEQ ID NO 12
<211> LENGTH: 27
<212> TYPE: DNA
<213> ORGANISM: Artificial Sequence
<220> FEATURE:
<223> OTHER INFORMATION: capture nucleotide ATepi02

<400> SEQUENCE: 12
attaagcaca tttctttcat tatttag                                       27

<210> SEQ ID NO 13
<211> LENGTH: 27
<212> TYPE: DNA
<213> ORGANISM: Artificial Sequence
<220> FEATURE:
<223> OTHER INFORMATION: capture nucleotide AThae02

<400> SEQUENCE: 13
atttaaagtt tcacgttcat tttgtaa                                       27

<210> SEQ ID NO 14
<211> LENGTH: 27
<212> TYPE: DNA
<213> ORGANISM: Artificial Sequence
<220> FEATURE:
<223> OTHER INFORMATION: capture nucleotide AThom02

<400> SEQUENCE: 14
atttaatgtc tgacgttctg catgaag                                       27

<210> SEQ ID NO 15
<211> LENGTH: 27
<212> TYPE: DNA
<213> ORGANISM: Artificial Sequence
<220> FEATURE:
<223> OTHER INFORMATION: capture nucleotide ATsap02

<400> SEQUENCE: 15
acttaatact tcgcgttcag cctttaa                                       27
```

-continued

```
<210> SEQ ID NO 16
<211> LENGTH: 24
<212> TYPE: DNA
<213> ORGANISM: Artificial Sequence
<220> FEATURE:
<223> OTHER INFORMATION: consensus primer APstap03

<400> SEQUENCE: 16
cccactcgct tatatagaat ttga                                           24

<210> SEQ ID NO 17
<211> LENGTH: 23
<212> TYPE: DNA
<213> ORGANISM: Artificial Sequence
<220> FEATURE:
<223> OTHER INFORMATION: consensus primer APstap04

<400> SEQUENCE: 17
ccactagcgt acatcaattt tga                                            23

<210> SEQ ID NO 18
<211> LENGTH: 25
<212> TYPE: DNA
<213> ORGANISM: Artificial Sequence
<220> FEATURE:
<223> OTHER INFORMATION: consensus primer APstap05

<400> SEQUENCE: 18
ggtttaataa agtcaccaac atatt                                          25

<210> SEQ ID NO 19
<211> LENGTH: 47
<212> TYPE: DNA
<213> ORGANISM: Artificial Sequence
<220> FEATURE:
<223> OTHER INFORMATION: capture nucleotide (with spacer sequence)
     ATepi03
<221> NAME/KEY: misc_feature
<222> LOCATION: (1)...(20)
<223> OTHER INFORMATION: spacer sequence

<400> SEQUENCE: 19
gaattcaaag ttgctgagaa attaagcaca tttctttcat tatttag                  47

<210> SEQ ID NO 20
<211> LENGTH: 67
<212> TYPE: DNA
<213> ORGANISM: Artificial Sequence
<220> FEATURE:
<223> OTHER INFORMATION: capture nucleotide (with spacer sequence)
     ATepi04
<221> NAME/KEY: misc_feature
<222> LOCATION: (1)...(40)
<223> OTHER INFORMATION: spacer sequence

<400> SEQUENCE: 20
gaattcaaag ttgctgagaa tagttcaatg gaaggaagcg attaagcaca tttctttcat    60
tatttag                                                              67

<210> SEQ ID NO 21
<211> LENGTH: 87
<212> TYPE: DNA
<213> ORGANISM: Artificial Sequence
<220> FEATURE:
<223> OTHER INFORMATION: capture nucleotide (with spacer sequence)
     ATepi05
```

```
<221> NAME/KEY: misc_feature
<222> LOCATION: (1)...(60)
<223> OTHER INFORMATION: spacer sequence

<400> SEQUENCE: 21
gaattcaaag ttgctgagaa tagttcaatg gaaggaagcg tcttcttaaa atctaaagaa      60
attaagcaca tttctttcat tatttag                                          87

<210> SEQ ID NO 22
<211> LENGTH: 67
<212> TYPE: DNA
<213> ORGANISM: Artificial Sequence
<220> FEATURE:
<223> OTHER INFORMATION: capture nucleotide (with spacer sequence)
      Ataur27
<221> NAME/KEY: misc_feature
<222> LOCATION: (1)...(40)
<223> OTHER INFORMATION: spacer sequence

<400> SEQUENCE: 22
gaattcaaag ttgctgagaa tagttcaatg gaaggaagcg atttaaaata tcacgctctt      60
cgtttag                                                                67

<210> SEQ ID NO 23
<211> LENGTH: 67
<212> TYPE: DNA
<213> ORGANISM: Artificial Sequence
<220> FEATURE:
<223> OTHER INFORMATION: capture nucleotide (with spacer sequence)
      Atepi27
<221> NAME/KEY: misc_feature
<222> LOCATION: (1)...(40)
<223> OTHER INFORMATION: spacer sequence

<400> SEQUENCE: 23
gaattcaaag ttgctgagaa tagttcaatg gaaggaagcg attaagcaca tttctttcat      60
tatttag                                                                67

<210> SEQ ID NO 24
<211> LENGTH: 67
<212> TYPE: DNA
<213> ORGANISM: Artificial Sequence
<220> FEATURE:
<223> OTHER INFORMATION: capture nucleotide (with spacer sequence)
      Athae27
<221> NAME/KEY: misc_feature
<222> LOCATION: (1)...(40)
<223> OTHER INFORMATION: spacer sequence

<400> SEQUENCE: 24
gaattcaaag ttgctgagaa tagttcaatg gaaggaagcg atttaaagtt tcacgttcat      60
tttgtaa                                                                67

<210> SEQ ID NO 25
<211> LENGTH: 67
<212> TYPE: DNA
<213> ORGANISM: Artificial Sequence
<220> FEATURE:
<223> OTHER INFORMATION: capture nucleotide (with spacer sequence)
      Athom27
<221> NAME/KEY: misc_feature
<222> LOCATION: (1)...(40)
<223> OTHER INFORMATION: spacer sequence

<400> SEQUENCE: 25
gaattcaaag ttgctgagaa tagttcaatg gaaggaagcg atttaatgtc tgacgttctg      60
```

```
catgaag                                                              67

<210> SEQ ID NO 26
<211> LENGTH: 67
<212> TYPE: DNA
<213> ORGANISM: Artificial Sequence
<220> FEATURE:
<223> OTHER INFORMATION: capture nucleotide (with spacer sequence)
      Atsap27
<221> NAME/KEY: misc_feature
<222> LOCATION: (1)...(40)
<223> OTHER INFORMATION: spacer sequence

<400> SEQUENCE: 26
gaattcaaag ttgctgagaa tagttcaatg gaaggaagcg acttaatact tcgcgttcag   60
cctttaa                                                              67

<210> SEQ ID NO 27
<211> LENGTH: 22
<212> TYPE: DNA
<213> ORGANISM: Artificial Sequence
<220> FEATURE:
<223> OTHER INFORMATION: consensus primer APcons3-1

<400> SEQUENCE: 27
taayaaartc accaacatay tc                                             22

<210> SEQ ID NO 28
<211> LENGTH: 22
<212> TYPE: DNA
<213> ORGANISM: Artificial Sequence
<220> FEATURE:
<223> OTHER INFORMATION: consensus primer APcons3-2
<221> NAME/KEY: misc_feature
<222> LOCATION: (1)...(22)
<223> OTHER INFORMATION: n = A,T,C or G

<400> SEQUENCE: 28
tymgntcatt tatggaagat ac                                             22

<210> SEQ ID NO 29
<211> LENGTH: 67
<212> TYPE: DNA
<213> ORGANISM: Artificial Sequence
<220> FEATURE:
<223> OTHER INFORMATION: capture nucleotide (with spacer sequence )
      Ataur15
<221> NAME/KEY: misc_feature
<222> LOCATION: (1)...(52)
<223> OTHER INFORMATION: spacer sequence

<400> SEQUENCE: 29
gaattcaaag ttgctgagaa tagttcaatg gaaggaagcg tcttcttaaa atgctcttcg   60
tttagtt                                                              67

<210> SEQ ID NO 30
<211> LENGTH: 67
<212> TYPE: DNA
<213> ORGANISM: Artificial Sequence
<220> FEATURE:
<223> OTHER INFORMATION: capture nucleotide (with spacer sequence )
      Ataur40
<221> NAME/KEY: misc_feature
<222> LOCATION: (1)...(27)
<223> OTHER INFORMATION: spacer sequence

<400> SEQUENCE: 30
```

```
gaattcaaag ttgctgagaa tagttcaaat ctttatttaa aatatcacgc tcttcgttta    60
gttcttt                                                              67

<210> SEQ ID NO 31
<211> LENGTH: 67
<212> TYPE: DNA
<213> ORGANISM: Artificial Sequence
<220> FEATURE:
<223> OTHER INFORMATION: capture nucleotide (with spacer sequence )
      Atana15
<221> NAME/KEY: misc_feature
<222> LOCATION: (1)...(52)
<223> OTHER INFORMATION: spacer sequence

<400> SEQUENCE: 31
gaattcaaag ttgctgagaa tagttcaatg gaaggaagcg tcttcttaaa atgctcttca    60
tttagtt                                                              67

<210> SEQ ID NO 32
<211> LENGTH: 67
<212> TYPE: DNA
<213> ORGANISM: Artificial Sequence
<220> FEATURE:
<223> OTHER INFORMATION: capture nucleotide (with spacer sequence )
      Atana27
<221> NAME/KEY: misc_feature
<222> LOCATION: (1)...(40)
<223> OTHER INFORMATION: spacer sequence

<400> SEQUENCE: 32
gaattcaaag ttgctgagaa tagttcaatg gaaggaagcg gtttaaaata tcacgctctt    60
catttag                                                              67

<210> SEQ ID NO 33
<211> LENGTH: 67
<212> TYPE: DNA
<213> ORGANISM: Artificial Sequence
<220> FEATURE:
<223> OTHER INFORMATION: capture nucleotide (with spacer sequence )
      Atana40
<221> NAME/KEY: misc_feature
<222> LOCATION: (1)...(27)
<223> OTHER INFORMATION: spacer sequence

<400> SEQUENCE: 33
gaattcaaag ttgctgagaa tagttcaaat ctttgtttaa aatatcacgc tcttcattta    60
gttcttt                                                              67

<210> SEQ ID NO 34
<211> LENGTH: 67
<212> TYPE: DNA
<213> ORGANISM: Artificial Sequence
<220> FEATURE:
<223> OTHER INFORMATION: capture nucleotide (with spacer sequence )
      Atepi15
<221> NAME/KEY: misc_feature
<222> LOCATION: (1)...(52)
<223> OTHER INFORMATION: spacer sequence

<400> SEQUENCE: 34
gaattcaaag ttgctgagaa tagttcaatg gaaggaagcg tcttcttaaa attttcatta    60
tttagtt                                                              67

<210> SEQ ID NO 35
```

```
<211> LENGTH: 67
<212> TYPE: DNA
<213> ORGANISM: Artificial Sequence
<220> FEATURE:
<223> OTHER INFORMATION: capture nucleotide (with spacer sequence )
      Atepi40
<221> NAME/KEY: misc_feature
<222> LOCATION: (1)...(27)
<223> OTHER INFORMATION: spacer sequence

<400> SEQUENCE: 35
gaattcaaag ttgctgagaa tagttcaaat ctttattaag cacatttctt tcattattta        60
gttcctc                                                                  67

<210> SEQ ID NO 36
<211> LENGTH: 40
<212> TYPE: DNA
<213> ORGANISM: Artificial Sequence
<220> FEATURE:
<223> OTHER INFORMATION: spacer sequence

<400> SEQUENCE: 36
gaattcaaag ttgctgagaa tagttcaatg gaaggaagcg                              40

<210> SEQ ID NO 37
<211> LENGTH: 27
<212> TYPE: DNA
<213> ORGANISM: Artificial Sequence
<220> FEATURE:
<223> OTHER INFORMATION: S. aureus femA capture sequence

<400> SEQUENCE: 37
atttaaaata tcacgctctt cgtttag                                            27

<210> SEQ ID NO 38
<211> LENGTH: 27
<212> TYPE: DNA
<213> ORGANISM: Artificial Sequence
<220> FEATURE:
<223> OTHER INFORMATION: S. epidermidis femA capture sequence

<400> SEQUENCE: 38
attaagcaca tttctttcat tatttag                                            27

<210> SEQ ID NO 39
<211> LENGTH: 27
<212> TYPE: DNA
<213> ORGANISM: Artificial Sequence
<220> FEATURE:
<223> OTHER INFORMATION: S. haemolyticus femA capture sequence

<400> SEQUENCE: 39
atttaaagtt tcacgttcat tttgtaa                                            27

<210> SEQ ID NO 40
<211> LENGTH: 27
<212> TYPE: DNA
<213> ORGANISM: Artificial Sequence
<220> FEATURE:
<223> OTHER INFORMATION: S. hominis femA capture sequence

<400> SEQUENCE: 40
atttaatgtc tgacgttctg catgaag                                            27

<210> SEQ ID NO 41
<211> LENGTH: 27
```

```
<212> TYPE: DNA
<213> ORGANISM: Artificial Sequence
<220> FEATURE:
<223> OTHER INFORMATION: S. saprophyticus femA capture sequence

<400> SEQUENCE: 41
acttaatact tcgcgttcag cctttaa                                    27

<210> SEQ ID NO 42
<211> LENGTH: 27
<212> TYPE: DNA
<213> ORGANISM: Artificial Sequence
<220> FEATURE:
<223> OTHER INFORMATION: S. capitis femA capture sequence

<400> SEQUENCE: 42
attaagaaca tctctttcat tattaag                                    27

<210> SEQ ID NO 43
<211> LENGTH: 24
<212> TYPE: DNA
<213> ORGANISM: Artificial Sequence
<220> FEATURE:
<223> OTHER INFORMATION: S. caseolyticus femA capture sequence

<400> SEQUENCE: 43
ataaagacat tcgagacgaa ggct                                       24

<210> SEQ ID NO 44
<211> LENGTH: 27
<212> TYPE: DNA
<213> ORGANISM: Artificial Sequence
<220> FEATURE:
<223> OTHER INFORMATION: S. cohnii femA capture sequence

<400> SEQUENCE: 44
acttaacact tcacgctctg acttgag                                    27

<210> SEQ ID NO 45
<211> LENGTH: 27
<212> TYPE: DNA
<213> ORGANISM: Artificial Sequence
<220> FEATURE:
<223> OTHER INFORMATION: S. gallinarum femA capture sequence

<400> SEQUENCE: 45
acttaaaact tcacgttcag cagtaag                                    27

<210> SEQ ID NO 46
<211> LENGTH: 27
<212> TYPE: DNA
<213> ORGANISM: Artificial Sequence
<220> FEATURE:
<223> OTHER INFORMATION: S. intermedius femA capture sequence

<400> SEQUENCE: 46
gtggaaatct tgctcttcag atttcag                                    27

<210> SEQ ID NO 47
<211> LENGTH: 27
<212> TYPE: DNA
<213> ORGANISM: Artificial Sequence
<220> FEATURE:
<223> OTHER INFORMATION: S. lugdunensis femA capture sequence

<400> SEQUENCE: 47
```

```
ttctaaagtt tgtcgttcat tcgttag                                              27
```

<210> SEQ ID NO 48
<211> LENGTH: 27
<212> TYPE: DNA
<213> ORGANISM: Artificial Sequence
<220> FEATURE:
<223> OTHER INFORMATION: S. schleiferi femA capture sequence

<400> SEQUENCE: 48

```
tttaaagtct tgcgcttcag tgttgag                                              27
```

<210> SEQ ID NO 49
<211> LENGTH: 27
<212> TYPE: DNA
<213> ORGANISM: Artificial Sequence
<220> FEATURE:
<223> OTHER INFORMATION: S. sciuri femA capture sequence

<400> SEQUENCE: 49

```
gttgtattgt tcatgttctt tttctaa                                              27
```

<210> SEQ ID NO 50
<211> LENGTH: 27
<212> TYPE: DNA
<213> ORGANISM: Artificial Sequence
<220> FEATURE:
<223> OTHER INFORMATION: S. simulans femA capture sequence

<400> SEQUENCE: 50

```
ttctaaattc ttttgttcag cgttcaa                                              27
```

<210> SEQ ID NO 51
<211> LENGTH: 27
<212> TYPE: DNA
<213> ORGANISM: Artificial Sequence
<220> FEATURE:
<223> OTHER INFORMATION: S. warneri femA capture sequence

<400> SEQUENCE: 51

```
agttaaggtt tcttttcat tattgag                                               27
```

<210> SEQ ID NO 52
<211> LENGTH: 27
<212> TYPE: DNA
<213> ORGANISM: Artificial Sequence
<220> FEATURE:
<223> OTHER INFORMATION: S. xylosis femA capture sequence

<400> SEQUENCE: 52

```
gcttaacacc tcacgttgag cttgcaa                                              27
```

<210> SEQ ID NO 53
<211> LENGTH: 20
<212> TYPE: DNA
<213> ORGANISM: Artificial Sequence
<220> FEATURE:
<223> OTHER INFORMATION: consensus primer MycU4 sense

<400> SEQUENCE: 53

```
catgcagtga attagaacgt                                                      20
```

<210> SEQ ID NO 54
<211> LENGTH: 18
<212> TYPE: DNA
<213> ORGANISM: Artificial Sequence

```
<220> FEATURE:
<223> OTHER INFORMATION: consensus primer APmcon02 antisense

<400> SEQUENCE: 54
gtasgtcatr rstyctcc                                                 18

<210> SEQ ID NO 55
<211> LENGTH: 21
<212> TYPE: DNA
<213> ORGANISM: Artificial Sequence
<220> FEATURE:
<223> OTHER INFORMATION: Mycobacteria avium capture probe

<400> SEQUENCE: 55
cggtcgtctc cgaagcccgc g                                             21

<210> SEQ ID NO 56
<211> LENGTH: 20
<212> TYPE: DNA
<213> ORGANISM: Artificial Sequence
<220> FEATURE:
<223> OTHER INFORMATION: Mycobacteria gastrii 1 capture probe

<400> SEQUENCE: 56
gatcggcagc ggtgccgggg                                               20

<210> SEQ ID NO 57
<211> LENGTH: 19
<212> TYPE: DNA
<213> ORGANISM: Artificial Sequence
<220> FEATURE:
<223> OTHER INFORMATION: Mycobacteria gastrii 3 capture probe

<400> SEQUENCE: 57
gtatcgcggg cggcaaggt                                                19

<210> SEQ ID NO 58
<211> LENGTH: 24
<212> TYPE: DNA
<213> ORGANISM: Artificial Sequence
<220> FEATURE:
<223> OTHER INFORMATION: Mycobacteria gastrii 5 capture probe

<400> SEQUENCE: 58
tctgccgatc ggcagcggtg ccgg                                          24

<210> SEQ ID NO 59
<211> LENGTH: 24
<212> TYPE: DNA
<213> ORGANISM: Artificial Sequence
<220> FEATURE:
<223> OTHER INFORMATION: Mycobacteria gastrii 7 capture probe

<400> SEQUENCE: 59
gccggggccg gtattcgcgg gcgg                                          24

<210> SEQ ID NO 60
<211> LENGTH: 22
<212> TYPE: DNA
<213> ORGANISM: Artificial Sequence
<220> FEATURE:
<223> OTHER INFORMATION: Mycobacteria gordonae capture probe

<400> SEQUENCE: 60
gacgggcact agttgtcaga gg                                            22
```

<210> SEQ ID NO 61
<211> LENGTH: 21
<212> TYPE: DNA
<213> ORGANISM: Artificial Sequence
<220> FEATURE:
<223> OTHER INFORMATION: Mycobacterium intracellulare 1 capture probe

<400> SEQUENCE: 61
gggccgccgg gggcctcgcc g                                              21

<210> SEQ ID NO 62
<211> LENGTH: 21
<212> TYPE: DNA
<213> ORGANISM: Artificial Sequence
<220> FEATURE:
<223> OTHER INFORMATION: Mycobacterium intracellulare 3 capture probe

<400> SEQUENCE: 62
gcctcgccgc ccaagacagt g                                              21

<210> SEQ ID NO 63
<211> LENGTH: 21
<212> TYPE: DNA
<213> ORGANISM: Artificial Sequence
<220> FEATURE:
<223> OTHER INFORMATION: Mycobacterium leprae capture probe

<400> SEQUENCE: 63
gatttcggcg tccatcggtg g                                              21

<210> SEQ ID NO 64
<211> LENGTH: 21
<212> TYPE: DNA
<213> ORGANISM: Artificial Sequence
<220> FEATURE:
<223> OTHER INFORMATION: Mycobacterium kansasi 1 capture probe

<400> SEQUENCE: 64
gatcgtcggc agtggtgacg g                                              21

<210> SEQ ID NO 65
<211> LENGTH: 17
<212> TYPE: DNA
<213> ORGANISM: Artificial Sequence
<220> FEATURE:
<223> OTHER INFORMATION: Mycobacterium kansasi 3 capture probe

<400> SEQUENCE: 65
tcgtcggcag tggtgac                                                   17

<210> SEQ ID NO 66
<211> LENGTH: 27
<212> TYPE: DNA
<213> ORGANISM: Artificial Sequence
<220> FEATURE:
<223> OTHER INFORMATION: Mycobacterium kansasi 5 capture probe

<400> SEQUENCE: 66
atccgccgat cgtcggcagt ggtgacg                                        27

<210> SEQ ID NO 67
<211> LENGTH: 21
<212> TYPE: DNA
<213> ORGANISM: Artificial Sequence
<220> FEATURE:
<223> OTHER INFORMATION: Mycobacterium malmoense capture probe

<400> SEQUENCE: 67
gacccacaac actggtcggc g                21

<210> SEQ ID NO 68
<211> LENGTH: 21
<212> TYPE: DNA
<213> ORGANISM: Artificial Sequence
<220> FEATURE:
<223> OTHER INFORMATION: Mycobacterium marinum capture probe

<400> SEQUENCE: 68
cggaggtgat ggcgctggtc g                21

<210> SEQ ID NO 69
<211> LENGTH: 20
<212> TYPE: DNA
<213> ORGANISM: Artificial Sequence
<220> FEATURE:
<223> OTHER INFORMATION: Mycobacterium scrofulaceum  capture probe

<400> SEQUENCE: 69
cggcggcacg gatcggcgtc                20

<210> SEQ ID NO 70
<211> LENGTH: 20
<212> TYPE: DNA
<213> ORGANISM: Artificial Sequence
<220> FEATURE:
<223> OTHER INFORMATION: Mycobacterium simiae capture probe

<400> SEQUENCE: 70
atcgctcctg gtcgcgccta                20

<210> SEQ ID NO 71
<211> LENGTH: 21
<212> TYPE: DNA
<213> ORGANISM: Artificial Sequence
<220> FEATURE:
<223> OTHER INFORMATION: Mycobacterium szulgai capture probe

<400> SEQUENCE: 71
cccggcgcga ccagcagaac g                21

<210> SEQ ID NO 72
<211> LENGTH: 22
<212> TYPE: DNA
<213> ORGANISM: Artificial Sequence
<220> FEATURE:
<223> OTHER INFORMATION: Mycobacterium tuberculosis capture probe

<400> SEQUENCE: 72
gccgtccagt cgttaatgtc gc                22

<210> SEQ ID NO 73
<211> LENGTH: 22
<212> TYPE: DNA
<213> ORGANISM: Artificial Sequence
<220> FEATURE:
<223> OTHER INFORMATION: Mycobacterium xenopi capture probe

<400> SEQUENCE: 73
cggtagaagc tgcgatgaca cg                22

<210> SEQ ID NO 74

```
<211> LENGTH: 45
<212> TYPE: DNA
<213> ORGANISM: Artificial Sequence
<220> FEATURE:
<223> OTHER INFORMATION: Spacer Sequence

<400> SEQUENCE: 74
gaattcaaag ttgctgagaa tagttcaatg gaaggaagcg tcttc              45

<210> SEQ ID NO 75
<211> LENGTH: 24
<212> TYPE: DNA
<213> ORGANISM: Artificial Sequence
<220> FEATURE:
<223> OTHER INFORMATION: consensus primer DPSCONS2 sense

<400> SEQUENCE: 75
gggctccagc agccaagaag agga                                      24

<210> SEQ ID NO 76
<211> LENGTH: 24
<212> TYPE: DNA
<213> ORGANISM: Artificial Sequence
<220> FEATURE:
<223> OTHER INFORMATION: consensus primer DPSMAGE1 sense

<400> SEQUENCE: 76
gggttccagc agccgtgaag agga                                      24

<210> SEQ ID NO 77
<211> LENGTH: 24
<212> TYPE: DNA
<213> ORGANISM: Artificial Sequence
<220> FEATURE:
<223> OTHER INFORMATION: consensus primer DPSMAG8 sense

<400> SEQUENCE: 77
gggttccagc agcaatgaag agga                                      24

<210> SEQ ID NO 78
<211> LENGTH: 24
<212> TYPE: DNA
<213> ORGANISM: Artificial Sequence
<220> FEATURE:
<223> OTHER INFORMATION: consensus primer DPSMAG12 sense

<400> SEQUENCE: 78
gggctccagc aacgaagaac agga                                      24

<210> SEQ ID NO 79
<211> LENGTH: 24
<212> TYPE: DNA
<213> ORGANISM: Artificial Sequence
<220> FEATURE:
<223> OTHER INFORMATION: consensus primer DPASCONB4 antisense

<400> SEQUENCE: 79
cggtactcca ggtagttttc ctgc                                      24

<210> SEQ ID NO 80
<211> LENGTH: 27
<212> TYPE: DNA
<213> ORGANISM: Artificial Sequence
<220> FEATURE:
<223> OTHER INFORMATION: capture probe Mage 1 DTAS01

<400> SEQUENCE: 80
```

```
acaaggactc caggatacaa gaggtgc                                          27

<210> SEQ ID NO 81
<211> LENGTH: 27
<212> TYPE: DNA
<213> ORGANISM: Artificial Sequence
<220> FEATURE:
<223> OTHER INFORMATION: capture probe Mage 2 DTAS02

<400> SEQUENCE: 81
actcggactc caggtcggga aacattc                                          27

<210> SEQ ID NO 82
<211> LENGTH: 27
<212> TYPE: DNA
<213> ORGANISM: Artificial Sequence
<220> FEATURE:
<223> OTHER INFORMATION: capture probe Mage 3 DTS0306

<400> SEQUENCE: 82
aagacagtat cttgggggat cccaaga                                          27

<210> SEQ ID NO 83
<211> LENGTH: 27
<212> TYPE: DNA
<213> ORGANISM: Artificial Sequence
<220> FEATURE:
<223> OTHER INFORMATION: capture probe Mage 4 DTAS04

<400> SEQUENCE: 83
tcggaacaag gactctgcgt caggcga                                          27

<210> SEQ ID NO 84
<211> LENGTH: 27
<212> TYPE: DNA
<213> ORGANISM: Artificial Sequence
<220> FEATURE:
<223> OTHER INFORMATION: capture probe Mage 5 DTAS05

<400> SEQUENCE: 84
gctcggaaca cagactctgg gtcaggg                                          27

<210> SEQ ID NO 85
<211> LENGTH: 27
<212> TYPE: DNA
<213> ORGANISM: Artificial Sequence
<220> FEATURE:
<223> OTHER INFORMATION: capture probe Mage 6 DTS06

<400> SEQUENCE: 85
caagacaggc ttcctgataa tcatcct                                          27

<210> SEQ ID NO 86
<211> LENGTH: 27
<212> TYPE: DNA
<213> ORGANISM: Artificial Sequence
<220> FEATURE:
<223> OTHER INFORMATION: capture probe Mage 7 DTAS07

<400> SEQUENCE: 86
aggacgccag gtgagcgggg tgtgtct                                          27

<210> SEQ ID NO 87
<211> LENGTH: 27
<212> TYPE: DNA
```

```
<213> ORGANISM: Artificial Sequence
<220> FEATURE:
<223> OTHER INFORMATION: capture probe Mage 8 DTAS08

<400> SEQUENCE: 87
gggactccag gtgagctggg tccgggg                                              27

<210> SEQ ID NO 88
<211> LENGTH: 27
<212> TYPE: DNA
<213> ORGANISM: Artificial Sequence
<220> FEATURE:
<223> OTHER INFORMATION: capture probe Mage 9 DTAS09

<400> SEQUENCE: 88
tgaactccag ctgagctggg tcgaccg                                              27

<210> SEQ ID NO 89
<211> LENGTH: 27
<212> TYPE: DNA
<213> ORGANISM: Artificial Sequence
<220> FEATURE:
<223> OTHER INFORMATION: capture probe Mage 10 DTAS10

<400> SEQUENCE: 89
tgggtaaaga ctcactgtct ggcagga                                              27

<210> SEQ ID NO 90
<211> LENGTH: 27
<212> TYPE: DNA
<213> ORGANISM: Artificial Sequence
<220> FEATURE:
<223> OTHER INFORMATION: capture probe Mage 11 DTAS11

<400> SEQUENCE: 90
gaaaaggact cagggtctat caggtca                                              27

<210> SEQ ID NO 91
<211> LENGTH: 27
<212> TYPE: DNA
<213> ORGANISM: Artificial Sequence
<220> FEATURE:
<223> OTHER INFORMATION: capture probe Mage 12 DTAS12

<400> SEQUENCE: 91
gtgctacttg gaagctcgtc tccaggt                                              27

<210> SEQ ID NO 92
<211> LENGTH: 22
<212> TYPE: DNA
<213> ORGANISM: Artificial Sequence
<220> FEATURE:
<223> OTHER INFORMATION: consensus primer CONSENSUS2-3-4 sense

<400> SEQUENCE: 92
tgcagacmac caccaactac tt                                                   22

<210> SEQ ID NO 93
<211> LENGTH: 22
<212> TYPE: DNA
<213> ORGANISM: Artificial Sequence
<220> FEATURE:
<223> OTHER INFORMATION: consensus primer CONSENSUS1-5 sense

<400> SEQUENCE: 93
tgmggkccaa gatgaccaac wt                                                   22
```

<210> SEQ ID NO 94
<211> LENGTH: 22
<212> TYPE: DNA
<213> ORGANISM: Artificial Sequence
<220> FEATURE:
<223> OTHER INFORMATION: consensus primer CONSENSUS1-5 antisense

<400> SEQUENCE: 94
tcatgrcrca saggttcagg at                                              22

<210> SEQ ID NO 95
<211> LENGTH: 27
<212> TYPE: DNA
<213> ORGANISM: Artificial Sequence
<220> FEATURE:
<223> OTHER INFORMATION: capture probe DRD1

<400> SEQUENCE: 95
ctggcttttg gcctttgggt ccctttt                                         27

<210> SEQ ID NO 96
<211> LENGTH: 27
<212> TYPE: DNA
<213> ORGANISM: Artificial Sequence
<220> FEATURE:
<223> OTHER INFORMATION: capture probe DRD2

<400> SEQUENCE: 96
tgattggaaa ttcagcagga ttcactg                                         27

<210> SEQ ID NO 97
<211> LENGTH: 27
<212> TYPE: DNA
<213> ORGANISM: Artificial Sequence
<220> FEATURE:
<223> OTHER INFORMATION: capture probe DRD3

<400> SEQUENCE: 97
gagtctggaa tttcagccgc atttgct                                         27

<210> SEQ ID NO 98
<211> LENGTH: 27
<212> TYPE: DNA
<213> ORGANISM: Artificial Sequence
<220> FEATURE:
<223> OTHER INFORMATION: capture probe DRD4

<400> SEQUENCE: 98
cgtctggctg ctgagccccc gcctctg                                         27

<210> SEQ ID NO 99
<211> LENGTH: 27
<212> TYPE: DNA
<213> ORGANISM: Artificial Sequence
<220> FEATURE:
<223> OTHER INFORMATION: capture probe DRD5

<400> SEQUENCE: 99
ctgggtactg gcccttrggg acattct                                         27

<210> SEQ ID NO 100
<211> LENGTH: 18
<212> TYPE: DNA
<213> ORGANISM: Artificial Sequence
<220> FEATURE:

```
<223> OTHER INFORMATION: primer H1sense

<400> SEQUENCE: 100
ctccgtccag caacccct                                              18

<210> SEQ ID NO 101
<211> LENGTH: 19
<212> TYPE: DNA
<213> ORGANISM: Artificial Sequence
<220> FEATURE:
<223> OTHER INFORMATION: primer H2sense

<400> SEQUENCE: 101
ctgtgctggt caccccagt                                             19

<210> SEQ ID NO 102
<211> LENGTH: 21
<212> TYPE: DNA
<213> ORGANISM: Artificial Sequence
<220> FEATURE:
<223> OTHER INFORMATION: primer H3sense

<400> SEQUENCE: 102
actcatcagc tatgaccgat t                                          21

<210> SEQ ID NO 103
<211> LENGTH: 20
<212> TYPE: DNA
<213> ORGANISM: Artificial Sequence
<220> FEATURE:
<223> OTHER INFORMATION: primer H1antisense

<400> SEQUENCE: 103
accttccttg gtatcgtctg                                            20

<210> SEQ ID NO 104
<211> LENGTH: 21
<212> TYPE: DNA
<213> ORGANISM: Artificial Sequence
<220> FEATURE:
<223> OTHER INFORMATION: primer H2 antisense

<400> SEQUENCE: 104
gaaaccagca gatgatgaac g                                          21

<210> SEQ ID NO 105
<211> LENGTH: 19
<212> TYPE: DNA
<213> ORGANISM: Artificial Sequence
<220> FEATURE:
<223> OTHER INFORMATION: primer H3 antisense

<400> SEQUENCE: 105
gcatctggtg ggggttctg                                             19

<210> SEQ ID NO 106
<211> LENGTH: 18
<212> TYPE: DNA
<213> ORGANISM: Artificial Sequence
<220> FEATURE:
<223> OTHER INFORMATION: capture probe H1

<400> SEQUENCE: 106
ccccaggatg gtagcgga                                              18
```

```
<210> SEQ ID NO 107
<211> LENGTH: 22
<212> TYPE: DNA
<213> ORGANISM: Artificial Sequence
<220> FEATURE:
<223> OTHER INFORMATION: capture probe H2

<400> SEQUENCE: 107
aggatagggt gatagaaata ac                                              22

<210> SEQ ID NO 108
<211> LENGTH: 18
<212> TYPE: DNA
<213> ORGANISM: Artificial Sequence
<220> FEATURE:
<223> OTHER INFORMATION: capture probe H3

<400> SEQUENCE: 108
tctcgtgtcc ccctgctg                                                   18

<210> SEQ ID NO 109
<211> LENGTH: 20
<212> TYPE: DNA
<213> ORGANISM: Artificial Sequence
<220> FEATURE:
<223> OTHER INFORMATION: general consensus primer sequence for subtypes
      1A, 1B, 1C, 1D, 1E, 2A, 2B, 2C, 4, 6, and 7 sense

<400> SEQUENCE: 109
atchtgcacc tstgbgbcat                                                 20

<210> SEQ ID NO 110
<211> LENGTH: 20
<212> TYPE: DNA
<213> ORGANISM: Artificial Sequence
<220> FEATURE:
<223> OTHER INFORMATION: consensus primer for subtype 1A sense

<400> SEQUENCE: 110
atcctgcacc tgtgcgccat                                                 20

<210> SEQ ID NO 111
<211> LENGTH: 20
<212> TYPE: DNA
<213> ORGANISM: Artificial Sequence
<220> FEATURE:
<223> OTHER INFORMATION: consensus primer for subtype 1B sense

<400> SEQUENCE: 111
atcatgcatc tctgtgtcat                                                 20

<210> SEQ ID NO 112
<211> LENGTH: 20
<212> TYPE: DNA
<213> ORGANISM: Artificial Sequence
<220> FEATURE:
<223> OTHER INFORMATION: consensus primer for subtype 1C sense

<400> SEQUENCE: 112
atcatgcacc tctgcgccat                                                 20

<210> SEQ ID NO 113
<211> LENGTH: 20
<212> TYPE: DNA
<213> ORGANISM: Artificial Sequence
<220> FEATURE:
<223> OTHER INFORMATION: consensus primer for subtype 1D sense
```

```
<400> SEQUENCE: 113
atcctgcatc tctgtgtcat                                              20

<210> SEQ ID NO 114
<211> LENGTH: 20
<212> TYPE: DNA
<213> ORGANISM: Artificial Sequence
<220> FEATURE:
<223> OTHER INFORMATION: consensus primer for subtype 1E sense

<400> SEQUENCE: 114
atcttgcacc tgtcggctat                                              20

<210> SEQ ID NO 115
<211> LENGTH: 20
<212> TYPE: DNA
<213> ORGANISM: Artificial Sequence
<220> FEATURE:
<223> OTHER INFORMATION: consensus primer for subtype 2A sense

<400> SEQUENCE: 115
atcatgcacc tctgcgccat                                              20

<210> SEQ ID NO 116
<211> LENGTH: 20
<212> TYPE: DNA
<213> ORGANISM: Artificial Sequence
<220> FEATURE:
<223> OTHER INFORMATION: consensus primer for subtype 2B sense

<400> SEQUENCE: 116
atcatgcatc tctgtgccat                                              20

<210> SEQ ID NO 117
<211> LENGTH: 20
<212> TYPE: DNA
<213> ORGANISM: Artificial Sequence
<220> FEATURE:
<223> OTHER INFORMATION: consensus primer for subtype 2C sense

<400> SEQUENCE: 117
atcatgcacc tctgcgccat                                              20

<210> SEQ ID NO 118
<211> LENGTH: 20
<212> TYPE: DNA
<213> ORGANISM: Artificial Sequence
<220> FEATURE:
<223> OTHER INFORMATION: consensus primer for subtype 4 sense

<400> SEQUENCE: 118 attttttcacc tctgctgcat                                             20

<210> SEQ ID NO 119
<211> LENGTH: 20
<212> TYPE: DNA
<213> ORGANISM: Artificial Sequence
<220> FEATURE:
<223> OTHER INFORMATION: consensus primer for subtype 6 sense

<400> SEQUENCE: 119
atcctcaacc tctgcttcat                                              20

<210> SEQ ID NO 120
```

-continued

```
<211> LENGTH: 20
<212> TYPE: DNA
<213> ORGANISM: Artificial Sequence
<220> FEATURE:
<223> OTHER INFORMATION: consensus primer for subtype 7 sense

<400> SEQUENCE: 120
atcatgaccc tgtgcgtgat                                              20

<210> SEQ ID NO 121
<211> LENGTH: 20
<212> TYPE: DNA
<213> ORGANISM: Artificial Sequence
<220> FEATURE:
<223> OTHER INFORMATION: general consensus primer for 4, 6

<400> SEQUENCE: 121
atcytycacc tctgcykcat                                              20

<210> SEQ ID NO 122
<211> LENGTH: 20
<212> TYPE: DNA
<213> ORGANISM: Artificial Sequence
<220> FEATURE:
<223> OTHER INFORMATION: consensus primer for 4

<400> SEQUENCE: 122
atttttcacc tctgctgcat                                              20

<210> SEQ ID NO 123
<211> LENGTH: 20
<212> TYPE: DNA
<213> ORGANISM: Artificial Sequence
<220> FEATURE:
<223> OTHER INFORMATION: consensus primer for 6

<400> SEQUENCE: 123
atttttcacc tctgctgcat                                              20

<210> SEQ ID NO 124
<211> LENGTH: 20
<212> TYPE: DNA
<213> ORGANISM: Artificial Sequence
<220> FEATURE:
<223> OTHER INFORMATION: general consensus primer for 5A, 5B

<400> SEQUENCE: 124
atctggaayg tgrcagccat                                              20

<210> SEQ ID NO 125
<211> LENGTH: 20
<212> TYPE: DNA
<213> ORGANISM: Artificial Sequence
<220> FEATURE:
<223> OTHER INFORMATION: consensus primer for 5A

<400> SEQUENCE: 125
atctggaatg tgacagcaat                                              20

<210> SEQ ID NO 126
<211> LENGTH: 20
<212> TYPE: DNA
<213> ORGANISM: Artificial Sequence
<220> FEATURE:
<223> OTHER INFORMATION: consensus primer for 5B

<400> SEQUENCE: 126
```

```
atctggaacg tggcggccat                                              20
```

<210> SEQ ID NO 127
<211> LENGTH: 20
<212> TYPE: DNA
<213> ORGANISM: Artificial Sequence
<220> FEATURE:
<223> OTHER INFORMATION: consensus primer for Specific 7

<400> SEQUENCE: 127

```
atcatgaccc tgtgcgtgat                                              20
```

<210> SEQ ID NO 128
<211> LENGTH: 19
<212> TYPE: DNA
<213> ORGANISM: Artificial Sequence
<220> FEATURE:
<223> OTHER INFORMATION: consensus primer for Specific 3B

<400> SEQUENCE: 128

```
cttccggaac gattagaaa                                               19
```

<210> SEQ ID NO 129
<211> LENGTH: 17
<212> TYPE: DNA
<213> ORGANISM: Artificial Sequence
<220> FEATURE:
<223> OTHER INFORMATION: general consensus primer for Consensus subtypes
      1A, 1B, 1C, 1D, 1E, 2A, 2B, 2C, 4, 7
<221> NAME/KEY: misc_feature
<222> LOCATION: (1)...(17)
<223> OTHER INFORMATION: n = A,T,C or G

<400> SEQUENCE: 129

```
ttgghngcyt tcygbtc                                                 17
```

<210> SEQ ID NO 130
<211> LENGTH: 17
<212> TYPE: DNA
<213> ORGANISM: Artificial Sequence
<220> FEATURE:
<223> OTHER INFORMATION: consensus primer Consensus subtype 1A antisense

<400> SEQUENCE: 130

```
ttcaccgtct tcctttc                                                 17
```

<210> SEQ ID NO 131
<211> LENGTH: 17
<212> TYPE: DNA
<213> ORGANISM: Artificial Sequence
<220> FEATURE:
<223> OTHER INFORMATION: consensus primer for Consensus subtype 1B
      antisense

<400> SEQUENCE: 131

```
ttggtggctt tgcgctc                                                 17
```

<210> SEQ ID NO 132
<211> LENGTH: 17
<212> TYPE: DNA
<213> ORGANISM: Artificial Sequence
<220> FEATURE:
<223> OTHER INFORMATION: consensus primer for Consensus subtype 1C
      antisense

<400> SEQUENCE: 132
ttggaagctt tcttttc                                              17

<210> SEQ ID NO 133
<211> LENGTH: 17
<212> TYPE: DNA
<213> ORGANISM: Artificial Sequence
<220> FEATURE:
<223> OTHER INFORMATION: consensus primer for Consensus subtype 1D
      antisense

<400> SEQUENCE: 133
ttagtggctt tcctttc                                              17

<210> SEQ ID NO 134
<211> LENGTH: 17
<212> TYPE: DNA
<213> ORGANISM: Artificial Sequence
<220> FEATURE:
<223> OTHER INFORMATION: consensus primer for Consensus subtype 1E
      antisense

<400> SEQUENCE: 134
gtggctgctt tgcgttc                                              17

<210> SEQ ID NO 135
<211> LENGTH: 17
<212> TYPE: DNA
<213> ORGANISM: Artificial Sequence
<220> FEATURE:
<223> OTHER INFORMATION: consensus primer for Consensus subtype 2A
      antisense

<400> SEQUENCE: 135
ttgcacgcct tttgctc                                              17

<210> SEQ ID NO 136
<211> LENGTH: 17
<212> TYPE: DNA
<213> ORGANISM: Artificial Sequence
<220> FEATURE:
<223> OTHER INFORMATION: consensus primer for Consensus subtype 2B
      antisense

<400> SEQUENCE: 136
tttgaggctc tctgttc                                              17

<210> SEQ ID NO 137
<211> LENGTH: 17
<212> TYPE: DNA
<213> ORGANISM: Artificial Sequence
<220> FEATURE:
<223> OTHER INFORMATION: consensus primer for Consensus subtype 2C
      antisense

<400> SEQUENCE: 137
ttggaagctt tcttttc                                              17

<210> SEQ ID NO 138
<211> LENGTH: 17
<212> TYPE: DNA
<213> ORGANISM: Artificial Sequence
<220> FEATURE:
<223> OTHER INFORMATION: consensus primer for Consensus subtype 4
      antisense

<400> SEQUENCE: 138
ttggctgctt tccggtc                                              17

<210> SEQ ID NO 139
<211> LENGTH: 17
<212> TYPE: DNA
<213> ORGANISM: Artificial Sequence
<220> FEATURE:
<223> OTHER INFORMATION: consensus primer for Consensus subtype 7
      antisense

<400> SEQUENCE: 139
gtggctgctt tctgttc                                                 17

<210> SEQ ID NO 140
<211> LENGTH: 17
<212> TYPE: DNA
<213> ORGANISM: Artificial Sequence
<220> FEATURE:
<223> OTHER INFORMATION: consensus primer for Consensus Specific 1A
      antisense

<400> SEQUENCE: 140
ttcaccgtct tcctttc                                                 17

<210> SEQ ID NO 141
<211> LENGTH: 17
<212> TYPE: DNA
<213> ORGANISM: Artificial Sequence
<220> FEATURE:
<223> OTHER INFORMATION: consensus primer for Consensus Specific 4
      antisense

<400> SEQUENCE: 141
tcttggctgc tttggtc                                                 17

<210> SEQ ID NO 142
<211> LENGTH: 18
<212> TYPE: DNA
<213> ORGANISM: Artificial Sequence
<220> FEATURE:
<223> OTHER INFORMATION: consensus primer for Consensus Specific 6
      antisense

<400> SEQUENCE: 142
ataaagagcg ggtagatg                                                18

<210> SEQ ID NO 143
<211> LENGTH: 16
<212> TYPE: DNA
<213> ORGANISM: Artificial Sequence
<220> FEATURE:
<223> OTHER INFORMATION: consensus primer Consensus 5A,5B antisense

<400> SEQUENCE: 143
ccttctgctc cctcca                                                  16

<210> SEQ ID NO 144
<211> LENGTH: 16
<212> TYPE: DNA
<213> ORGANISM: Artificial Sequence
<220> FEATURE:
<223> OTHER INFORMATION: consensus primer for Consensus 5A antisense

<400> SEQUENCE: 144
ccttctgttc cctcca                                                  16

<210> SEQ ID NO 145

```
<211> LENGTH: 16
<212> TYPE: DNA
<213> ORGANISM: Artificial Sequence
<220> FEATURE:
<223> OTHER INFORMATION: consensus primer for Consensus 5B antisense

<400> SEQUENCE: 145
ccttctgctc ccgcca                                                     16

<210> SEQ ID NO 146
<211> LENGTH: 16
<212> TYPE: DNA
<213> ORGANISM: Artificial Sequence
<220> FEATURE:
<223> OTHER INFORMATION: consensus primer for Specific 3B antisense

<400> SEQUENCE: 146
accggggact ctgtgt                                                     16

<210> SEQ ID NO 147
<211> LENGTH: 21
<212> TYPE: DNA
<213> ORGANISM: Artificial Sequence
<220> FEATURE:
<223> OTHER INFORMATION: capture probe HTR1C

<400> SEQUENCE: 147
ctatgctcaa taggattacg t                                               21

<210> SEQ ID NO 148
<211> LENGTH: 19
<212> TYPE: DNA
<213> ORGANISM: Artificial Sequence
<220> FEATURE:
<223> OTHER INFORMATION: capture probe HTR2A

<400> SEQUENCE: 148
gtggtgaatg gggttctgg                                                  19

<210> SEQ ID NO 149
<211> LENGTH: 21
<212> TYPE: DNA
<213> ORGANISM: Artificial Sequence
<220> FEATURE:
<223> OTHER INFORMATION: capture probe HTR2B

<400> SEQUENCE: 149
tggcctgaat tggctttttg a                                               21

<210> SEQ ID NO 150
<211> LENGTH: 22
<212> TYPE: DNA
<213> ORGANISM: Artificial Sequence
<220> FEATURE:
<223> OTHER INFORMATION: capture probe HTR2C/1C

<400> SEQUENCE: 150
ttattcacga acactttgct tt                                              22

<210> SEQ ID NO 151
<211> LENGTH: 20
<212> TYPE: DNA
<213> ORGANISM: Artificial Sequence
<220> FEATURE:
<223> OTHER INFORMATION: capture probe HTR1B

<400> SEQUENCE: 151
```

```
aatagtccac cgcatcagtg                                              20

<210> SEQ ID NO 152
<211> LENGTH: 19
<212> TYPE: DNA
<213> ORGANISM: Artificial Sequence
<220> FEATURE:
<223> OTHER INFORMATION: capture probe HTR1D

<400> SEQUENCE: 152
gtactccagg gcatcggtg                                               19

<210> SEQ ID NO 153
<211> LENGTH: 20
<212> TYPE: DNA
<213> ORGANISM: Artificial Sequence
<220> FEATURE:
<223> OTHER INFORMATION: capture probe HTR1A

<400> SEQUENCE: 153
catagtctat agggtcggtg                                              20

<210> SEQ ID NO 154
<211> LENGTH: 20
<212> TYPE: DNA
<213> ORGANISM: Artificial Sequence
<220> FEATURE:
<223> OTHER INFORMATION: capture probe HTR1E

<400> SEQUENCE: 154
atactcgact gcgtctgtga                                              20

<210> SEQ ID NO 155
<211> LENGTH: 19
<212> TYPE: DNA
<213> ORGANISM: Artificial Sequence
<220> FEATURE:
<223> OTHER INFORMATION: capture probe HTR7

<400> SEQUENCE: 155
gtacgtgagg ggtctcgtg                                               19

<210> SEQ ID NO 156
<211> LENGTH: 19
<212> TYPE: DNA
<213> ORGANISM: Artificial Sequence
<220> FEATURE:
<223> OTHER INFORMATION: capture probe HTR5A

<400> SEQUENCE: 156
ggcgcgttat tgaccagta                                               19

<210> SEQ ID NO 157
<211> LENGTH: 18
<212> TYPE: DNA
<213> ORGANISM: Artificial Sequence
<220> FEATURE:
<223> OTHER INFORMATION: capture probe HTR5B

<400> SEQUENCE: 157
ggcgcgtgat agtccagt                                                18

<210> SEQ ID NO 158
<211> LENGTH: 21
<212> TYPE: DNA
```

```
<213> ORGANISM: Artificial Sequence
<220> FEATURE:
<223> OTHER INFORMATION: capture probe HTR3B

<400> SEQUENCE: 158
gatatcaaag gggaaagcgt a                                            21

<210> SEQ ID NO 159
<211> LENGTH: 20
<212> TYPE: DNA
<213> ORGANISM: Artificial Sequence
<220> FEATURE:
<223> OTHER INFORMATION: capture probe HTR4

<400> SEQUENCE: 159
aaaccaaagg ttgacagcag                                              20

<210> SEQ ID NO 160
<211> LENGTH: 18
<212> TYPE: DNA
<213> ORGANISM: Artificial Sequence
<220> FEATURE:
<223> OTHER INFORMATION: capture probe HTR6

<400> SEQUENCE: 160
gtagcgcagc ggcgagag                                                18

<210> SEQ ID NO 161
<211> LENGTH: 20
<212> TYPE: DNA
<213> ORGANISM: Artificial Sequence
<220> FEATURE:
<223> OTHER INFORMATION: consensus primer IPSCONA sense

<400> SEQUENCE: 161
gacagcgacg ccgcgagcca                                              20

<210> SEQ ID NO 162
<211> LENGTH: 22
<212> TYPE: DNA
<213> ORGANISM: Artificial Sequence
<220> FEATURE:
<223> OTHER INFORMATION: consensus primer IPASCONA antisense

<400> SEQUENCE: 162
cgtgtcctgg gtctggtcct cc                                           22

<210> SEQ ID NO 163
<211> LENGTH: 27
<212> TYPE: DNA
<213> ORGANISM: Artificial Sequence
<220> FEATURE:
<223> OTHER INFORMATION: capture probe HLA-A1 ITSA01

<400> SEQUENCE: 163
ggagggccgg tgcgtggacg ggctccg                                      27

<210> SEQ ID NO 164
<211> LENGTH: 27
<212> TYPE: DNA
<213> ORGANISM: Artificial Sequence
<220> FEATURE:
<223> OTHER INFORMATION: capture probe HLA-A2 ITASA02

<400> SEQUENCE: 164
tctccccgtc ccaatactcc ggaccct                                      27
```

<210> SEQ ID NO 165
<211> LENGTH: 27
<212> TYPE: DNA
<213> ORGANISM: Artificial Sequence
<220> FEATURE:
<223> OTHER INFORMATION: capture probe HLA-A3 ITASA03A

<400> SEQUENCE: 165
ctgggccttc acattccgtg tctcctg                27

<210> SEQ ID NO 166
<211> LENGTH: 27
<212> TYPE: DNA
<213> ORGANISM: Artificial Sequence
<220> FEATURE:
<223> OTHER INFORMATION: capture probe HLA-A3 ITSA03B

<400> SEQUENCE: 166
agcgcaagtg ggaggcggcc catgagg                27

<210> SEQ ID NO 167
<211> LENGTH: 27
<212> TYPE: DNA
<213> ORGANISM: Artificial Sequence
<220> FEATURE:
<223> OTHER INFORMATION: capture probe HLA-A11 ITSA11A

<400> SEQUENCE: 167
gcccatgcgg cggagcagca gagagcc                27

<210> SEQ ID NO 168
<211> LENGTH: 27
<212> TYPE: DNA
<213> ORGANISM: Artificial Sequence
<220> FEATURE:
<223> OTHER INFORMATION: capture probe HLA-A11 ITSA11B

<400> SEQUENCE: 168
cctggagggc cggtgcgtgg agtggct                27

<210> SEQ ID NO 169
<211> LENGTH: 27
<212> TYPE: DNA
<213> ORGANISM: Artificial Sequence
<220> FEATURE:
<223> OTHER INFORMATION: capture probe HLA-A23 ITSA23A

<400> SEQUENCE: 169
gcccgtgtgg cggagcagtt gagagcc                27

<210> SEQ ID NO 170
<211> LENGTH: 27
<212> TYPE: DNA
<213> ORGANISM: Artificial Sequence
<220> FEATURE:
<223> OTHER INFORMATION: capture probe HLA-A23 ITASA23B

<400> SEQUENCE: 170 ccttcactttt ccctgtctcc tcgtccc                27

<210> SEQ ID NO 171
<211> LENGTH: 27
<212> TYPE: DNA
<213> ORGANISM: Artificial Sequence
<220> FEATURE:

-continued

<223> OTHER INFORMATION: capture probe HLA-A24 ITSA24A

<400> SEQUENCE: 171
gcccatgtgg cggagcagca gagagcc                                27

<210> SEQ ID NO 172
<211> LENGTH: 27
<212> TYPE: DNA
<213> ORGANISM: Artificial Sequence
<220> FEATURE:
<223> OTHER INFORMATION: capture probe HLA-A24 ITASA24B

<400> SEQUENCE: 172
tagcggagcg cgatccgcag gttctct                                27

<210> SEQ ID NO 173
<211> LENGTH: 27
<212> TYPE: DNA
<213> ORGANISM: Artificial Sequence
<220> FEATURE:
<223> OTHER INFORMATION: capture probe HLA-A25 ITASA25A

<400> SEQUENCE: 173
tagcggagcg cgatccgcag gctctct                                27

<210> SEQ ID NO 174
<211> LENGTH: 27
<212> TYPE: DNA
<213> ORGANISM: Artificial Sequence
<220> FEATURE:
<223> OTHER INFORMATION: capture probe HLA-A25 ITASA25B

<400> SEQUENCE: 174
tcacattccg tgtgttccgg tcccaat                                27

<210> SEQ ID NO 175
<211> LENGTH: 27
<212> TYPE: DNA
<213> ORGANISM: Artificial Sequence
<220> FEATURE:
<223> OTHER INFORMATION: capture probe HLA-A26 ITASA26

<400> SEQUENCE: 175
gggtccccag gttcgctcgg tcagtct                                27

<210> SEQ ID NO 176
<211> LENGTH: 27
<212> TYPE: DNA
<213> ORGANISM: Artificial Sequence
<220> FEATURE:
<223> OTHER INFORMATION: capture probe HLA-A29 ITASA29

<400> SEQUENCE: 176
tcacattccg tgtctgcagg tcccaat                                27

<210> SEQ ID NO 177
<211> LENGTH: 27
<212> TYPE: DNA
<213> ORGANISM: Artificial Sequence
<220> FEATURE:
<223> OTHER INFORMATION: capture probe HLA-A30 ITASA30

<400> SEQUENCE: 177
cgtaggcgtg ctgttcatac ccgcgga                                27

<210> SEQ ID NO 178
<211> LENGTH: 27
<212> TYPE: DNA
<213> ORGANISM: Artificial Sequence
<220> FEATURE:
<223> OTHER INFORMATION: capture probe HLA-A31 ITASA31

<400> SEQUENCE: 178
cccaatactc aggcctctcc tgctcta                                   27

<210> SEQ ID NO 179
<211> LENGTH: 27
<212> TYPE: DNA
<213> ORGANISM: Artificial Sequence
<220> FEATURE:
<223> OTHER INFORMATION: capture probe HLA-A33 ITSA33

<400> SEQUENCE: 179
cgcacggacc cccccaggac gcatatg                                   27

<210> SEQ ID NO 180
<211> LENGTH: 27
<212> TYPE: DNA
<213> ORGANISM: Artificial Sequence
<220> FEATURE:
<223> OTHER INFORMATION: capture probe HLA-A68 ITSA68A

<400> SEQUENCE: 180
ggcggcccat gtggcggagc agtggag                                   27

<210> SEQ ID NO 181
<211> LENGTH: 27
<212> TYPE: DNA
<213> ORGANISM: Artificial Sequence
<220> FEATURE:
<223> OTHER INFORMATION: capture probe HLA-A68 ITASA68B

<400> SEQUENCE: 181
gtcgtaggcg tcctgccggt acccgcg                                   27

<210> SEQ ID NO 182
<211> LENGTH: 27
<212> TYPE: DNA
<213> ORGANISM: Artificial Sequence
<220> FEATURE:
<223> OTHER INFORMATION: capture probe HLA-A69 ITASA69

<400> SEQUENCE: 182
atcctctgga cggtgtgaga accggcc                                   27

<210> SEQ ID NO 183
<211> LENGTH: 15
<212> TYPE: DNA
<213> ORGANISM: Artificial Sequence
<220> FEATURE:
<223> OTHER INFORMATION: sense primer for cytochrome P450

<400> SEQUENCE: 183
gccagagcct gagga                                                15

<210> SEQ ID NO 184
<211> LENGTH: 20
<212> TYPE: DNA
<213> ORGANISM: Artificial Sequence
<220> FEATURE:
<223> OTHER INFORMATION: primer consensus a3, a23, a1, a2  antisense

<400> SEQUENCE: 184
tcaaaagaaa ttaacagaga                                                    20

<210> SEQ ID NO 185
<211> LENGTH: 19
<212> TYPE: DNA
<213> ORGANISM: Artificial Sequence
<220> FEATURE:
<223> OTHER INFORMATION: primer Specific a9  antisense

<400> SEQUENCE: 185
acaatgaagg taacatagg                                                     19

<210> SEQ ID NO 186
<211> LENGTH: 18
<212> TYPE: DNA
<213> ORGANISM: Artificial Sequence
<220> FEATURE:
<223> OTHER INFORMATION: primer Specific a18  antisense

<400> SEQUENCE: 186
actgatggaa ctaactgg                                                      18

<210> SEQ ID NO 187
<211> LENGTH: 23
<212> TYPE: DNA
<213> ORGANISM: Artificial Sequence
<220> FEATURE:
<223> OTHER INFORMATION: capture probe 3a1

<400> SEQUENCE: 187
tgttttgatt cggtacatct ttg                                                23

<210> SEQ ID NO 188
<211> LENGTH: 21
<212> TYPE: DNA
<213> ORGANISM: Artificial Sequence
<220> FEATURE:
<223> OTHER INFORMATION: capture probe 3a3

<400> SEQUENCE: 188
ttgatttggt acatctttgc t                                                  21

<210> SEQ ID NO 189
<211> LENGTH: 20
<212> TYPE: DNA
<213> ORGANISM: Artificial Sequence
<220> FEATURE:
<223> OTHER INFORMATION: capture probe 3A9

<400> SEQUENCE: 189
actcctgggg gttttgggtg                                                    20

<210> SEQ ID NO 190
<211> LENGTH: 24
<212> TYPE: DNA
<213> ORGANISM: Artificial Sequence
<220> FEATURE:
<223> OTHER INFORMATION: capture probe 3A18

<400> SEQUENCE: 190
attactgagt attcagaaat tcac                                               24

<210> SEQ ID NO 191
<211> LENGTH: 25

<212> TYPE: DNA
<213> ORGANISM: Artificial Sequence
<220> FEATURE:
<223> OTHER INFORMATION: capture probe 3A2

<400> SEQUENCE: 191
ggttaaagat tggtacatt tatgg                                      25

<210> SEQ ID NO 192
<211> LENGTH: 22
<212> TYPE: DNA
<213> ORGANISM: Artificial Sequence
<220> FEATURE:
<223> OTHER INFORMATION: consensus primer OPP35S1 (P-35S) Forward

<400> SEQUENCE: 192
cgtcttcaaa gcaagtggat tg                                        22

<210> SEQ ID NO 193
<211> LENGTH: 24
<212> TYPE: DNA
<213> ORGANISM: Artificial Sequence
<220> FEATURE:
<223> OTHER INFORMATION: consensus primer OPT352 (T-35S)  Reverse

<400> SEQUENCE: 193
gaaaccctaa ttcccttatc aggg                                      24

<210> SEQ ID NO 194
<211> LENGTH: 25
<212> TYPE: DNA
<213> ORGANISM: Artificial Sequence
<220> FEATURE:
<223> OTHER INFORMATION: consensus primer OPTE91 (T-E91)  Forward

<400> SEQUENCE: 194
tcatggattt gtagttgagt atgaa                                     25

<210> SEQ ID NO 195
<211> LENGTH: 27
<212> TYPE: DNA
<213> ORGANISM: Artificial Sequence
<220> FEATURE:
<223> OTHER INFORMATION: consensus primer OPTnos2 (T-nos)  Reverse

<400> SEQUENCE: 195
atcttaagaa actttattgc caaatgt                                   27

<210> SEQ ID NO 196
<211> LENGTH: 21
<212> TYPE: DNA
<213> ORGANISM: Artificial Sequence
<220> FEATURE:
<223> OTHER INFORMATION: consensus primer OPEPS3 (EPSPS)  Forward

<400> SEQUENCE: 196
gctgtagttg ttggctgtgg t                                         21

<210> SEQ ID NO 197
<211> LENGTH: 21
<212> TYPE: DNA
<213> ORGANISM: Artificial Sequence
<220> FEATURE:
<223> OTHER INFORMATION: consensus primer OPTE92 (T-E9) Reverse

<400> SEQUENCE: 197
ctgatgcatt gaacttgacg a                                              21

<210> SEQ ID NO 198
<211> LENGTH: 25
<212> TYPE: DNA
<213> ORGANISM: Artificial Sequence
<220> FEATURE:
<223> OTHER INFORMATION: consensus primer OPLB1 (octopine Left Border)
      Forward

<400> SEQUENCE: 198
atcagcaatg agtatgatgg tcaat                                          25

<210> SEQ ID NO 199
<211> LENGTH: 20
<212> TYPE: DNA
<213> ORGANISM: Artificial Sequence
<220> FEATURE:
<223> OTHER INFORMATION: consensus primer OPEPS4 (EPSPS) Reverse

<400> SEQUENCE: 199
gcgacatcag gcatcttgtt                                                20

<210> SEQ ID NO 200
<211> LENGTH: 22
<212> TYPE: DNA
<213> ORGANISM: Artificial Sequence
<220> FEATURE:
<223> OTHER INFORMATION: consensus primer OPLB3 (nopaline Left Border)
      Forward

<400> SEQUENCE: 200
acaaattgac gcttagacaa ct                                             22

<210> SEQ ID NO 201
<211> LENGTH: 21
<212> TYPE: DNA
<213> ORGANISM: Artificial Sequence
<220> FEATURE:
<223> OTHER INFORMATION: consensus primer OPRB2 (octopine Right Border)
      Reverse

<400> SEQUENCE: 201
tgccagtcag catcatcaca c                                              21

<210> SEQ ID NO 202
<211> LENGTH: 21
<212> TYPE: DNA
<213> ORGANISM: Artificial Sequence
<220> FEATURE:
<223> OTHER INFORMATION: consensus primer OPRB4 (nopaliine Right Border)
      Reverse

<400> SEQUENCE: 202
taagggagtc acgttatgac c                                              21

<210> SEQ ID NO 203
<211> LENGTH: 30
<212> TYPE: DNA
<213> ORGANISM: Artificial Sequence
<220> FEATURE:
<223> OTHER INFORMATION: capture probe OT1 pat (T25, Bt11)

<400> SEQUENCE: 203
tggtggatgg catgatgttg gttttttggca                                    30

```
<210> SEQ ID NO 204
<211> LENGTH: 30
<212> TYPE: DNA
<213> ORGANISM: Artificial Sequence
<220> FEATURE:
<223> OTHER INFORMATION: capture probe OT2 CryIAb (Bt11)

<400> SEQUENCE: 204
gcacgaagct ctgcaatcgc acaaacccgt                               30

<210> SEQ ID NO 205
<211> LENGTH: 30
<212> TYPE: DNA
<213> ORGANISM: Artificial Sequence
<220> FEATURE:
<223> OTHER INFORMATION: capture probe OT3 P-PCK (Bt176)

<400> SEQUENCE: 205
tgggggtagc tgtagtcgga ctcggactgg                               30

<210> SEQ ID NO 206
<211> LENGTH: 30
<212> TYPE: DNA
<213> ORGANISM: Artificial Sequence
<220> FEATURE:
<223> OTHER INFORMATION: capture probe OT4 CP4EPSPS/Tnos

<400> SEQUENCE: 206 agccccctagc tagggggtgg ccaggaagta                              30

<210> SEQ ID NO 207
<211> LENGTH: 20
<212> TYPE: DNA
<213> ORGANISM: Artificial Sequence
<220> FEATURE:
<223> OTHER INFORMATION: consensus primer Pgyr1
<221> NAME/KEY: misc_feature
<222> LOCATION: (1)...(20)
<223> OTHER INFORMATION: n = A,T,C or G

<400> SEQUENCE: 207
gangtnatsg gtaaatayca                                          20

<210> SEQ ID NO 208
<211> LENGTH: 17
<212> TYPE: DNA
<213> ORGANISM: Artificial Sequence
<220> FEATURE:
<223> OTHER INFORMATION: consensus primer Pgyr2
<221> NAME/KEY: misc_feature
<222> LOCATION: (1)...(17)
<223> OTHER INFORMATION: n = A,T,C or G

<400> SEQUENCE: 208
cgnryytcvg trtaacg                                             17

<210> SEQ ID NO 209
<211> LENGTH: 90
<212> TYPE: DNA
<213> ORGANISM: Artificial Sequence
<220> FEATURE:
<223> OTHER INFORMATION: spacer sequence

<400> SEQUENCE: 209
ataaaaaagt gggtcttaga aataaatttc gaagtgcaat aattattatt cacaacattt    60 cgattttgc aactacttca gttcactcca                                90
```

```
<210> SEQ ID NO 210
<211> LENGTH: 34
<212> TYPE: DNA
<213> ORGANISM: Staphylococcus genus

<400> SEQUENCE: 210
gactcwtcaa tttatgawgc hatggtahga aygg                         34

<210> SEQ ID NO 211
<211> LENGTH: 30
<212> TYPE: DNA
<213> ORGANISM: Enterococcus genus

<400> SEQUENCE: 211
gacagtgcga tytaygartc aatggtrcgg                              30

<210> SEQ ID NO 212
<211> LENGTH: 29
<212> TYPE: DNA
<213> ORGANISM: Streptococcus genus

<400> SEQUENCE: 212
tggttcgtat ggctcaatgg tggagytay                               29

<210> SEQ ID NO 213
<211> LENGTH: 28
<212> TYPE: DNA
<213> ORGANISM: Staphylococcus aureus

<400> SEQUENCE: 213
ctcaagattt cagttatcgt tatccgct                                28

<210> SEQ ID NO 214
<211> LENGTH: 28
<212> TYPE: DNA
<213> ORGANISM: Staphylococcus epidermidis

<400> SEQUENCE: 214
cccaagactt tagttatcgt tatccact                                28

<210> SEQ ID NO 215
<211> LENGTH: 27
<212> TYPE: DNA
<213> ORGANISM: Staphylococcus hominis

<400> SEQUENCE: 215
cacaaacctt tagctatcgt tatcctc                                 27

<210> SEQ ID NO 216
<211> LENGTH: 27
<212> TYPE: DNA
<213> ORGANISM: Enterococcus faecium

<400> SEQUENCE: 216
acagccattc agctaccgtt atatgct                                 27

<210> SEQ ID NO 217
<211> LENGTH: 29
<212> TYPE: DNA
<213> ORGANISM: Enterococcus faecalis

<400> SEQUENCE: 217
aaccttttag ttatcgggct atgttagtt                               29
```

<210> SEQ ID NO 218
<211> LENGTH: 25
<212> TYPE: DNA
<213> ORGANISM: Streptococcus pneumoniae

<400> SEQUENCE: 218
gatggagata gtgctgccgc tcaac                                         25

<210> SEQ ID NO 219
<211> LENGTH: 26
<212> TYPE: DNA
<213> ORGANISM: Streptococcus epyogenes

<400> SEQUENCE: 219
cttgttgatg ggcatggcaa ttttgg                                        26

<210> SEQ ID NO 220
<211> LENGTH: 28
<212> TYPE: DNA
<213> ORGANISM: Haemophilus influenzae

<400> SEQUENCE: 220
ttctcacttc gctatatgtt ggttgatg                                      28

<210> SEQ ID NO 221
<211> LENGTH: 27
<212> TYPE: DNA
<213> ORGANISM: Artificial Sequence
<220> FEATURE:
<223> OTHER INFORMATION: 5' aminated primer

<400> SEQUENCE: 221
gaattcaaag ttgctgagaa tagttca                                       27

<210> SEQ ID NO 222
<211> LENGTH: 16
<212> TYPE: DNA
<213> ORGANISM: Artificial Sequence
<220> FEATURE:
<223> OTHER INFORMATION: viral consensus primer
<221> NAME/KEY: misc_difference
<222> LOCATION: (1)...(1)
<223> OTHER INFORMATION: N is A or G
<221> NAME/KEY: misc_difference
<222> LOCATION: (2)...(2)
<223> OTHER INFORMATION: N is C, A or T
<221> NAME/KEY: misc_difference
<222> LOCATION: (3)...(3)
<223> OTHER INFORMATION: N is G, C or T
<221> NAME/KEY: misc_difference
<222> LOCATION: (13)...(13)
<223> OTHER INFORMATION: N is T or A
<221> NAME/KEY: misc_difference
<222> LOCATION: (14)...(14)
<223> OTHER INFORMATION: N is T, A or C
<221> NAME/KEY: misc_difference
<222> LOCATION: (15)...(15)
<223> OTHER INFORMATION: N is C or T
<221> NAME/KEY: misc_difference
<222> LOCATION: (16)...(16)
<223> OTHER INFORMATION: N is G, A or C

<400> SEQUENCE: 222
nnngccgccg tgnnnn                                                   16

<210> SEQ ID NO 223
<211> LENGTH: 16

```
<212> TYPE: DNA
<213> ORGANISM: Artificial Sequence
<220> FEATURE:
<223> OTHER INFORMATION: viral consensus primer
<221> NAME/KEY: misc_difference
<222> LOCATION: (2)...(2)
<223> OTHER INFORMATION: N is T, G or C
<221> NAME/KEY: misc_difference
<222> LOCATION: (3)...(3)
<223> OTHER INFORMATION: N is G, T or A
<221> NAME/KEY: misc_difference
<222> LOCATION: (13)...(13)
<223> OTHER INFORMATION: N is G or A
<221> NAME/KEY: misc_difference
<222> LOCATION: (14)...(14)
<223> OTHER INFORMATION: N is T or C
<221> NAME/KEY: misc_difference
<222> LOCATION: (15)...(15)
<223> OTHER INFORMATION: N is G or C
<221> NAME/KEY: misc_difference
<222> LOCATION: (16)...(16)
<223> OTHER INFORMATION: N is G or T

<400> SEQUENCE: 223
gnngttgttt ttnnnn                                                        16

<210> SEQ ID NO 224
<211> LENGTH: 27
<212> TYPE: DNA
<213> ORGANISM: Artificial Sequence
<220> FEATURE:
<223> OTHER INFORMATION: Adenovirus capture nucleotide sequence

<400> SEQUENCE: 224
aactcttctc gctggcactc aagagtg                                            27

<210> SEQ ID NO 225
<211> LENGTH: 27
<212> TYPE: DNA
<213> ORGANISM: Artificial Sequence
<220> FEATURE:
<223> OTHER INFORMATION: Herpes virus 1 capture nucleotide sequence

<400> SEQUENCE: 225
gtggaagtcc tgatacccat cctacac                                            27

<210> SEQ ID NO 226
<211> LENGTH: 27
<212> TYPE: DNA
<213> ORGANISM: Artificial Sequence
<220> FEATURE:
<223> OTHER INFORMATION: Herpes virus 5 capture nucleotide sequence

<400> SEQUENCE: 226
aaaagcgtgt gatctgaccg aggcgaa                                            27

<210> SEQ ID NO 227
<211> LENGTH: 27
<212> TYPE: DNA
<213> ORGANISM: Artificial Sequence
<220> FEATURE:
<223> OTHER INFORMATION: Herpes virus 4 capture nucleotide sequence

<400> SEQUENCE: 227
aggtccttga ggaagaagtg ttccagg                                            27

<210> SEQ ID NO 228
<211> LENGTH: 21
<212> TYPE: DNA
```

```
<213> ORGANISM: Artificial Sequence
<220> FEATURE:
<223> OTHER INFORMATION: consensus primer Meat1

<400> SEQUENCE: 228
tcctcccatg aggagaaata t                                              21

<210> SEQ ID NO 229
<211> LENGTH: 21
<212> TYPE: DNA
<213> ORGANISM: Artificial Sequence
<220> FEATURE:
<223> OTHER INFORMATION: consensus primer Meat2

<400> SEQUENCE: 229
agcgaagaat cgggtaaggg t                                              21

<210> SEQ ID NO 230
<211> LENGTH: 39
<212> TYPE: DNA
<213> ORGANISM: Artificial Sequence
<220> FEATURE:
<223> OTHER INFORMATION: Chicken capture nucleotide sequence

<400> SEQUENCE: 230
ccttaacgac tcttatccaa acactatgcc accggggag                           39

<210> SEQ ID NO 231
<211> LENGTH: 40
<212> TYPE: DNA
<213> ORGANISM: Artificial Sequence
<220> FEATURE:
<223> OTHER INFORMATION: Duck capture nucleotide sequence

<400> SEQUENCE: 231
ccctaacgac tcttatccaa acactactgc catcggggag                          40

<210> SEQ ID NO 232
<211> LENGTH: 17
<212> TYPE: DNA
<213> ORGANISM: Artificial Sequence
<220> FEATURE:
<223> OTHER INFORMATION: Ostrich capture nucleotide sequence

<400> SEQUENCE: 232
ccttaacgaa ctctaag                                                   17

<210> SEQ ID NO 233
<211> LENGTH: 25
<212> TYPE: DNA
<213> ORGANISM: Artificial Sequence
<220> FEATURE:
<223> OTHER INFORMATION: Pig capture nucleotide sequence

<400> SEQUENCE: 233
aaagaggagt agaatcacga ttaag                                          25

<210> SEQ ID NO 234
<211> LENGTH: 40
<212> TYPE: DNA
<213> ORGANISM: Artificial Sequence
<220> FEATURE:
<223> OTHER INFORMATION: Quail capture nucleotide sequence

<400> SEQUENCE: 234
ccatgtcgac tcttatccaa acactactgc catcgtggag                          40
```

<210> SEQ ID NO 235
<211> LENGTH: 40
<212> TYPE: DNA
<213> ORGANISM: Artificial Sequence
<220> FEATURE:
<223> OTHER INFORMATION: Rabbit capture nucleotide sequence

<400> SEQUENCE: 235
ccctaacgac tatcctccaa tcactaatgc caacgagggg                    40

<210> SEQ ID NO 236
<211> LENGTH: 39
<212> TYPE: DNA
<213> ORGANISM: Artificial Sequence
<220> FEATURE:
<223> OTHER INFORMATION: Turkey capture nucleotide sequence

<400> SEQUENCE: 236
ccctaacgac tcttatccaa acactactgc catcgggag                     39

<210> SEQ ID NO 237
<211> LENGTH: 40
<212> TYPE: DNA
<213> ORGANISM: Artificial Sequence
<220> FEATURE:
<223> OTHER INFORMATION: Wildpig capture nucleotide sequence

<400> SEQUENCE: 237
ccctatcgac tatcttctaa acactactgg catcgaggag                    40

<210> SEQ ID NO 238
<211> LENGTH: 39
<212> TYPE: DNA
<213> ORGANISM: Artificial Sequence
<220> FEATURE:
<223> OTHER INFORMATION: Cow capture nucleotide sequence

<400> SEQUENCE: 238
cctaacgact attctccaac cactactgac aacgaggag                     39

<210> SEQ ID NO 239
<211> LENGTH: 96
<212> TYPE: DNA
<213> ORGANISM: Artificial Sequence
<220> FEATURE:
<223> OTHER INFORMATION: consensus capture nucleotide sequence for
    cytochrome b

<400> SEQUENCE: 239
attctgaggg gcaccgtcat cacaaaccta tttcagcaat ccctacatg gcaaaccta   60 gtagaatgag cctgaggggg attttcagtg acaacc                           96

<210> SEQ ID NO 240
<211> LENGTH: 23
<212> TYPE: DNA
<213> ORGANISM: Artificial Sequence
<220> FEATURE:
<223> OTHER INFORMATION: consensus primer Cow1

<400> SEQUENCE: 240
aagacataat atgtatatag tac                                     23

<210> SEQ ID NO 241
<211> LENGTH: 23

```
<212> TYPE: DNA
<213> ORGANISM: Artificial Sequence
<220> FEATURE:
<223> OTHER INFORMATION: consensus primer Cow2

<400> SEQUENCE: 241
gaaaaattta ataagtatc tag                                              23

<210> SEQ ID NO 242
<211> LENGTH: 15
<212> TYPE: DNA
<213> ORGANISM: Artificial Sequence
<220> FEATURE:
<223> OTHER INFORMATION: BrownSwiss capture nucleotide sequence

<400> SEQUENCE: 242
gcggcatgat aatta                                                      15

<210> SEQ ID NO 243
<211> LENGTH: 15
<212> TYPE: DNA
<213> ORGANISM: Artificial Sequence
<220> FEATURE:
<223> OTHER INFORMATION: Jersey capture nucleotide sequence

<400> SEQUENCE: 243
cgctattcaa tgaat                                                      15

<210> SEQ ID NO 244
<211> LENGTH: 15
<212> TYPE: DNA
<213> ORGANISM: Artificial Sequence
<220> FEATURE:
<223> OTHER INFORMATION: Ayrshire capture nucleotide sequence

<400> SEQUENCE: 244
gctcaccata actgt                                                      15

<210> SEQ ID NO 245
<211> LENGTH: 15
<212> TYPE: DNA
<213> ORGANISM: Artificial Sequence
<220> FEATURE:
<223> OTHER INFORMATION: Hereford capture nucleotide sequence

<400> SEQUENCE: 245
atctgatggt aagga                                                      15

<210> SEQ ID NO 246
<211> LENGTH: 15
<212> TYPE: DNA
<213> ORGANISM: Artificial Sequence
<220> FEATURE:
<223> OTHER INFORMATION: Simmental capture nucleotide sequence

<400> SEQUENCE: 246
ataagcctgg acatt                                                      15

<210> SEQ ID NO 247
<211> LENGTH: 15
<212> TYPE: DNA
<213> ORGANISM: Artificial Sequence
<220> FEATURE:
<223> OTHER INFORMATION: Piemontaise capture nucleotide sequence

<400> SEQUENCE: 247
```
ataagcatgg acatt                                                    15

<210> SEQ ID NO 248
<211> LENGTH: 15
<212> TYPE: DNA
<213> ORGANISM: Artificial Sequence
<220> FEATURE:
<223> OTHER INFORMATION: Canadienne capture nucleotide sequence

<400> SEQUENCE: 248
tcactcggca tgata                                                    15

<210> SEQ ID NO 249
<211> LENGTH: 15
<212> TYPE: DNA
<213> ORGANISM: Artificial Sequence
<220> FEATURE:
<223> OTHER INFORMATION: RedAngus capture nucleotide sequence

<400> SEQUENCE: 249
aatggtaggg gatat                                                    15

<210> SEQ ID NO 250
<211> LENGTH: 15
<212> TYPE: DNA
<213> ORGANISM: Artificial Sequence
<220> FEATURE:
<223> OTHER INFORMATION: Limousine capture nucleotide sequence

<400> SEQUENCE: 250
atggactcat ggcta                                                    15

<210> SEQ ID NO 251
<211> LENGTH: 15
<212> TYPE: DNA
<213> ORGANISM: Artificial Sequence
<220> FEATURE:
<223> OTHER INFORMATION: AberdeenAngus capture nucleotide sequence

<400> SEQUENCE: 251
tattcaatga acttt                                                    15

<210> SEQ ID NO 252
<211> LENGTH: 15
<212> TYPE: DNA
<213> ORGANISM: Artificial Sequence
<220> FEATURE:
<223> OTHER INFORMATION: Butana capture nucleotide sequence

<400> SEQUENCE: 252 gcatgggta tataa                                                     15

<210> SEQ ID NO 253
<211> LENGTH: 16
<212> TYPE: DNA
<213> ORGANISM: Artificial Sequence
<220> FEATURE:
<223> OTHER INFORMATION: Charolais capture nucleotide sequence

<400> SEQUENCE: 253
ataagcgtgg acatta                                                   16

<210> SEQ ID NO 254
<211> LENGTH: 15
<212> TYPE: DNA
<213> ORGANISM: Artificial Sequence

```
<220> FEATURE:
<223> OTHER INFORMATION: Fresian capture nucleotide sequence

<400> SEQUENCE: 254
ccttaaatac ctacc                                                    15

<210> SEQ ID NO 255
<211> LENGTH: 15
<212> TYPE: DNA
<213> ORGANISM: Artificial Sequence
<220> FEATURE:
<223> OTHER INFORMATION: Kenana capture nucleotide sequence

<400> SEQUENCE: 255
tgctatagaa gtcat                                                    15

<210> SEQ ID NO 256
<211> LENGTH: 15
<212> TYPE: DNA
<213> ORGANISM: Artificial Sequence
<220> FEATURE:
<223> OTHER INFORMATION: N 'Dama capture nucleotide sequence

<400> SEQUENCE: 256
tgttatagaa gtcat                                                    15

<210> SEQ ID NO 257
<211> LENGTH: 20
<212> TYPE: DNA
<213> ORGANISM: Artificial Sequence
<220> FEATURE:
<223> OTHER INFORMATION: consensus primer PPss3
<221> NAME/KEY: misc_feature
<222> LOCATION: (1)...(20)
<223> OTHER INFORMATION: n = A,T,C or G

<400> SEQUENCE: 257
ggtttggaga rrggntgggg                                               20

<210> SEQ ID NO 258
<211> LENGTH: 20
<212> TYPE: DNA
<213> ORGANISM: Artificial Sequence
<220> FEATURE:
<223> OTHER INFORMATION: consensus primer PPss4

<400> SEQUENCE: 258
tccaadatgt avacaacctg                                               20

<210> SEQ ID NO 259
<211> LENGTH: 24
<212> TYPE: DNA
<213> ORGANISM: Artificial Sequence
<220> FEATURE:
<223> OTHER INFORMATION: TPss1 (potato) capture nucleotide sequence

<400> SEQUENCE: 259
gaagcatgca taccatctct agca                                          24

<210> SEQ ID NO 260
<211> LENGTH: 24
<212> TYPE: DNA
<213> ORGANISM: Artificial Sequence
<220> FEATURE:
<223> OTHER INFORMATION: TPss3 (tomato) capture nucleotide sequence

<400> SEQUENCE: 260
```
ggagcatgca gatcatctct agaa								24

<210> SEQ ID NO 261
<211> LENGTH: 24
<212> TYPE: DNA
<213> ORGANISM: Artificial Sequence
<220> FEATURE:
<223> OTHER INFORMATION: TPss7 (oryza) capture nucleotide sequence

<400> SEQUENCE: 261
gaagcaagtg gatggtgtca agca								24

<210> SEQ ID NO 262
<211> LENGTH: 24
<212> TYPE: DNA
<213> ORGANISM: Artificial Sequence
<220> FEATURE:
<223> OTHER INFORMATION: TPss8 (zea) capture nucleotide sequence

<400> SEQUENCE: 262
agaggaggtg gatagtctcc tgtg								24

<210> SEQ ID NO 263
<211> LENGTH: 24
<212> TYPE: DNA
<213> ORGANISM: Artificial Sequence
<220> FEATURE:
<223> OTHER INFORMATION: TPss9 (soja) capture nucleotide sequence

<400> SEQUENCE: 263
agagaagttg aattgactca agga								24

<210> SEQ ID NO 264
<211> LENGTH: 24
<212> TYPE: DNA
<213> ORGANISM: Artificial Sequence
<220> FEATURE:
<223> OTHER INFORMATION: TPss11 (wheat) capture nucleotide sequence

<400> SEQUENCE: 264
agagaaggtg gatagtctcg ctcg								24

<210> SEQ ID NO 265
<211> LENGTH: 24
<212> TYPE: DNA
<213> ORGANISM: Artificial Sequence
<220> FEATURE:
<223> OTHER INFORMATION: TPss12 (bareley) capture nucleotide sequence

<400> SEQUENCE: 265
agagaaggtg gatagtctcg ctcg								24

<210> SEQ ID NO 266
<211> LENGTH: 24
<212> TYPE: DNA
<213> ORGANISM: Artificial Sequence
<220> FEATURE:
<223> OTHER INFORMATION: TPss13 (bean) capture nucleotide sequence

<400> SEQUENCE: 266
atagaagctg aatggactcg agca								24

<210> SEQ ID NO 267
<211> LENGTH: 24
<212> TYPE: DNA

-continued

```
<213> ORGANISM: Artificial Sequence
<220> FEATURE:
<223> OTHER INFORMATION: TPss14 (carrot) capture nucleotide sequence

<400> SEQUENCE: 267
gaagcatgtg aaacatctca gtaa                                          24

<210> SEQ ID NO 268
<211> LENGTH: 21
<212> TYPE: DNA
<213> ORGANISM: Artificial Sequence
<220> FEATURE:
<223> OTHER INFORMATION: Fish1 consensus primer

<400> SEQUENCE: 268
actatthcta gccatvcayt a                                             21

<210> SEQ ID NO 269
<211> LENGTH: 23
<212> TYPE: DNA
<213> ORGANISM: Artificial Sequence
<220> FEATURE:
<223> OTHER INFORMATION: Fish2 consensus primer

<400> SEQUENCE: 269
aggtaggagc cataaagacc tcg                                           23

<210> SEQ ID NO 270
<211> LENGTH: 28
<212> TYPE: DNA
<213> ORGANISM: Artificial Sequence
<220> FEATURE:
<223> OTHER INFORMATION: G. morhua capture nucleotide sequence

<400> SEQUENCE: 270
aaggcttaat cagtcggcat caaatgta                                      28

<210> SEQ ID NO 271
<211> LENGTH: 28
<212> TYPE: DNA
<213> ORGANISM: Artificial Sequence
<220> FEATURE:
<223> OTHER INFORMATION: G. macrocephalus capture nucleotide sequence

<400> SEQUENCE: 271
aaggcttact cagttggcat taaatgta                                      28

<210> SEQ ID NO 272
<211> LENGTH: 28
<212> TYPE: DNA
<213> ORGANISM: Artificial Sequence
<220> FEATURE:
<223> OTHER INFORMATION: P. flesus capture nucleotide sequence

<400> SEQUENCE: 272
gaagcctact cagttggcat caactgca                                      28

<210> SEQ ID NO 273
<211> LENGTH: 28
<212> TYPE: DNA
<213> ORGANISM: Artificial Sequence
<220> FEATURE:
<223> OTHER INFORMATION: M. merluccius capture nucleotide sequence

<400> SEQUENCE: 273
aacgcctaat cagtaggcat taaatgca                                      28
```

```
<210> SEQ ID NO 274
<211> LENGTH: 28
<212> TYPE: DNA
<213> ORGANISM: Artificial Sequence
<220> FEATURE:
<223> OTHER INFORMATION: O. mykiss capture nucleotide sequence

<400> SEQUENCE: 274
aaagcttact cagtcggcat tgattgta                                      28

<210> SEQ ID NO 275
<211> LENGTH: 28
<212> TYPE: DNA
<213> ORGANISM: Artificial Sequence
<220> FEATURE:
<223> OTHER INFORMATION: P. platessa capture nucleotide sequence

<400> SEQUENCE: 275
gaagcctatt cagtcggcat caactgca                                      28

<210> SEQ ID NO 276
<211> LENGTH: 28
<212> TYPE: DNA
<213> ORGANISM: Artificial Sequence
<220> FEATURE:
<223> OTHER INFORMATION: P. virens capture nucleotide sequence

<400> SEQUENCE: 276
aaagcttaat tagtcggcat taaatgta                                      28

<210> SEQ ID NO 277
<211> LENGTH: 29
<212> TYPE: DNA
<213> ORGANISM: Artificial Sequence
<220> FEATURE:
<223> OTHER INFORMATION: S. salar capture nucleotide sequence

<400> SEQUENCE: 277
caatgcctac tcagtcggta tcgattgta                                     29

<210> SEQ ID NO 278
<211> LENGTH: 28
<212> TYPE: DNA
<213> ORGANISM: Artificial Sequence
<220> FEATURE:
<223> OTHER INFORMATION: S. pilchardus capture nucleotide sequence

<400> SEQUENCE: 278
gaagcttagt cagtaggcat caaatgca                                      28

<210> SEQ ID NO 279
<211> LENGTH: 28
<212> TYPE: DNA
<213> ORGANISM: Artificial Sequence
<220> FEATURE:
<223> OTHER INFORMATION: A. thazard capture nucleotide sequence

<400> SEQUENCE: 279
aaagcctatt cagttggctt caaatgta                                      28

<210> SEQ ID NO 280
<211> LENGTH: 28
<212> TYPE: DNA
<213> ORGANISM: Artificial Sequence
<220> FEATURE:
```

-continued

<223> OTHER INFORMATION: T. alalunga capture nucleotide sequence

<400> SEQUENCE: 280
aaagcctact cagtaggctt caaatgta                                28

<210> SEQ ID NO 281
<211> LENGTH: 29
<212> TYPE: DNA
<213> ORGANISM: Artificial Sequence
<220> FEATURE:
<223> OTHER INFORMATION: T. obesus capture nucleotide sequence

<400> SEQUENCE: 281
aaagcctact cagttggctt taactgtta                               29

<210> SEQ ID NO 282
<211> LENGTH: 28
<212> TYPE: DNA
<213> ORGANISM: Artificial Sequence
<220> FEATURE:
<223> OTHER INFORMATION: R. hippoglossoides capture nucleotide sequence

<400> SEQUENCE: 282
gaagcctatt cagtcggcat caactgca                                28

<210> SEQ ID NO 283
<211> LENGTH: 28
<212> TYPE: DNA
<213> ORGANISM: Artificial Sequence
<220> FEATURE:
<223> OTHER INFORMATION: S. trutta capture nucleotide sequence

<400> SEQUENCE: 283
aaagcctact cagtcggcat cgattgca                                28

<210> SEQ ID NO 284
<211> LENGTH: 28
<212> TYPE: DNA
<213> ORGANISM: Artificial Sequence
<220> FEATURE:
<223> OTHER INFORMATION: S. sarda capture nucleotide sequence

<400> SEQUENCE: 284
aaagcctaat cagtcggctt taattgca                                28

<210> SEQ ID NO 285
<211> LENGTH: 28
<212> TYPE: DNA
<213> ORGANISM: Artificial Sequence
<220> FEATURE:
<223> OTHER INFORMATION: T. thynnus capture nucleotide sequence

<400> SEQUENCE: 285
aaggcctatt cagttggctt caactgta                                28

<210> SEQ ID NO 286
<211> LENGTH: 28
<212> TYPE: DNA
<213> ORGANISM: Artificial Sequence
<220> FEATURE:
<223> OTHER INFORMATION: S. scrombrus capture nucleotide sequence

<400> SEQUENCE: 286
aacgcctact cagtaggctt caaatgca                                28

<210> SEQ ID NO 287
<211> LENGTH: 40
<212> TYPE: DNA
<213> ORGANISM: Artificial Sequence
<220> FEATURE:
<223> OTHER INFORMATION: Salmonidae family capture nucleotide sequence

<400> SEQUENCE: 287
aaacattcac gctaacggag catctttctt ctttatctgt                     40

<210> SEQ ID NO 288
<211> LENGTH: 40
<212> TYPE: DNA
<213> ORGANISM: Artificial Sequence
<220> FEATURE:
<223> OTHER INFORMATION: Pleuronectidae family capture nucleotide
      sequence

<400> SEQUENCE: 288
aagcattcat gccaacggcg catcattctt tttcatttgc                     40

<210> SEQ ID NO 289
<211> LENGTH: 40
<212> TYPE: DNA
<213> ORGANISM: Artificial Sequence
<220> FEATURE:
<223> OTHER INFORMATION: Pleuronectidae family capture nucleotide
      sequence

<400> SEQUENCE: 289
gaatatacat gctaatggtg cctctttctt ttttatttgt                     40

<210> SEQ ID NO 290
<211> LENGTH: 41
<212> TYPE: DNA
<213> ORGANISM: Artificial Sequence
<220> FEATURE:
<223> OTHER INFORMATION: Scrombridae family capture nucleotide sequence

<400> SEQUENCE: 290
aaacctccac gcaaacggag cctctttctt tctttatctg c                   41

<210> SEQ ID NO 291
<211> LENGTH: 15
<212> TYPE: DNA
<213> ORGANISM: Artificial Sequence
<220> FEATURE:
<223> OTHER INFORMATION: Thunnus genus capture nucleotide sequence

<400> SEQUENCE: 291
attccacatc ggccg                                                15

<210> SEQ ID NO 292
<211> LENGTH: 57
<212> TYPE: DNA
<213> ORGANISM: Artificial Sequence
<220> FEATURE:
<223> OTHER INFORMATION: Fish consensus capture nucleotide sequence

<400> SEQUENCE: 292
atccgaaaca tccacgcaac gggcatcttt cttctttatc tgtatctact tacacat    57

<210> SEQ ID NO 293
<211> LENGTH: 24
<212> TYPE: DNA
<213> ORGANISM: Artificial Sequence
<220> FEATURE:

-continued

```
<223> OTHER INFORMATION: P450-1 consensus primer

<400> SEQUENCE: 293
tccgcaactt gggcctgggc aaga                                          24

<210> SEQ ID NO 294
<211> LENGTH: 23
<212> TYPE: DNA
<213> ORGANISM: Artificial Sequence
<220> FEATURE:
<223> OTHER INFORMATION: P450-2 consensus primer

<400> SEQUENCE: 294
ccttctccat ctctgccagg aag                                           23

<210> SEQ ID NO 295
<211> LENGTH: 17
<212> TYPE: DNA
<213> ORGANISM: Artificial Sequence
<220> FEATURE:
<223> OTHER INFORMATION: Human CYP2D6 wild-type capture nucleotide
      sequence

<400> SEQUENCE: 295
gaaaggggcg tcctggg                                                  17

<210> SEQ ID NO 296
<211> LENGTH: 17
<212> TYPE: DNA
<213> ORGANISM: Artificial Sequence
<220> FEATURE:
<223> OTHER INFORMATION: Human CYP2D6 capture nucleotide sequence, point
      mutation

<400> SEQUENCE: 296
gaaaggggcg tcttggg                                                  17

<210> SEQ ID NO 297
<211> LENGTH: 17
<212> TYPE: DNA
<213> ORGANISM: Artificial Sequence
<220> FEATURE:
<223> OTHER INFORMATION: Human CYP2D6 capture nucleotide sequence, wild
      type

<400> SEQUENCE: 297
gctaactgag cacagga                                                  17

<210> SEQ ID NO 298
<211> LENGTH: 16
<212> TYPE: DNA
<213> ORGANISM: Artificial Sequence
<220> FEATURE:
<223> OTHER INFORMATION: Human CYP2D6 capture nucleotide sequence
      (deletion)

<400> SEQUENCE: 298
gctaactgag cacgga                                                   16

<210> SEQ ID NO 299
<211> LENGTH: 16
<212> TYPE: DNA
<213> ORGANISM: Artificial Sequence
<220> FEATURE:
<223> OTHER INFORMATION: Human CYP2D6 capture nucleotide sequence, wild
      type
```

```
<400> SEQUENCE: 299
ctcggtcacc ccctgc                                                    16

<210> SEQ ID NO 300
<211> LENGTH: 15
<212> TYPE: DNA
<213> ORGANISM: Artificial Sequence
<220> FEATURE:
<223> OTHER INFORMATION: Human CYP2D6 capture nucleotide sequence
      (deletion)

<400> SEQUENCE: 300
ctcggtcacc cctgc                                                     15

<210> SEQ ID NO 301
<211> LENGTH: 16
<212> TYPE: DNA
<213> ORGANISM: Artificial Sequence
<220> FEATURE:
<223> OTHER INFORMATION: Human CYP2C19 capture nucleotide sequence, wild
      type

<400> SEQUENCE: 301
aattatttcc caggaa                                                    16

<210> SEQ ID NO 302
<211> LENGTH: 16
<212> TYPE: DNA
<213> ORGANISM: Artificial Sequence
<220> FEATURE:
<223> OTHER INFORMATION: Human CYP2C19 capture nucleotide sequence,
      point mutation

<400> SEQUENCE: 302
aattatttcc caggaa                                                    16

<210> SEQ ID NO 303
<211> LENGTH: 16
<212> TYPE: DNA
<213> ORGANISM: Artificial Sequence
<220> FEATURE:
<223> OTHER INFORMATION: Human CYP2C19 capture nucleotide sequence, wild
      type

<400> SEQUENCE: 303
agcaccccct gaatcc                                                    16

<210> SEQ ID NO 304
<211> LENGTH: 16
<212> TYPE: DNA
<213> ORGANISM: Artificial Sequence
<220> FEATURE:
<223> OTHER INFORMATION: Human CYP2C19 capture nucleotide sequence,
      point mutation

<400> SEQUENCE: 304
agcaccccct gaatcc                                                    16

<210> SEQ ID NO 305
<211> LENGTH: 18
<212> TYPE: DNA
<213> ORGANISM: Artificial Sequence
<220> FEATURE:
<223> OTHER INFORMATION: sense consensus primer, S. saprophyticus

<400> SEQUENCE: 305
```

```
gaattrgttg aaatggaa                                                 18

<210> SEQ ID NO 306
<211> LENGTH: 17
<212> TYPE: DNA
<213> ORGANISM: Artificial Sequence
<220> FEATURE:
<223> OTHER INFORMATION: antisense consensus primer, S. saprophyticus

<400> SEQUENCE: 306
gtagtacgga artagaa                                                  17

<210> SEQ ID NO 307
<211> LENGTH: 16
<212> TYPE: DNA
<213> ORGANISM: Artificial Sequence
<220> FEATURE:
<223> OTHER INFORMATION: sense primer of double labelled probe (S.
      saprophyticus)

<400> SEQUENCE: 307
ggtgttgaaa tgttcc                                                   16

<210> SEQ ID NO 308
<211> LENGTH: 17
<212> TYPE: DNA
<213> ORGANISM: Artificial Sequence
<220> FEATURE:
<223> OTHER INFORMATION: Meningococcus capture probe

<400> SEQUENCE: 308
cgacctgctg tccagct                                                  17

<210> SEQ ID NO 309
<211> LENGTH: 18
<212> TYPE: DNA
<213> ORGANISM: Artificial Sequence
<220> FEATURE:
<223> OTHER INFORMATION: Streptococcus capture probe

<400> SEQUENCE: 309
cttcaggacg tatcgacc                                                 18

<210> SEQ ID NO 310
<211> LENGTH: 19
<212> TYPE: DNA
<213> ORGANISM: Artificial Sequence
<220> FEATURE:
<223> OTHER INFORMATION: Staphylococcus capture probe

<400> SEQUENCE: 310
ttattagact acgctgaag                                                19

<210> SEQ ID NO 311
<211> LENGTH: 18
<212> TYPE: DNA
<213> ORGANISM: Artificial Sequence
<220> FEATURE:
<223> OTHER INFORMATION: N. menengitidis serogroup A capture probe

<400> SEQUENCE: 311
tctatttccg gtcgtggt                                                 18

<210> SEQ ID NO 312
<211> LENGTH: 16
<212> TYPE: DNA
```

```
<213> ORGANISM: Artificial Sequence
<220> FEATURE:
<223> OTHER INFORMATION: N. menengitidis serogroup B capture probe

<400> SEQUENCE: 312
ccatttccgg ccgcgg                                                    16

<210> SEQ ID NO 313
<211> LENGTH: 19
<212> TYPE: DNA
<213> ORGANISM: Artificial Sequence
<220> FEATURE:
<223> OTHER INFORMATION: H. influenzae capture probe

<400> SEQUENCE: 313
gagttagcaa accacttag                                                 19

<210> SEQ ID NO 314
<211> LENGTH: 17
<212> TYPE: DNA
<213> ORGANISM: Artificial Sequence
<220> FEATURE:
<223> OTHER INFORMATION: E. coli capture probe

<400> SEQUENCE: 314
aactggctgg cttcctg                                                   17

<210> SEQ ID NO 315
<211> LENGTH: 21
<212> TYPE: DNA
<213> ORGANISM: Artificial Sequence
<220> FEATURE:
<223> OTHER INFORMATION: S. pneumoniae capture probe

<400> SEQUENCE: 315
gtatcaaaga agaaactcaa a                                              21

<210> SEQ ID NO 316
<211> LENGTH: 21
<212> TYPE: DNA
<213> ORGANISM: Artificial Sequence
<220> FEATURE:
<223> OTHER INFORMATION: S. agalactiae capture probe

<400> SEQUENCE: 316
gtattaaaga agatatccaa a                                              21

<210> SEQ ID NO 317
<211> LENGTH: 20
<212> TYPE: DNA
<213> ORGANISM: Artificial Sequence
<220> FEATURE:
<223> OTHER INFORMATION: S. aureus capture probe

<400> SEQUENCE: 317
ggtttacatg acacatctaa                                                20

<210> SEQ ID NO 318
<211> LENGTH: 20
<212> TYPE: DNA
<213> ORGANISM: Artificial Sequence
<220> FEATURE:
<223> OTHER INFORMATION: S. epidermidis capture probe

<400> SEQUENCE: 318
gtatgcacga aacttctaaa                                                20
```

```
<210> SEQ ID NO 319
<211> LENGTH: 20
<212> TYPE: DNA
<213> ORGANISM: Artificial Sequence
<220> FEATURE:
<223> OTHER INFORMATION: S. haemolyticus capture probe

<400> SEQUENCE: 319
gtatccatga cacttctaaa                                               20

<210> SEQ ID NO 320
<211> LENGTH: 21
<212> TYPE: DNA
<213> ORGANISM: Artificial Sequence
<220> FEATURE:
<223> OTHER INFORMATION: S. hominis capture probe

<400> SEQUENCE: 320
ggtatcaaag aaacttctaa a                                             21

<210> SEQ ID NO 321
<211> LENGTH: 20
<212> TYPE: DNA
<213> ORGANISM: Artificial Sequence
<220> FEATURE:
<223> OTHER INFORMATION: S. saprophyticus capture probe

<400> SEQUENCE: 321
atgcaagaag aatcaagcaa                                               20
```